(12) United States Patent
Zhang et al.

(10) Patent No.: US 9,580,717 B2
(45) Date of Patent: Feb. 28, 2017

(54) HETEROLOGOUS HOSTS

(75) Inventors: Youming Zhang, Heidelberg (DE); Jun Fu, Heidelberg (DE); Xiaoying Bian, Heidelberg (DE); Adrian Francis Stewart, Heidelberg (DE); Rolf Müller, Heidelberg (DE)

(73) Assignee: Gene Bridges GmbH, Heidelberg (DE)

( * ) Notice: Subject to any disclaimer, the term of this patent is extended or adjusted under 35 U.S.C. 154(b) by 1169 days.

(21) Appl. No.: 13/516,758

(22) PCT Filed: Dec. 17, 2010

(86) PCT No.: PCT/IB2010/055923
§ 371 (c)(1),
(2), (4) Date: Dec. 20, 2012

(87) PCT Pub. No.: WO2011/073956
PCT Pub. Date: Jun. 23, 2011

(65) Prior Publication Data
US 2013/0089522 A1     Apr. 11, 2013

(30) Foreign Application Priority Data
Dec. 17, 2009   (GB) .................... 0922108.6

(51) Int. Cl.
| C12N 15/74 | (2006.01) |
| C07D 245/02 | (2006.01) |
| C07D 417/06 | (2006.01) |
| C07D 493/04 | (2006.01) |
| C12N 9/90 | (2006.01) |

(Continued)

(52) U.S. Cl.
CPC .......... *C12N 15/74* (2013.01); *C07D 245/02* (2013.01); *C07D 417/06* (2013.01); *C07D 493/04* (2013.01); *C12N 9/90* (2013.01); *C12N 9/93* (2013.01); *C12N 15/52* (2013.01); *C12N 15/70* (2013.01); *C12P 17/10* (2013.01);

(Continued)

(58) Field of Classification Search
None
See application file for complete search history.

(56) References Cited

U.S. PATENT DOCUMENTS

| 4,692,510 A | 9/1987 | Konishi et al. |
| 4,742,047 A | 5/1988 | Oka et al. |

(Continued)

FOREIGN PATENT DOCUMENTS

| EP | 0103276 | 3/1984 |
| EP | 1809749 | 7/2007 |

(Continued)

OTHER PUBLICATIONS

Fatmi et al. Ed. (Pseudomonas syringae Pathovars and Related Pathogens—Identification, Epidemiology and Genomics, Springer, 2008, p. 249-258).*

(Continued)

*Primary Examiner* — Alexander Kim
(74) *Attorney, Agent, or Firm* — Baker & Hostetler LLP

(57) ABSTRACT

This invention is related to bacterial engineering and the heterologous expression of useful compounds. In particular, the invention relates to a heterologous host that has been engineered for expression of a gene which is capable of polyketide or non-ribosomal peptide synthesis. Methods of treating cancer are also disclosed.

15 Claims, 32 Drawing Sheets

(51) Int. Cl.
- C12N 15/52 (2006.01)
- C12P 17/10 (2006.01)
- C12P 17/18 (2006.01)
- C12N 15/70 (2006.01)
- A61K 35/00 (2006.01)
- C12N 9/00 (2006.01)

(52) U.S. Cl.
CPC ......... *C12P 17/181* (2013.01); *A61K 2035/11* (2013.01); *Y02P 20/52* (2015.11)

(56) References Cited

U.S. PATENT DOCUMENTS

| | | | |
|---|---|---|---|
| 4,777,160 | A | 10/1988 | Oka et al. |
| 4,789,731 | A | 12/1988 | Oka et al. |
| 4,833,076 | A | 5/1989 | Konishi et al. |
| 6,355,412 | B1 | 3/2002 | Stewart et al. |
| 6,357,495 | B1 | 3/2002 | Baroncini |
| 6,509,156 | B1 | 1/2003 | Stewart et al. |

FOREIGN PATENT DOCUMENTS

| | | |
|---|---|---|
| WO | WO 99/29837 | 6/1999 |
| WO | WO 02/062988 | 8/2002 |
| WO | WO 03/010322 | 2/2003 |
| WO | WO 2007/128838 | 11/2007 |
| WO | WO 2008/098199 | 8/2008 |

OTHER PUBLICATIONS

DSM-7029 (last viwed on Sep. 20, 2016).*

Abril et al., "Regulator and enzyme specificities of the TOL plasmid-encoded upper pathway for degradation of aromatic hydrocarbons and expansion of the substrate range of the pathway", J. Bacteriol., Dec. 1989, 171(12), 6782-6790.

Agrawal et al., "Bacteriolytic therapy can generate a potent immune response against experimental tumors", PNAS, 2004, 101(42), 15172-15177.

Altenhoefer,"The probiotic *Escherichia coli* strain Nissle 1917 interferes with invasion of human intestinal epithelial cells by different enteroinvasive bacterial pathogens", FEMS Immunol Med Microbiol., 2004, 40(3), 223-229.

Amrein, "Functional analysis of genes involved in the synthesis of syringolin A by Pseudomonas syringae pv. syringae B301D-R", Mol. Plant Microbe Interact, 2004, 17, 90-97.

Belofsky et al., A New Cytotoxic Cyclic Depsipeptide Produced by a Marine Fungus of the Genus Fusarium. Tetrahedron Letters, 1999, 40, 2913-2916.

Binns et al., "Cell biology of Agrobacterium infection and transformation of plants", Annual Review of Microbiology, 1988, 42, 575-606.

Boddy et al., "Precursor-Directed Biosynthesis of Epothilone in *Escherichia coli*", J. Am. Chem. Soc., 2004, 126, 7436-7437.

Brown et al., The unique physiology of solid tumors: opportunities (and problems) for cancer therapy. Cancer Res., 1998, 58, 1408-16.

Carroll et al., "Synthesis and cytotoxicity of novel sansalvamide A derivatives", Org Lett., 2005, 7(16), 3481-3484.

Clark et al., "Genes of the RecE and RecF pathways of conjugational recombination in *Escherichia Coli*", Symp. Quant. Biol., 1984, 49, 453-462.

Coleman et al., "A new plant elicitor from the phytopathogenic bacterium Pseudomonas syringae pv. Syringae, inhibits the proliferation of neuroblastoma and ovarian cancer cells and induces apoptosis", Cell Prolif., 2006, 39, 599-609.

Ditta et al., "Broad host range DNA cloning system for gram-negative bacteria: construction of a gene bank of Rhizobium meliloti", Proc Natl Acad Sci., 1980, 77, 7347-7351.

Fisher et al., "Evaluation of the worth of corynebacterium parvum in conjunction with chemotherapy as adjuvant treatment for primary breast cancer. Eight-year results from the National Surgical Adjuvant Breast and Bowel Project B-10", Cancer, 1990, 66(2), 220-227.

Frary et al., "Efficiency and stability of high molecular weight DNA transformation: an analysis in tomato", Transgenic Res., 2001, 10, 121-132.

Fu et al., "Efficient transfer of two large secondary metabolite pathway gene clusters into heterologous hosts by transposition", Nucleic Acids Res., 2008, 36, e113.

Gerth et al., "Epothilons A and B: antifungal and cytotoxic compounds from Sorangium cellulosum (Myxobacteria)" Production, physico-chemical and biological properties. J Antibiot., 1996, 49(6), 560-563.

Gross et al., "Metabolic engineering of Pseudomonas putida for methylmalonyl-CoA biosynthesis to enable complex heterologous secondary metabolite formation", Chem. Biol., 2006, 13, 1-13.

Gust et al., "PCR- targeted Streptomyces gene replacement identifies a protein domain needed for biosynthesis of the sesquiterpene soil odor geosmin", PNAS, 2003, 100, 1541-1546.

Hamilton et al., "Stable transfer of intact high molecular weight DNA into plant chromosome", Proc.Natl. Acad. Sci., 1996, 93, 9975-9979.

Hamilton, "A binary-BAC system for plant transformation with high-molecular-weight DNA", Gene, 1997, 200, 107-116.

Hablinger et al., "Novel keto acid formate-lyase and propionate kinase enzymes are components of an anaerobic pathway in *Escherichia coli* that degrades L-threonine to propionate", Mol Microbiol., 1998, 27(2), 477-492.

Homburg et al., "Expression analysis of the colibactin gene cluster coding for a novel polyketide in *Escherichia coli*", FEMS Microbiol Lett., 2007, 275(2), 255-262.

Jia et al., "Enhanced therapeutic effect by combination of tumor-targeting Salmonella and endostatin in murine melanoma model", Cancer Biol Ther., 2005, 4(8), 840-845.

Kang et al., "One step engineering of T7-expression strains for protein production: increasing the host-range of the T7-expression system", Protein Expr. Purif., 2007, 55, 325-333.

Kealey et al., "Production of a polyketide natural product in nonpolyketide-producing prokaryotic and eukaryotic hosts", PNAS, 1998, 95, 505-509.

Kohwi et al., "Antitumor effect of Bifidobacterium infantis in mice", Gann, 1978, 69, 613-618.

Lee et al., "Endostatin gene therapy delivered by Salmonella choleraesuis in murine tumor models", J. Gene Med., 2004, 6(12), 1382-1393.

Lee et al., "Systemic administration of attenuated Salmonella choleraesuis carrying thrombospondin-1 gene leads to tumor-specific transgene expression, delayed tumor growth and prolonged survival in the murine melanoma model", Cancer Gene Ther., 2005, 12(2), 175-184.

Lodinová-Zadniková et al., "Effect of preventive administration of a nonpathogenic *Escherichia coli* strain on the colonization of the intestine with microbial pathogens in newborn infants", Biol Neonate., 1997, 71(4), 224-232.

Loeffler et al., "Attenuated Salmonella engineered to produce human cytokine LIGHT inhibit tumor growth", Proc Natl Acad Sci., 2007, 104(31), 12879-12883.

Low et al., "Lipid A mutant Salmonella with suppressed virulence and TNFa induction retain tumor-targeting in vivo", Nat Biotechnol., 1999, 17, 37-41.

Malmgren et al., "Localization of the vegetative form of Clostridium tetani in mouse tumors following intravenous spore administration", Cancer Res., 1955, 15(7), 473-478.

Matthysse et al., "Initial interactions of Agrobacterium tumefaciens with plant host cells", Critical Reviews in Microbiology, 1986, 13, 281-307.

Mersereau et al., "Efficient transformation of Agrobacterium tumefaciens by electroporation", Gene, 1990, 90, 149-151.

Michel et al., "Transcriptional changes in powdery mildew infected wheat and Arabidopsis leaves undergoing syringolin triggered hypersensitive cell death at infection sites", Plant Mol Biol., 2006, 62, 561-578.

(56) References Cited

OTHER PUBLICATIONS

Moese et al., "Oncolysis by clostridia. I. Activity of Clostridium butyricum (m-55) and other non-pathogenic clostridia against the ehrlich carcinoma", Cancer Res., 1964, 24, 212-216.
Mutka et al., Heterologous production of epothilone C and D in *Escherichia coli*. Biochemistry, 2006, 45, 1321-30.
Muyrers et al., "ET-Cloning: Think Recombination First", Genetic Eng., 2000, 22, 77-98.
Muyrers et al., "Point mutation of bacterial artificial chromosomes by ET recombination", EMBO Reports, 2000, 1, 239-243.
Muyrers et al., "Rapid modification of bacterial artificial chromosomes by ET-recombination", Nucleic Acid Res., 1999, 27, 1555-1557.
Muyrers et al., "RecE/RecT and Redα/Redβ initiate double-stranded break repair by specifically interacting with their respective partners", Genes Dev., 2000, 14 1971-1982.
Muyrers et al., "Techniques: Recombinogenic engineering-new options for cloning and manipulating DNA", Trends in Biochem. Sci., 2001, 26, 325-31.
Narayanan et al., "Efficient and precise engineering of a 200 kb β-globin human/bacterial artificial chromosome in *E. coli* DH10B using an inducible homologous recombination system", Gene Therapy, 1999, 6, 442-447.
Nester et al., "Crown gall: a molecular and physiological analysis", Annual Review of Plant Physiology, 1984, 35, 387-413.
Newman et al., "Broad-host-range expression vectors that carry the L-arabinose-inducible *Escherichia coli* araBAD promoter and the araC regulator", Gene, 1999, 227, 197-203.
Nougayréde et al., "*Escherichia coli* induces DNA double-strand breaks in eukaryotic cells", Science, 2006, 313(5788), 848-851.
Oka et al., "Glidobactins A, B and C, new antitumor antibiotics. I. Production, isolation, chemical properties and biological activity", J. Antibiot., 1988, 41, 1331-1337.
Oka et al., "Glidobactins A, B and C, new antitumor antibiotics. II. Structure elucidation", J. Antibiot., 41, 1988, 1338-1350.
Oka et al., "Glidobactins D, E, F, G and H; minor components of the antitumor antibiotic glidobactin", J. Antibiot., 1988, 41, 1906-1909.
Parker et al., "Effect of histolyticus infection and toxin on transplantable mouse tumors", Proc Soc Exp Biol Med., 1947, 66(2), 461-467.
Pawelek et al., "Bacteria as tumour-targeting vectors", Lancet Oncol., 2003, 4(9), 548-556.
Pawelek et al., "*Salmonella* pathogenicity island-2 and anticancer activity in mice", Cancer Gene Ther., 2002, 9(10), 813-818.
Pawelek et al., Tumor-targeted *Salmonella* as a novel anticancer vector. Cancer Res., 1997, 57(20), 4537-4544.
Pawelek, "Tumour-cell fusion as a source of myeloid traits in cancer", Lancet Oncol., 2005, 6(12), 988-993.
Perlova et al., "Reconstitution of the myxothiazol biosynthetic gene cluster by Red/ET recombination and heterologous expression in Myxococcus xanthus", Appl Environ Microbiol., 2006, 72, 7485-7494.
Pfeifer et al., "Biosynthesis of complex polyketides in a metabolically engineered strain of *E. coli*", Science, 2001, 291, 1790-1792.
Putze et al., "Genetic structure and distribution of the colibactin genomic island among members of the family Enterobacteriaceae", Infect Immun., Aug. 31, 2009, 77(11), 4696-4703.
Rembacken et al., "Non-pathogenic *Escherichia coli* versus mesalazine for the treatment of ulcerative colitis: a randomised trial. Lancet", Aug. 21, 1999, 354(9179), 635-639.
Rondon et al., "Identification and analysis of a siderophore biosynthetic gene cluster from Agrobacterium tumefaciens C58", Microbiol., 2004, 150(Pt 11), 3857-66.
Schneiker et al., "Complete genome sequence of the myxobacterium Sorangium cellulosum", Nat Biotechnol., 2007, 25, 1281-1289.
Shoji et al., "Isolation of cepafungins I, II and III from *Pseudomonas* species", J Antibiot., 1990, 43, 783-787.

Silakowski et al., "New lessons for combinatorial biosynthesis from myxobacteria. The myxothiazol biosynthetic gene cluster of Stigmatella aurantiaca DW4/3-1", J Biol Chem., 1999, 274(52), 37391-37399.
Smith et al., "A plant tumour of bacterial origin", Science, 1907, 25, 671-673.
Stritzker et al., "Tumor-specific colonization, tissue distribution, and gene induction by probiotic *Escherichia coli* Nissle 1917 in live mice", Int J Med Microbiol., Apr. 2007, 297(3), 151-162.
Sznol, "Use of preferentially replicating bacteria for the treatment of cancer", J Clin Invest., 2000, 105, 1027-1030.
Tang et al., "Cloning and heterologous expression of the epothilone gene cluster", Science, 2000, 287, 640-642.
Van Dyk et al., "Involvement of ack-pta operon products in alpha-ketobutyrate metabolism by *Salmonella typhimurium*", Mol Gen Genet., 1987, 207(2-3), 435-40.
Vlasák et al., "Construction and use of Agrobacterium tumefaciens binary vectors with A. tumefaciens C58 T-DNA genes", Folia Microbiol., 1992, 37, 227-230.
Wäspi et al., "Identification and structure of a family of syringolin variants: unusual cyclic peptides from Pseudomonas syringae pv. syringae that elicit defense responses in rice", Microbiol Res., 1999, 154, 89-93.
Wäspi et al., Syringolin reprograms wheat to undergo hypersensitive cell death in a compatible interaction with powdery mildew. Plant Cell, 2001, 13, 153-161.
Wäspi et al., "Syringolin, a novel peptide elicitor from Pseudomonas syringae pv. syringae that induces resistance to Pyricularia oryzae in rice", Mol Plant Microbe Interact., 1998, 11, 727-733.
Xiang et al., "Short hairpin RNA-expressing bacteria elicit RNA interference in mammals", Nature Biotechnology, 2006, 24, 1-6.
Yi et al., "Antitumor effect of cytosine deaminase/5-fluorocytosine suicide gene therapy system mediated by Bifidobacterium infantis on melanoma", Acta Pharmacol Sin., 2005, 26(5), 629-634.
Yu et al., "Transforming growth factor-beta facilitates breast carcinoma metastasis by promoting tumor cell survival", Clin Exp Metastasis, 2004, 21(3), 235-242.
Zhang et al., A new logic for DNA engineering using recombination in *Escherichia coli*, Nat. Genet., 1998, 20, 123-128.
Zhang et al., "DNA cloning by homologous recombination in *Escherichia coli*", Nature Biotechnology, 2000, 18, 1314-1317.
Zhang et al., Phage annealing proteins promote oligonucleotide-directed mutagenesis in *Escherichia coli* and mouse ES cells, BMC Mol Biol., Jan. 16, 2003, 4(1), 1-14.
Zhao et al., "Targeted therapy with a *Salmonella typhimurium* leucine-arginine auxotroph cures orthotopic human breast tumors in nude mice", Cancer Res., 2006, 66(15), 7647-7652.
Zhao et al., "Tumor-targeting bacterial therapy with amino acid auxotrophs of GFPexpressing *Salmonella typhimurium*", Proc Natl Acad Sci., 2005, 102(3), 755-760.
Gaitatzis et al., "The mtaA Gene of the Myxothiazol Biosynthetic Gene Cluster From Stigmatella Aurantiaca DW4/3-1 Encodes a Phosphopantetheinyl Transferase That Activates Polyketide Synthases and Polypeptide Synthetases", J. of Biochem., Jan. 2001, 129(1), 119-124.
Julien et al., "Heterologous Expression of Epothilone Biosynthetic Genes in Myxococcus Xanthus", Antimicrobial Agents and Chemotherapy, Sep. 2002, 46(9), 2772-2778.
Long et al., "Combination Bacteriolytic Therapy for the Treatment of Experimental Tumors", PNAS, 2001, 98, 15155-15160.
Patzer et al., "The Colicin G, H, X, Determinants Encode Microcins M and H47, Which Might Utilize the Catecholate Siderophore Receptors FepA, Cir, Fiu and IroN", Microbiology, Sep. 2003, 149(9), 2557-2570.
Perlova et al., "Novel Expression Hosts for Complex Secondary Metabolite Megasynthetases: Production of Myxochromide in the Thermopilic Isolate Coralloccus Macrosporus GT-2", Microbial Cell Factories, Jan. 2009, 8(1), p. 1.
Schellenberg et al., "Identification of Genes Involved in the Biosynthesis of the Cytoxic Compound Glidobactin from a Soil Bacterium", Environmental Microbiology, Jul. 2007, 9(7), 1640-1650.

(56) References Cited

OTHER PUBLICATIONS

Wenzel et al., "Heterologous Expression of a Myxobacterial Natural Products Assembly Line in Pseudomonads via Red/Et Recombineering", Chemistry and Biology, Mar. 2005, 12(3), 349-356.

* cited by examiner

1 – PBS control; 2 – E.coli Nissle 1917 control; 3 – E.coli Nissle 1917 with pSUMtaA clone 1; 4 - E.coli Nissle 1917 with pSUMtaA clone 2

1 – PBS control; 2 - *E. coli* Nissle 1917 original strain; 3 - *E. coli* Nissle 1917 with colinbatin deletion; 4 - *E. coli* Nissle 1917 with cm in front of endogenous pPant transferase 1 - LB medium alone
2 - E. coli K12 (GB2005) + pSUMtaA
3 - E. coli Nissle 1917 + pACYC184
4 - E. coli Nissle 1917 + pSUMtaA clone1
5 - E. coli Nissle 1917 + pSUMtaA clone2
6 - E. coli Nissle 1917 clb deletion + pSUMtaA Glidiobactin detection

SEQUENCE LISTING

```
<160> NUMBER OF SEQ ID NOS: 26

<210> SEQ ID NO 1
<211> LENGTH: 1299
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Partial sequence of 16S rRNA gene of DSM7029
      wildtype

<400> SEQUENCE: 1
cccttatgac tacttgttac gacttcaccc cagtcacgaa ccctgccgtg gtgatcgccc      60
tccttgcggt taggctaacc acttctggca gaacccgctc ccatggtgtg acgggcggtg     120
```

-continued

```
tgtacaagac ccgggaacgt attcaccgcg gcatgctgat ccgcgattac tagcgattcc      180
gacttcacgc agtcgagttg cagactgcga tccggactac gaccggtttt ctgggattag      240
ctccccctcg cgggttggca gccctctgta ccggccattg tatgacgtgt gtagccctac      300
ccataagggc catgatgacc tgacgtcatc cccaccttcc tccggtttgt caccggcagt      360
ctcattagag tgccctttcg tagcaactaa tgacaagggt tgcgctcgtt gcgggactta      420
acccaacatc tcacgacacg agctgacgac ggccatgcag cacctgtgtc caggttctct      480
ttcgagcact cccacatctc tgcaggattc ctggcatgtc aagggtaggt aaggttttc      540 gcgttgcatc gaattaaacc acatcatcca ccgcttgtgc gggtccccgt caattccttt      600
gagtttcaac cttgcggccg tactccccag gcggtcaact tcacgcgtta gcttcgttac      660
tgaacagcaa gccgtccaac aactagttga catcgtttag ggcgtggact accagggtat      720
ctaatcctgt ttgctcccca cgctttcgtg catgagcgtc agtgcaggcc caggagattg      780
ccttcgccat cggtgttcct ccgcatatct acgcatttca ctgctacacg cggaattcca      840
tctccctctg ccgcactcta gccgtgcagt cacaaatgca gttcccaggt tgagcccggg      900
gatttcacat ctgtcttgca caaccgcctg cgcacgcttt acgcccagta attccgatta      960
acgctcgcac cctacgtatt accgcggctg ctggcacgta gttaggcggg tgcttattct     1020
tcaggtaccg tcatcggctc cggggtatag cccagaactt ttcttccctg acaaaagcgg     1080
tttacacccg gacgtcttct tcccgcacgc ggcatggctg gatcaggctg cgccatggtc     1140
aaaactcccc actgctgcct ccgtaggagt ctggcgtgtc ctcagtccca ggtgtggctt     1200
gtcgtcctct cagacagcta cgatcgtcgc atgtagctac ccacacacta gctaatctga     1260
ctcgggcgat caaataggcg cgagccttgg caattctgt                            1299
```

<210> SEQ ID NO 2
<211> LENGTH: 1300
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Partial sequence of 16S rRNA gene of DSM7029 Kan1

<400> SEQUENCE: 2

```
tcgtaattgc tcattgttac gacttcaccc cagtcacgaa ccctgccgtg gtgatcgccc       60
tccttgcggt taggctaacc acttctggca gaacccgctc ccatggtgtg acgggcggtg      120
tgtacaagac ccgggaacgt attcaccgcg gcatgctgat ccgcgattac tagcgattcc      180
gacttcacgc agtcgagttg cagactgcga tccggactac gaccggtttt ctgggattag      240
ctccccctcg cgggttggca gccctctgta ccggccattg tatgacgtgt gtagccctac      300
ccataagggc catgatgacc tgacgtcatc cccaccttcc tccggtttgt caccggcagt      360
ctcattagag tgccctttcg tagcaactaa tgacaagggt tgcgctcgtt gcgggactta      420
acccaacatc tcacgacacg agctgacgac ggccatgcag cacctgtgtc caggttctct      480
ttcgagcact cccacatctc tgcaggattc ctggcatgtc aagggtaggt aaggttttc      540 gcgttgcatc gaattaaacc acatcatcca ccgcttgtgc gggtccccgt caattccttt      600
gagtttcaac cttgcggccg tactccccag gcggtcaact tcacgcgtta gcttcgttac      660
tgaacagcaa gccgtccaac aactagttga catcgtttag ggcgtggact accagggtat      720
ctaatcctgt ttgctcccca cgctttcgtg catgagcgtc agtgcaggcc caggagattg      780
```

-continued

```
ccttcgccat cggtgttcct ccgcatatct acgcatttca ctgctacacg cggaattcca      840
tctctctctg ccgcactcta gccgtgcagt cacaaatgca gttcccaggt tgagcccggg      900
gatttcacat ctgtcttgca caaccgcctg cgcacgcttt acgcccagta tttccgatta      960
acgctcgcac cctacgtatt accgcggctg ctggcacgta gttagccggt gcttattctt     1020
caggtaccgt catcgctccg ggggtattag cccagatctt ttcttccctg acaaagcggt     1080
ttacacccgg acgtcttctt ccggcacggc ggcatggctg atcaggctt gcgccgatga      1140 tccaaactcc ccactgctgc ctcagtagga gtctggggcc gtgtctcagt cccagggtgg     1200
ctgtcgtcct ctcgactagc tacgaatcgc tcgcttgtag cataccacca actagctaat    1260
ctgacatcga cgttcattag gcgggaggct gtggcaaatc                           1300
```

<210> SEQ ID NO 3
<211> LENGTH: 834
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Coding sequence of MtaA gene

<400> SEQUENCE: 3

```
atgccgacgt cctccctgc gctgcccttg ttgaagttgc caccagacga agtccatgtc       60
tggatcgtcg agcccgagcg catcaccgag ccagggctgc tggagtccta ccgcgccctg     120
ctggacccag gggagcgcga caaacagcag cggttctact tcgagaggca ccggctgcag     180
tacctcgtct ctcatgcgct cgtgcggctc accttgtcgc gctatgcgcc cgtggcgccc     240
gaggcctggt ccttctccgc caaccagtac ggccggccgg agatccgggg tgaggagaaa    300
ccgtggttgc gtttcaacct ctcccacacg gatgggatgg ccctctgcgc ggtggcccgc     360
gatgtggatg tgggagccga tgtggaggac accgagcgga gaggggaaac ggtggagatc    420
gccgacagct ttttcgcccc cgccgaggtg gcctcgcttc gggcactccc ggtgagtggc    480
cagcgcgagc gcttcttttga ttattggacc ttgaaggagg cctacatcaa ggcgcgtgga    540
atggggcttt ccctgcccct tggaccagtt gccttcgagg tttcgcaggg gctttccacc   600
cggatttcct ttgatccgcg tctggtggac gagccctctc agtggcagtt cgtacggttc     660
cggccctccc agcggcacgc cgccgcgctg gctgtgcgcc gccctcgga ggccccctc      720 acggtgcggt ttcagcgcac cgttccgctc caggatgatg cacctgcgga gtatctctca    780
cgagagcgga tccagccgct gcgcctccgg atgcccgggg tgggaggagg gtga          834
```

<210> SEQ ID NO 4
<211> LENGTH: 277
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Protein sequence of MtaA

<400> SEQUENCE: 4

```
Met Pro Thr Ser Ser Pro Ala Leu Pro Leu Leu Lys Leu Pro Pro Asp
1               5                   10                  15

Glu Val His Val Trp Ile Val Glu Pro Glu Arg Ile Thr Glu Pro Gly
            20                  25                  30
```

Leu Leu Glu Ser Tyr Arg Ala Leu Leu Asp Pro Gly Glu Arg Asp Lys
                35                  40                  45

Gln Gln Arg Phe Tyr Phe Glu Arg His Arg Leu Gln Tyr Leu Val Ser
        50                  55                  60

His Ala Leu Val Arg Leu Thr Leu Ser Arg Tyr Ala Pro Val Ala Pro
65                  70                  75                  80

Glu Ala Trp Ser Phe Ser Ala Asn Gln Tyr Gly Arg Pro Glu Ile Arg
                85                  90                  95

Gly Glu Glu Lys Pro Trp Leu Arg Phe Asn Leu Ser His Thr Asp Gly
            100                 105                 110

Met Ala Leu Cys Ala Val Ala Arg Asp Val Asp Val Gly Ala Asp Val
            115                 120                 125

Glu Asp Thr Glu Arg Arg Gly Glu Thr Val Glu Ile Ala Asp Ser Phe
130                 135                 140

Phe Ala Pro Ala Glu Val Ala Ser Leu Arg Ala Leu Pro Val Ser Gly
145                 150                 155                 160

Gln Arg Glu Arg Phe Phe Asp Tyr Trp Thr Leu Lys Glu Ala Tyr Ile
                165                 170                 175

Lys Ala Arg Gly Met Gly Leu Ser Leu Pro Leu Asp Gln Phe Ala Phe
            180                 185                 190

Glu Val Ser Gln Gly Leu Ser Thr Arg Ile Ser Phe Asp Pro Arg Leu
            195                 200                 205

Val Asp Glu Pro Ser Gln Trp Gln Phe Val Arg Phe Arg Pro Ser Gln
210                 215                 220

Arg His Ala Ala Ala Leu Ala Val Arg Arg Pro Ser Glu Ala Pro Leu
225                 230                 235                 240

Thr Val Arg Phe Gln Arg Thr Val Pro Leu Gln Asp Asp Ala Pro Ala
                245                 250                 255

Glu Tyr Leu Ser Arg Glu Arg Ile Gln Pro Leu Arg Leu Arg Met Pro
            260                 265                 270

Gly Val Gly Gly Gly
            275

<210> SEQ ID NO 5
<211> LENGTH: 101
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: DSM7029

<400> SEQUENCE: 5
gtcgagttgc agactgcgat ccggactacg accggttttc tgggattagc tcccctcgc      60 gggttggcag ccctctgtac cggccattgt atgacgtgtg t                        101

<210> SEQ ID NO 6
<211> LENGTH: 138
<212> TYPE: DNA
<213> ORGANISM: Anaeromyxobacter dehalogenans
<220> FEATURE:
<223> OTHER INFORMATION: Strain 2CP-1

<400> SEQUENCE: 6
accaaggcaa cgacgggtag ctggtctgag aggacgatca gccacactgg aactgagaca    60
cggtccagac tcctacggga ggcagcagtg gggaatcttg cgcaatgggc gaaagcctga   120
cgcagcaacg ccgcgtgt                                                 138

<210> SEQ ID NO 7
<211> LENGTH: 138
<212> TYPE: DNA
<213> ORGANISM: Corallococcus coralloides
<220> FEATURE:
<223> OTHER INFORMATION: Strain Cc9736

<400> SEQUENCE: 7
accaaggcga cgacgggtag ctggtctgag aggacgatca gccacactgg aactgagaca    60
cggtccagac tcctacggga ggcagcagtg gggaattttg cgcaatgggc gaaagcctga   120
cgcagcaacg ccgcgtgt                                                 138

<210> SEQ ID NO 8
<211> LENGTH: 137
<212> TYPE: DNA
<213> ORGANISM: Myxobacterium KC

<400> SEQUENCE: 8
accaaggcaa cgacgggtag ctggtctgag aggacgatca gccacactgg aactgagaca    60
cggtccagac tctacgggag gcagcagtgg ggaatcttgc gcaatgggcg aaagcctgac   120
gcagcaacgc cgcgtgt                                                  137

<210> SEQ ID NO 9
<211> LENGTH: 138
<212> TYPE: DNA
<213> ORGANISM: Myxobacterium SHI-1

<400> SEQUENCE: 9
accaaggcta agacgggtag ctggtctgag aggatgatca gccacactgg aactgagaca    60
cggtccagac tcctacggga ggcagcagtg gggaatattg cgcaatgggc gaaagcctga   120
cgcagccacg ccgcgtgt                                                 138

<210> SEQ ID NO 10
<211> LENGTH: 138
<212> TYPE: DNA
<213> ORGANISM: Myxobacterium SMH-27-4

<400> SEQUENCE: 10
accaaggcta agacgggtag ctggtctgag aggatgatca gccacactgg aactgagaca    60
cggtccagac tcctacggga ggcagcagtg gggaatattg cgcaatgggc gaaagcctga   120
cgcagccacg ccgcgtgt                                                 138

<210> SEQ ID NO 11
<211> LENGTH: 138
<212> TYPE: DNA
<213> ORGANISM: Polyangium cellulosum
<220> FEATURE:
<223> OTHER INFORMATION: So ce56

-continued

```
<400> SEQUENCE: 11
accaaggcga agacgggtag ctggtctgag aggatgatca gccacactgg aactgagaca    60
cggtccagac tcctacggaa ggcagcagtg gggaatcttg cgcaatgggc gaaagcctga   120
cgcagcgacg ccgcgtgt                                                 138

<210> SEQ ID NO 12
<211> LENGTH: 138
<212> TYPE: DNA
<213> ORGANISM: Polyangium cellulosum
<220> FEATURE:
<223> OTHER INFORMATION: So ce90

<400> SEQUENCE: 12
accaaggcga agacgggtag ctggtctgag aggatgatca gccacactgg aactgagaca    60
cggtccagac tcctacggga ggcagcagtg gggaatcttg cgcaatgggc gaaagcctga   120
cgcagcgacg ccgcgtgt                                                 138

<210> SEQ ID NO 13
<211> LENGTH: 138
<212> TYPE: DNA
<213> ORGANISM: Polyangium cellulosum
<220> FEATURE:
<223> OTHER INFORMATION: So0089-1

<400> SEQUENCE: 13
accaaggcga agacgggtag ctggtctgag aggatgatca gccacactgg aactgagaca    60
cggtccagac tcctacggga ggcagcagtg gggaatcttg cgcaatgggc gaaagcctga   120
cgcagcgacg ccgcgtgt                                                 138

<210> SEQ ID NO 14
<211> LENGTH: 119
<212> TYPE: DNA
<213> ORGANISM: Burkholderia mallei
<220> FEATURE:
<223> OTHER INFORMATION: Strain NTCT 10260

<400> SEQUENCE: 14
gcgttgcatc gaattaatcc acatcatcca ccgcttgtgc gggtccccgt caattccttt    60
gagttttaat cttgcgaccg tactccccag gcggtcaact tcacgcgtta gctacgtta   119

<210> SEQ ID NO 15
<211> LENGTH: 119
<212> TYPE: DNA
<213> ORGANISM: Burkholderia pseudomallei
<220> FEATURE:
<223> OTHER INFORMATION: BCC215

<400> SEQUENCE: 15
gcgttgcatc gaattaatcc acatcatcca ccgcttgtgc gggtccccgt caattccttt    60
gagttttaat cttgcgaccg tactccccag gcggtcaact tcacgcgtta gctacgtta   119

<210> SEQ ID NO 16
<211> LENGTH: 119
<212> TYPE: DNA
<213> ORGANISM: Burkholderia gladioli
<220> FEATURE:
<223> OTHER INFORMATION: Strain R1879
```

<400> SEQUENCE: 16
gcgttgcatc gaattaatcc acatcatcca ccgcttgtgc gggtccccgt caattccttt      60
gagttttaat cttgcgaccg tactccccag gcggtcaact tcacgcgtta gccacgtta     119

<210> SEQ ID NO 17
<211> LENGTH: 119
<212> TYPE: DNA
<213> ORGANISM: Burkholderia gladioli
<220> FEATURE:
<223> OTHER INFORMATION: Strain R406

<400> SEQUENCE: 17
gcgttgcatc gaattaatcc acatcatcca ccgcttgtgc gggtccccgt caattccttt      60
gagttttaat cttgcgaccg tactccccag gcggtcaact tcacgcgtta gctacgtta     119

<210> SEQ ID NO 18
<211> LENGTH: 119
<212> TYPE: DNA
<213> ORGANISM: Burkholderia mallei
<220> FEATURE:
<223> OTHER INFORMATION: DSM7029

<400> SEQUENCE: 18
gcgttgcatc gaattaaacc acatcatcca ccgcttgtgc gggtccccgt caattccttt      60
gagtttcaac cttgcggccg tactccccag gcggtcaact tcacgcgtta gcttcgtta     119

<210> SEQ ID NO 19
<211> LENGTH: 119
<212> TYPE: DNA
<213> ORGANISM: Burkholderia mallei
<220> FEATURE:
<223> OTHER INFORMATION: Strain ATCC 23344

<400> SEQUENCE: 19
gcgttgcatc gaattaatcc acatcatcca ccgcttgtgc gggtccccgt caattccttt      60
gagttttaat cttgcgaccg tactccccag gcggtcaact tcacgcgtta gctacgtta     119

<210> SEQ ID NO 20
<211> LENGTH: 119
<212> TYPE: DNA
<213> ORGANISM: Burkholderia mallei
<220> FEATURE:
<223> OTHER INFORMATION: Strain NCTC 10260

<400> SEQUENCE: 20
gcgttgcatc gaattaatcc acatcatcca ccgcttgtgc gggtccccgt caattccttt      60
gagttttaat cttgcgaccg tactccccag gcggtcaact tcacgcgtta gctacgtta     119

<210> SEQ ID NO 21
<211> LENGTH: 119
<212> TYPE: DNA
<213> ORGANISM: Burkholderia mallei
<220> FEATURE:
<223> OTHER INFORMATION: Strain 2000031063

<400> SEQUENCE: 21
gcgttgcatc gaattaatcc acatcatcca ccgcttgtgc gggtccccgt caattccttt      60
gagttttaat cttgcgaccg tactccccag gcggtcaact tcacgcgtta gctacgtta     119

```
<210> SEQ ID NO 22
<211> LENGTH: 119
<212> TYPE: DNA
<213> ORGANISM: Burkholderia cepacia
<220> FEATURE:
<223> OTHER INFORMATION: Strain 2Pe38

<400> SEQUENCE: 22
gcgttgcatc gaattaatcc acatcatcca ccgcttgtgc gggtccccgt caattccttt      60 gagtttaat cttgcgaccg tactccccag gcggtcaact tcacgcgtta gctacgtta      119

<210> SEQ ID NO 23
<211> LENGTH: 119
<212> TYPE: DNA
<213> ORGANISM: Burkholderia cepacia
<220> FEATURE:
<223> OTHER INFORMATION: Strain 1=3b

<400> SEQUENCE: 23
gcgttgcatc gaattaatcc acatcatcca ccgcttgtgc gggtccccgt caattccttt      60 gagtttaat cttgcgaccg tactccccag gcggtcaact tcacgcgtta gctacgtta      119

<210> SEQ ID NO 24
<211> LENGTH: 119
<212> TYPE: DNA
<213> ORGANISM: Burkholderia cepacia
<220> FEATURE:
<223> OTHER INFORMATION: Strain ESR87

<400> SEQUENCE: 24
gcgttgcatc gaattaatcc acatcatcca ccgcttgtgc gggtccccgt caattccttt      60 gagtttaat cttgcgaccg tactccccag gcggtcaact tcacgcgtta gctacgtta      119

<210> SEQ ID NO 25
<211> LENGTH: 119
<212> TYPE: DNA
<213> ORGANISM: Burkholderia cepacia
<220> FEATURE:
<223> OTHER INFORMATION: Strain NE9

<400> SEQUENCE: 25
gcgttgcatc gaattaatcc acatcatcca ccgcttgtgc gggtccccgt caattccttt      60 gagtttaat cttgcgaccg tactccccag gcggtcaact tcacgcgtta gctacgtta      119

<210> SEQ ID NO 26
<211> LENGTH: 119
<212> TYPE: DNA
<213> ORGANISM: Burkholderia mallei
<220> FEATURE:
<223> OTHER INFORMATION: Strain AE9

<400> SEQUENCE: 26
gcgttgcatc gaattaatcc acatcatcca ccgcttgtgc gggtccccgt caattccttt      60 gagtttaat cttgcgaccg tactccccag gcggtcaact tcacgcgtta gctacgtta      119
```

HETEROLOGOUS HOSTS

CROSS-REFERENCE TO RELATED APPLICATIONS

This application is the National Stage of International Patent Application No. PCT/IB2010/055923 filed Dec. 17, 2010, which claims the benefit of United Kingdom Patent Application No. 0922108.6, filed Dec. 17, 2009, the disclosures of which are incorporated herein by reference in their entireties.

SEQUENCE LISTING

The instant application contains a Sequence Listing which has been submitted in ASCII format via EFS-Web and is hereby incorporated by reference in its entirety. Said ASCII copy, created on Jun. 28, 2012, is named Sequence_ Listing_CRF_CARP0183 and is 14,446 bytes in size.

FIELD OF INVENTION

This invention is related to bacterial engineering and the heterologous expression of useful compounds.

All documents referred to herein are incorporated by reference in their entirety.

INTRODUCTION

Many secondary metabolites, including commercially important antibiotics and cytotoxins, are produced in diverse prokaryotes and eukaryotes from enzymatic pathways encoded by gene complexes, which are often found in a large, single, contiguous genomic region. Because the structure of the secondary metabolite product of a biosynthetic pathway is directed by the specificity of the enzymes along the pathway, mutagenesis of the genes encoding the enzymes is potentially an advantageous way to alter the chemical product. Hence, variations in secondary metabolites, formerly limited to the applied science of organic chemistry, can be achieved through the application of DNA mutagenesis to the genes of these pathways.

Whereas organic chemistry is limited to the modification of high energy bond sites on the secondary metabolite, DNA mutagenesis can theoretically alter every bond in a secondary metabolite. Therefore DNA mutagenesis presents exceptional promise for the alteration of existing, and the creation of new, secondary metabolites for drug optimization and discovery. However, DNA mutagenesis technology, which is highly developed for *E. coli*, is poorly developed for the diverse hosts of relevance to secondary metabolite production. At best, current in situ host-by-host approaches for mutagenesis of secondary metabolite pathways are limited to individual mutagenesis that is often labour intensive. In order to overcome the problems associated with the limited capacity of natural secondary metabolite producing hosts such as *Streptomycetes* for genetic manipulation, other heterologous hosts have been investigated. *E. coli* has been a preferred host cell as techniques for performing cloning and genetic manipulation in *E. coli* are well established in the art. For example, (Kealey et al., 1998) describes the production of the fungal polyketide 6-methylsalicylic acid (6-MSA) in heterologous *E. coli*, yeast and plant cells. Further, (Pfeifer et al., 2001) describes the genetic engineering of a derivative of *E. coli* in which the resulting cellular catalyst converts exogenous propionate into the polyketide erythromycin (6-deoxyerythronolide B). The use of *E. coli* for engineering coupled with *Streptomyces* as the expression host has been described by scientists at the John Innes Institute in Norwich (Gust et al., 2003).

However, the absence of certain precursor production pathways and enzymes required for biosynthesis limits the value of *E. coli* and the other heterologous host cells described in the art for heterologous expression of secondary metabolites. For example, *E. coli* lacks at least two activities required for most polyketide and non-ribosomal peptide (NRP) pathways. Whereas these activities can be introduced into *E. coli*, these engineered hosts produce only small amounts of the intended secondary metabolite. Furthermore, *E. coli* has a low GC genomic content, unlike the genomes of Actinomycetes and Myxobacteria, the major secondary metabolite producing hosts, which both have a high GC content. Thus, codon usage is not optimised in *E. coli* when a gene from these organisms is expressed.

There is a need for alternative and improved methods for heterologous expression which couple the advantages of fluent DNA mutagenesis and engineering whilst enabling good host properties for the production of secondary metabolites.

In addition, heterologous hosts are currently used for mutagenesis and synthesis of secondary metabolites, as discussed above. The provision of new heterologous hosts offers the possibility of using the hosts as drug delivery vectors, to target drug compounds directly to tissues.

SUMMARY OF INVENTION

The invention provides hosts that have been engineered for the heterologous expression of genes capable of polyketide or non-ribosomal protein synthesis as well as methods for generating such hosts. Accordingly, in one aspect the invention provides a host that has been engineered for heterologous expression of genes capable of polyketide or non-ribosomal peptide synthesis.

By "heterologous expression" is meant the expression of a gene in a host cell, where that gene is not normally expressed by the host cell. In particular, this concept is intended to represent the expression of genes transferred from a host cell which is a heterologous species with respect to the host cell into which the gene is transferred. Alternatively, the hosts may be engineered to express endogenous silent genes or gene clusters or activate normally silent or poorly transcribed genes; the term "heterologous expression" covers this scenario as this term is used herein. Many suitable hosts comprise gene clusters that have all or some of the genes necessary for the production of useful compounds such as polyketides and non-ribosomal peptides but which are normally not expressed. By engineering such hosts to activate silent genes or to introduce genes that are missing from a useful synthetic pathway, this invention provides methods for heterologous expression of useful compounds such as polyketides and non-ribosomal peptides.

In certain embodiments of the invention, the entire gene cluster required for expression of a polyketide or non-ribosomal peptide is heterologous to the host. The terms "gene cluster" is used herein to describe a group of genes in close proximity in a DNA molecule that are part of the same pathway. The genes may be found in nature in the gene cluster or the gene cluster may be engineered. The gene cluster may be complete and self-sufficient for a particular function or it may require other gene clusters or genes to be fully functional. By this it is meant either that the pathway itself, in the form contained on the vector, is not naturally known in the heterologous host cell, or that one or more of the genes that make up the pathway is not known in the heterologous host cell. Alternatively, a subset of the genes required for expression of a polyketide or non-ribosomal peptide is endogenous to the host and an additional heterologous subset of genes is transferred to the host.

Preferably, the secondary metabolite is not naturally produced in the heterologous host cell. The method of the invention allows the study of pathways that are completely unknown in either of the host cell systems that are used.

In preferred embodiments of the invention, the heterologous hosts are transformed with gene clusters selected from one or more of the following organisms; *Polyangium*, myxobacteria, *Soraggium cellulosum*, *Agrobacterium tumefaciens*, *E. coli* Nissle 1917, *Burkholderia* and *S. aurantiaca*.

According to the invention, the heterologous hosts are transformed with genes capable of polyketide or non-ribosomal peptide synthesis. As the skilled reader will understand, there are many genes capable of polyketide or non-ribosomal peptide synthesis. Examples include genes that form part of a polyketide pathway (preferably a type I polyketide pathway, but alternatively can be a type II or a type III polyketide), a non-ribosomal peptide (NRP) pathway or genes that form a pathway which combines enzymes from two or more of the pathways encoding these secondary metabolites, for example a hybrid polyketide-NRP. Particular examples include one or more genes or gene clusters selected from the following group; a PKS/NRPS gene cluster, glidobactin gene cluster, epothilone gene cluster, myxochromide S gene cluster, methylmalonyl CoA mutase, methylmalonyl CoA epimerase, myxothiazol gene cluster, propionyl-CoA carboxylase. Combinations of these genes and optionally other genes enable a large range of potential compounds to be synthesised. Furthermore, shuffling of these genes and gene clusters will allow the synthesis of a greater range of compounds and the generation of novel compounds.

Preferably, the genes of the biosynthetic pathway are transcribed under the control of promoters that are found naturally in the heterologous host cell. This allows the transcription machinery of the heterologous host cell to recognise its own promoters and thus transcribe the genes implicated in the metabolic pathway under study.

In an especially preferred embodiment, a gene capable of polyketide synthesis may include one or more, preferably all, members of a gene cluster that allows the heterologous expression of a PKS/NRPS metabolite. Preferred polyketides to be produced by the invention include glidobactin A, epothilone and myxochromide and related molecules and derivatives of such molecules. Examples of other useful metabolites include colibactin.

Glidobactin A has strong anti-fungal and anti-proliferative activity. Glidobactin A, which has antifungal activity, is cytotoxic to tumour cell lines and can prolong the lifespan of mice inoculated with P388 leukaemia cells (Oka et al., 1988a,b,c) (FIG. 1). Antibiotic compounds Cepafungin I, II and III, independently isolated from *Burkholderia cepacia* (Shoji et al., 1990), have been found to have similar structure to glidobactin A, B and C. Recently, glidobactin A was found to belong to a new class of proteasome inhibitors. As proteasome inhibitors are a promising class of anti-tumour agents, glidobactin A and its structurally modified derivatives may serve as new lead compounds for the development of novel anticancer drugs. Another related compound is epothilone (Gerth et al., 1996) which has gone through clinical trials and could quite possibly replace taxol as the most widely used anticancer drug. Further considered compounds are tubulysin and disorazol. Epothilone, tubulysin and disorazol are active at ng or pg levels. The invention paves the way for very significant possibilities for generating novel compounds with useful properties, such as anti-proliferative activities, through swapping the modules and domains of gene clusters encoding these compounds.

*Burkholderia* and *Burkholderia* DSM7029

In one embodiment of the invention, *Burkholderia* is used as a heterologous host for the expression of genes capable of polyketide or non-ribosomal peptide synthesis. In a preferred embodiment of the invention, the *Burkholderia* strain is DSM7029 (see www.dsmz.de/microorganisms/html/strains/strain.dsm007029.html; ATCC 53080, NBRC 100090, Oka M. et al. (1998) J. Antibiot. 41 p 1331-1337; Oka M. et al. (1998) J. Antibiot. 41p1338-1350).

The invention generally provides *Burkholderia* host cells that have been engineered for heterologous expression of such genes and methods for generating these hosts.

*Burkholderia* cells, and especially those of strain DSM7029, grow fast with a doubling time of one hour, in contrast to, for example, many species that are conventionally used to produce useful secondary metabolites, such as myxobacteria. Additionally, these bacteria can form single colonies on solid agar plates, leading to colonies that are visible in two days. In addition to the ease with which it can be cultured, *Burkholderia* and specifically DSM7029 are capable of producing useful compounds from their own genetic arsenal and so inventors consider that the potential for production of novel secondary metabolites through expression from heterologous genes is significant. For example, glidobactins are a family of related molecules that have been isolated from DSM7029 and have been shown to possess antifungal activity, to be cytotoxic to tumour cells and to prolong the life span of mice inoculated with P388 leukaemia cells. Antibiotic compounds Cepafungin I, II and III, independently isolated from *Burkholderia cepacia* (Shoji et al., 1990), have been found to have similar structure to glidobactin A, B and C. Given that *Burkholderia* and DSM7029 are inherently capable of expressing such useful PKS/NRPS compounds, it would appear that these strains already have at least some of the necessary genetic capability for producing such compounds. Accordingly, the inventors devised a strategy to test whether these host cells might possess potential for expression of similar compounds from heterologous gene constructs. It was their view that less genetic engineering may be required to generate *Burkholderia* capable of expressing polyketides and non ribosomal peptides.

However, *Burkholderia* are rarely used in genetic engineering and metabolite synthesis and there are few tools available for the handling and utilisation of *Burkholderia* cells. Despite this obstacle, through development of novel strategies for manipulation of these host cells, the inventors surprisingly identified that *Burkholderia* and especially DSM7029 actually represent ideal heterologous hosts for the expression of genes capable of polyketide or non-ribosomal peptide synthesis. Additionally, the inventors have provided novel methods for transforming *Burkholderia* that facilitate the transformation and resultant expression of heterologous genes in such hosts.

This invention additionally provides a method for transforming *Burkholderia* that can, for example, be used in generating *Burkholderia* hosts that are engineered for heterologous expression of genes capable of polyketide or non-ribosomal peptide synthesis. Previously only a single method of effectively transforming *Burkholderia* has been described that is based on conjugation (Schellenberg et al. 2007). Conjugation methods are laborious and time consuming. In contrast to the methodology employed in the prior art, the method of the invention uses electroporation to provide an efficient and effective method for transforming *Burkholderia* with heterologous genetic elements such as PKS/NRPS gene clusters. Accordingly, this aspect of the invention provides a method for transforming a *Burkholderia* host cell with a heterologous genetic element, comprising a step of electroporation. The use of electroporation instead of conjugation in this method allows rapid transformation of *Burkholderia* cells, with the uptake of DNA molecules occurring extremely quickly. Extended culture times are not needed, as with conjugation, nor is it necessary to separate donor and recipient cells following transformation.

In preferred embodiments of the invention, heterologous nucleic acid is transferred into *Burkholderia* cells through electroporation. Preferably, an electroporation cuvette may be used, for example, with a 1 mm gap. In this embodiment, the cells are preferably electroporated at around 1250V, but the ability to test other effective voltages will be within the ambit of the person skilled in the art. The cells may be cultured prior to electroporation, ideally for longer than 1 hour, such as around 5 hours. If a culture vessel larger than around 5 ml is used, a longer culture time may be required. Following electroporation, the cells may be incubated to recover for over 30 minutes. Preferably, the cells are incubated following electroporation for approximately 2.5 hours.

Specific details of a preferred method of the invention are described below.

A hole is made in the lid of a 1.5 ml Eppendorf tube and a single colony is inoculated in 1.0 ml of CY medium. The cells are cultured overnight at 37° C. with shaking at 900 rpm.

A hole is made in the lid of a 2.0 ml Eppendorf tube and 1.9 ml of CY medium is inoculated with 50 μl of the overnight culture.

The 2.0 ml tube s incubated at 37° C. with shaking at 1100 rpm for 5 hours.

The cells are centrifuged at 9000 rpm for 20 seconds at 2° C. The supernatant is discarded and placed on ice.

The cells are re-suspended in 1.6 ml of ice-cold $dH_2O$.

The cells are centrifuged at 9000 rpm for 3 seconds.

The cells are re-suspended in 1.6 ml of ice-cold $dH_2O$.

The cells are centrifuged at 9000 rpm for 3 seconds.

The supernatant is discarded using a 1 ml pipette and leaving around 20-30 μl of solution (alternatively the supernatant can be discarded through swinging).

1 μg of plasmid DNA is added and the mixture was transferred to an ice-cold electroporation cuvette with a 1 mm gap.

The cells are electroporated at 1250V.

1.5 ml of CY medium is added and the cells were transferred to an Eppendorf tube.

The cells are incubated at 37° C. for 2.5 hours with shaking at 1100 rpm.

150 μl of transformed cells is plated on LB agar plates containing a suitable antibiotic.

The plates are incubated at 37° C. for 48 hours to allow colonies to be visualised.

Variations on this protocol will be apparent to those skilled in the art and are included in the scope of the invention.

*Agrobacterium tumefaciens*

In an embodiment of the invention, *Agrobacterium tumefaciens* is used as a heterologous host for the expression of genes capable of polyketide or non-ribosomal peptide synthesis, in the same manner as discussed above for *Burkholderia. Agrobacterium tumefaciens* is herein disclosed as a particularly suitable host for the expression of PKS/NRPS gene clusters and the production of polyketides or non-ribosomal peptides.

*Agrobacterium tumefaciens* is used extensively for plant transgenesis. It is also occasionally used to study pathogenic infection in relation to mammalian disease and is useful for studying quorum sensing. However, *Agrobacterium tumefaciens* has not previously been used for the synthesis of secondary metabolites as useful compounds and in particular has not been used for the production of compounds useful in treating mammalian disease such as cancer. However, this invention identifies that *Agrobacterium tumefaciens* is particularly suitable as a heterologous host. *Agrobacterium tumefaciens* can be cultured easily in a wide range of different media including LB medium. It has a short doubling time of 50 minutes and foreign DNA molecules up to 150 kb in length can be transferred by electroporation. Plasmids such as BAC have been successfully transformed into *Agrobacterium tumefaciens* and plasmids can propagate in *Agrobacterium tumefaciens* when they carry a suitable replication origin such as Ri ori or RK2 ori (oriV). Furthermore, the *Agrobacterium tumefaciens* genome has been sequenced and it has been found that the GC content is 59%. Therefore, *Agrobacterium tumefaciens* is particularly easy to culture and is amenable to genetic engineering and so is an ideal host for the expression of PKS/NRPS gene clusters and the production of polyketides or non-ribosomal peptides.

In a particularly preferred embodiment of the invention, *Agrobacterium tumefaciens* is used as a heterologous host for the expression of a PKS/NRPS gene cluster. The genome of *A. tumefaciens* has been sequenced and has been shown to contain a PKS/NRPS gene cluster encoding a siderophore (Rondon et al. 2004). Furthermore, analysis of the annotated genome sequence has revealed that *A. tumefaciens* has a number of important genes required for the heterologous expression of PKS/NRPS gene clusters. *A. tumefaciens* carries Atu4416, coding for 4'-phosphopantetheinyl transferase, a gene coding for methylmanonyl-CoA mutase and epimerase like genes required for methylmalonly-CoA production as a precursor for polyketide biosynthesis. These important genes make *A. tumefaciens* an ideal heterologous host for PKS/NRPS gene clusters.

*E. coli* Nissle 1917

In a further embodiment of the invention, *E. coli* Nissle 1917 is used as a heterologous host for the expression of genes capable of polyketide or non-ribosomal peptide synthesis, in the same manner as discussed above for *Burkholderia. E. coli* Nissle 1917 was isolated in 1917 by the German physician Alfred Nissle from the stool of a German soldier who, unlike his comrades, survived an outbreak of enterocolitis. This strain is widely used as a probiotic, produced under the trade name of Mutoflor™, to treat intestinal disorders including diarrhoea, irritable bowel disease, ulcerative colitis and Crohn's disease (Altenhoefer et al., 2004; Lodinova-Zadnikova et al., 1997; Rembacken et al., 1999). *E. coli* Nissle 1917 is furthermore of interest due to its ability specifically to grow in tumours. Bacteriolytic tumor-therapy was first described in the 1950s (Parker et al., 1947; Malmgren and Flanigan, 1955), based on the fact that some types of anaerobic bacteria can selectively propagate in tumours but not in other organs. These bacterial strains include *Bifidobacterium* (Yi et al., 2005), *Clostridia* species (Agrawal et al., 2004), *Corynebacterium parvum* (Fisher et al., 1990), *Salmonella typhimurium* (Zhao et al., 2005, 2006), *Salmonella choleraesuis* (Lee et al., 2004, 2005a,b)

and *Bordetella pertussis* (Pawelek, 2005). When *Vibrio cholerae* and *E. coli* were injected into tumour-bearing mice intravenously, tumour colonization also was observed although no quantitative data were provided (Yu et al., 2004). Recently, *E. coli* Nissle 1917 and *E. coli* K12 have been shown specifically to grow in tumours (Stritzker et al., 2007). This property of non-pathogenic *E. coli* strains (*E. coli* Nissle 1917 and *E. coli* K12) offers the possibility of using them for targeting drugs for bacteriolytic therapy. All of the former quantitative tumour colonisation experiments were based on pathogenic facultative anaerobic bacterial strains although some of pathogenic strains were virulence-attenuated by deletion of crucial metabolic genes and/or virulence factors (Pawelek et al., 1997, 2002, 2003; Low et al., 1999; Lee et al., 2004, 2005a,b; Zhao et al., 2005, 2006). Most anticancer drugs are delivered into patients orally or somatically, which results in prolonged side-effects. Therefore, it will be greatly advantageous to specifically deliver anticancer drugs into tumours to increase the effect of the drugs on the tumour and to reduce side-effects on other organs. Many trials have been performed to express anticancer peptides and RNAi in the bacterial strains selectively growing in tumours (Jia et al. 2005; Dang et al. 2001; Loeffler et al. 2007; Xiang et al. 2006). However, so far no work has been performed using these strains to express anticancer drugs from polyketides or non-ribosomal peptides which are the most effective drugs. *E. coli* in general is extremely easy to culture and is highly amenable to experimentation and manipulation. *E. coli* Nissle 1917 is particularly useful due to its non-pathogenic nature and its ability to specifically grow in tumours. Therefore, *Escherichia coli* Nissle 1917 is a particularly suitable heterologous host for the expression of genes capable of polyketide or non-ribosomal peptide synthesis, according to the present invention.

In a particularly preferred embodiment of the invention, *E. coli* Nissle 1917 is used as a heterologous host for the expression of a PKS/NRPS gene cluster. *E. coli* Nissle 1917 carries type I PKS/NRPS gene cluster islands, like other pathogenic *E. coli* strains, one of which encodes colibactin (Nougayrède et al., 2006; Homburg et al., 2007). Colibactin acts on DNA to make double-stranded breaks and it has anticancer activity. This gene cluster is intact and there is no significant difference between PKS gene clusters from *E. coli* Nissle 1917 and from pathogenic strains like uropathogenic CFT073. Upon co-cultivation of *E. coli* Nissle 1917 with eukaryotic cells, *E. coli* Nissle 1917 exerts a cytopathic effect (CPE) on eukaryotic cells in vitro (Putze et al., 2009). However, it was shown to have no anticancer effect in vivo even though it has excellent colonization in tumors (Stritzker et al., 2007, ibid). Activation of the PKS gene cluster will allow the synthesis of colibactin in *E. coli* Nissle 1917 and the use of this modified strain in cancer therapy. Furthermore, since *E. coli* Nissle 1917 carries its own PKS/NRPS gene clusters (unpublished genome sequencing data), it has the required components for expression of PKS/NRPS gene clusters which makes it particularly useful as a heterologous host for PKS/NRPS gene cluster expression.

The advantages described above in addition to the ability of *E. coli* Nissle 1917 to grow specifically in tumours (as discussed above) which makes it possible to use *E. coli* Nissle 1917 expressing PKS/NRPS gene clusters heterologously to deliver anticancer drugs directly to tumours. The invention therefore provides a method of treating cancer comprising the step of administering *E. coli* Nissle 1917 capable of expressing a PKS/NRPS gene cluster to a tumour. The invention also provides the use of *E. coli* Nissle 1917 capable of expressing a PKS/NRPS gene cluster in a method of treating cancer. In a particular embodiment, the *E. coli* Nissle 1917 is transformed with a vector comprising the MtaA gene. In one specific embodiment, the MtaA gene is under the control of a tetracycline inducible promoter. It has surprisingly been found that overexpressing the MtaA pPant transferase in *E. coli* Nissle 1917 leads to production of new compounds. Three main compounds have been identified with molecular weights of 572.2, 678.3 and 671.3. Thus, the invention provides a compound with a molecular weight selected from 572.2, 678.3 and 671.3 obtainable by expressing the MtaA pPant transferase in *E. coli* Nissle 1917. The invention also provides a compound with a molecular weight selected from 572.2, 678.3 and 671.3 obtainable by expressing the MtaA pPant transferase in *E. coli* Nissle 1917 for use in treating or preventing cancer. Also provided is a method of treating or preventing cancer comprising administering a compound with a molecular weight selected from 572.2, 678.3 and 671.3 obtainable by expressing the MtaA pPant transferase in *E. coli* Nissle 1917. Preferably, the compound with a molecular weight selected from 572.2, 678.3 and 671.3 obtainable by expressing the MtaA pPant transferase in *E. coli* Nissle 1917 is colibactin or a colibactin derivative.

*Photorhabdus luminescens*

In a still further embodiment of the invention, *Photorhabdus luminescens* can be used as a heterologous host for the expression of genes capable of polyketide or non-ribosomal peptide synthesis, in the same manner as discussed above. *Photorhabdus luminescens* is not currently used in genetic engineering or the synthesis of secondary metabolites. It is known to protect its nematode host through its toxicity to insects and is utilised for its luminescent properties. *Photorhabdus luminescens* is herein disclosed as a particularly suitable host for the expression of PKS/NRPS gene clusters and the production of polyketides or non-ribosomal peptides.

By searching sequenced genomes for clusters similar to the glidobactin cluster of DSM7029, an unknown cluster was identified in *Photorhabdus luminescens*. This cluster is defined herein as plu-glb. This discovery suggests that *Photorhabdus luminescens* is an ideal host for the expression of genes capable of polyketide or non-ribosomal peptide synthesis. As *Photorhabdus luminescens* has a cluster similar to the glidobactin cluster, it is considered by the inventors likely to have a number of genes that form parts of synthetic pathways involved in the synthesis of polyketides and non-ribosomal peptides. Therefore, less extensive engineering will be required to render the host capable of synthesising a range of useful compounds.

Furthermore, the identification of the uncharacterised gene cluster plu-glb in *Photorhabdus luminescens* allows the synthesis of novel compounds in *Photorhabdus luminescens*. In embodiments of the invention, the plu-glb cluster is activated in *Photorhabdus luminescens*. In certain embodiments, genetic elements are transferred to *Photorhabdus luminescens* in order to activate the expression of plu-glb or genes or gene clusters are expressed heterologously to supplement the pathway encoded by plu-glb.

In Vivo Expression

As discussed above, this invention provides hosts capable of heterologous expression of useful compounds. In certain preferred embodiments, the compounds expressed by hosts of the invention possess antiproliferative activity and are useful in the treatment of cancer. In further preferred embodiments of the invention, the hosts that produce compounds useful in the treatment of cancer are able to proliferate within tumours in a patient. Therefore, the hosts of the invention are able to propagate within the tumour to be targeted in a patient and are able to synthesise compounds to inhibit the growth of the tumour or kill the cells of the tumour.

Such a system has numerous advantages. It allows the specific targeting of therapeutic compounds to the target tissue, minimising the side effects on healthy tissue. Furthermore, tumours often have limited blood supplies so conventional drug treatment strategies do not necessarily result in drugs reaching the centre of tumours where they are needed. The administration of any of the hosts of the invention discussed above to a patient allows the expression and synthesis of compounds directly where they are required.

Preferred hosts are able to survive in the centre of a tumour rather than only at the periphery. Particularly preferred hosts are non-pathogenic. Additionally, in preferred embodiments, the expression of the compound is directed by an inducible promoter.

Generation of Heterologous Hosts

According to the invention, the hosts of the invention are engineered to synthesise compounds such as secondary metabolites. As discussed above, the secondary metabolite is preferably generated by a polyketide pathway, a non-ribosomal peptide (NRP) pathway or is synthesised by a pathway which combines enzymes from two or more of the pathways encoding these secondary metabolites, for example a hybrid polyketide-NRP.

According to the use of the invention, the genes of the biosynthetic pathway are transcribed under the control of promoters that are found naturally in the heterologous host cell. This allows the transcription machinery of the heterologous host cell to recognise its own promoters and thus transcribe the genes implicated in the metabolic pathway under study.

The use of a first host cell in which genetic manipulation is simple allows the alteration of the promoters in the heterologous host cell, without undue difficulty. Standard tools may be used for this manipulation, including PCR. Preferably, however, homologous recombination methodologies are used to alter the promoters, as necessary (see International patent applications WO99/29837 and WO02/062988; European patent applications 01117529.6 and 0103276.2; U.S. Pat. Nos. 6,509,156 and 6,355,412; and also (Muyrers, J. P. P. et al., 1999, 2000a,b,c, 2001; Zhang, Y et al., 1998, 2000, 2003).

One or more of the genes in the biosynthetic pathway may be cloned under the control of an inducible promoter. This will be particularly advantageous where the secondary metabolite is toxic to the heterologous host cell, since it will mean that the pathway can be established in the host while quantities of the host are grown up unaffected by the potential toxicity of the secondary metabolite.

This approach is advantageous over those alternatives used in the art—existing systems that involve the expression of a toxic gene product generally circumvent the problem of toxicity by an alternative strategy, namely that of co-expressing a resistance gene that transports the toxic product out of the cell. In a system such as that described herein, the expression of a resistance gene is not feasible, as the nature of the (only potentially toxic) secondary metabolite being expressed is not known, for example, where the method is used to screen a library of secondary metabolites. Using an inducible promoter to govern expression of one or more of the genes necessary for production of the secondary metabolite allows the cells to grow to a high cell density before the inducing agent is added, and expression of a high level of the secondary metabolite is only induced at that point. If the metabolite is toxic, the cells will die, but while dying will still produce a sufficient quantity of secondary metabolite for further analysis or purification.

Preferred inducible promoters will be those which are induced by small molecules. Examples of suitable systems are known in the art, and include the toluic acid inducible Pm promoter in *Pseudomonas* species described by (Abril M. A et al., 1989), which is an example of a preferred inducible promoter. Other preferred promoters include the tetracycline inducible promoter pTet and the constitutive promoter Tn5.

One advantage of the use of an inducible promoter, particularly in the context of a screen for bioactive metabolites (among the most interesting of which will be those with antibiotic or cytotoxic properties) is that host cell death upon promoter induction acts as a preliminary screen for those compounds that merit further investigation.

Thus, where a method of the present invention is used to express a secondary metabolite that is toxic to the second host cell, cell death may be used as an indication that the secondary metabolite is bioactive. Preferably, the inducible promoter will be one that can be regulated with small ligands so that potential toxic effects of the expressed secondary metabolite can be managed with ease.

Preferably, the heterologous host cell is a cell which normally expresses secondary metabolites of the type in which there is an interest, particularly secondary metabolites of the class that is being expressed (i.e. generated by NRP pathways, type I polyketides pathways etc.). An appropriate choice of the second host cell will ensure that this host is well adapted for expression of the secondary metabolite. The second host cell may be a cell which does not naturally express the precise secondary metabolite of interest.

Certain host cells do not naturally express one or more of the substrates that are required for biosynthesis of certain classes of secondary metabolite. For example, type I polyketide synthases catalyze the successive condensation of carboxylic acid residues from their substrates such as malonyl-CoA and methylmalonyl-CoA. Malonyl-CoA is a substrate for primary metabolism pathway and is present in all bacteria. However, methylmalonyl-CoA (a second common precursor of polyketides) is not naturally produced in a wide range of bacterial strains.

A heterologous host for all kinds of polyketide gene cluster expression should synthesize methylmalonyl-CoA. Thus, if it does not already express the requisite genes, the heterologous host cell is preferably transformed with genes encoding the enzymes required for making substrates that are required to synthesise the secondary metabolite but which are not naturally expressed in the wild-type heterologous host cell. Preferably, the genes are integrated into the chromosome of the heterologous host cell. Alternatively, a substrate which is not normally expressed in the second host cell may be induced to be expressed in the second host cell by replacement of the endogenous promoter governing expression of the appropriate gene with an appropriate constitutive or inducible promoter, and/or by culturing it under specific conditions.

As discussed herein, examples of suitable heterologous host cells are *Burkholderia*, DSM7029, *Agrobacterium tumefaciens, Escherichia coli* Nissle 1917 and *Photorhabdus luminescens*.

It should also be the case that the heterologous host cell should be cultured under conditions which are suitable for synthesis of the secondary metabolite. Suitable conditions for growth of the host cell will be evident to those of skill in the art. As referred to above, in preferred systems according to the invention, an inducible promoter is used in one or more of the genes that form part of the biosynthetic pathway under study; in these systems, the inducing agent will preferably be added once the host cells have attained a high cell density. This will minimise cell death during earlier stages of growth as a result of potential toxicity of the secondary metabolite produced.

The invention thus incorporates a test for determining whether a secondary metabolite that is toxic for a heterologous host cell is bioactive, by gauging the effect of induction of the complete biosynthetic pathway on the growth of the host cells in which this is taking place.

The transfer of a complete biosynthetic pathway to a heterologous host that does not normally contain that pathway can lead to the accumulation of the expected product of that pathway, but also to the accumulation of novel derivatives of the end product of the pathway, and to novel derivatives of biosynthetic intermediates. Shuffling of modules and genes between and within gene clusters will also generate novel compounds.

The methodology of the invention may be performed iteratively, with successive rounds of screening and selection in order to allow the molecular evolution of one or more of the genes that participates in the pathway toward a desired function. Indeed, an entire pathway can be evolved in this fashion.

For example, the genes encoding the enzymes of the biosynthetic pathway may optionally be further genetically engineered. Mutagenesis of the genes encoding the enzymes is an advantageous way to alter the chemical product because the structure of the secondary metabolite is directed by the specificity of the enzymes of the biosynthetic pathway. Where the secondary metabolite has useful biological properties, genetic engineering of the secondary metabolite preferably alters the biological properties of the secondary metabolite itself, for example, by altering the structure of the molecule generated by the biosynthetic pathway. For example, genetic engineering may enable an increase in the half-life of the secondary metabolite or may increase its specific activity. Where the secondary metabolite is an antibiotic, genetic engineering may for example decrease the IC50 of the antibiotic when compared to the IC50 of the antibiotic synthesised by wild-type enzymes. Furthermore, genetic manipulation may confer a new biological property on the secondary metabolite and/or may delete an existing property. Genetic manipulation of this type may be carried out by shuttling a vector selected in the second host cell back into the first host cell, or may be carried out directly in the second host cell or in a further host cell.

Because of the relative ease of genetic manipulation in the cloning host, however, it is likely that in most circumstances, genetic manipulation will be effected in the first host cell and then the vector transformed back into the heterologous host cell for screening and selection. The use of a first host in which genetic engineering techniques are well established enables genetic engineering to be carried out with a high degree of accuracy and in particular enables site-directed mutagenesis to be carried out in order to alter the secondary metabolite specifically. Random and/or combinatorial mutagenic approaches may alternatively or additionally be used for the creation of libraries of mutations, including approaches such as DNA shuffling, STEP and sloppy PCR, and molecular evolution. A random and/or combinatorial approach enables libraries of different secondary metabolites to be created.

The genetic engineering of one or more genes in the biosynthetic pathway may involve any suitable type of mutagenesis, for example, substitution, deletion or insertion mutagenesis. If the sequence encoding the one or more genes contains redundant, irrelevant and potentially undesirable sequences, genetic engineering can be carried out to remove these sequences from the vector. Mutagenesis may be carried out by any suitable technique known in the art, for example, by site-directed mutagenesis or by transposon-mediated mutagenesis, as the skilled reader will appreciate. Site-directed mutagenesis may be used to insert new restriction sites, alter glycosylation patterns, change codon preference, produce splice variants, introduce mutations and so forth. Recombineering may also be used where appropriate.

The heterologous host cell may be cultured under any suitable conditions, as will be understood by those of skill in the art. However, it is preferred that the heterologous host cell is cultured between 10° C. and 20° C., for example between 13° C. and 18° C. In a particularly preferred embodiment, the second host cell is cultured at 16° C. If the heterologous host cell is to be used for in vivo expression of secondary metabolites, it is preferred that it is cultured between, 30° C. and 40° C., in particular 37° C.

The invention will now be described in detail, by way of specific reference to examples. It should be understood that these examples are not intended to be limiting in any way and that divergence from these examples will be within the ambit of the skilled reader once aware of the teachings above.

EXAMPLES

Example 1

The Generation of Expression Plasmids for the Expression of Glidobactin in DSM7029

To allow the expression of glidobactin A in heterologous hosts, RecET system was used to clone the glidobactin (glb) gene cluster.

Figure 1:
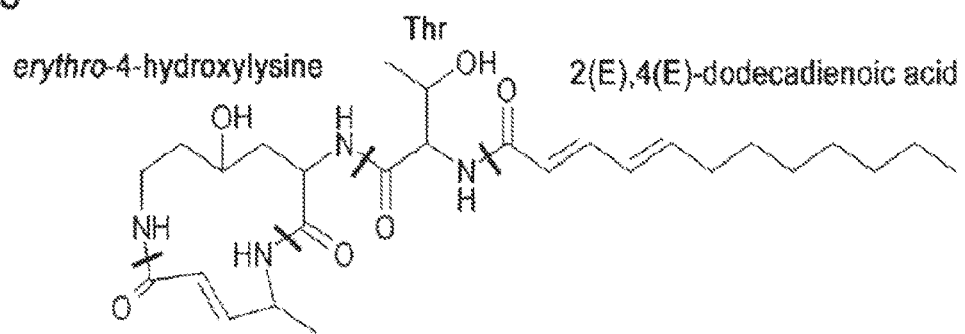
FIG. 1. The structure of Glidobactin A.
Figure 2:
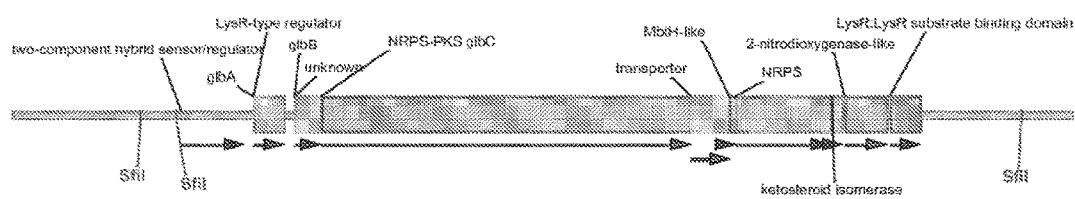
FIG. 2. Glidobactin (glb) gene cluster.
Figure 3:
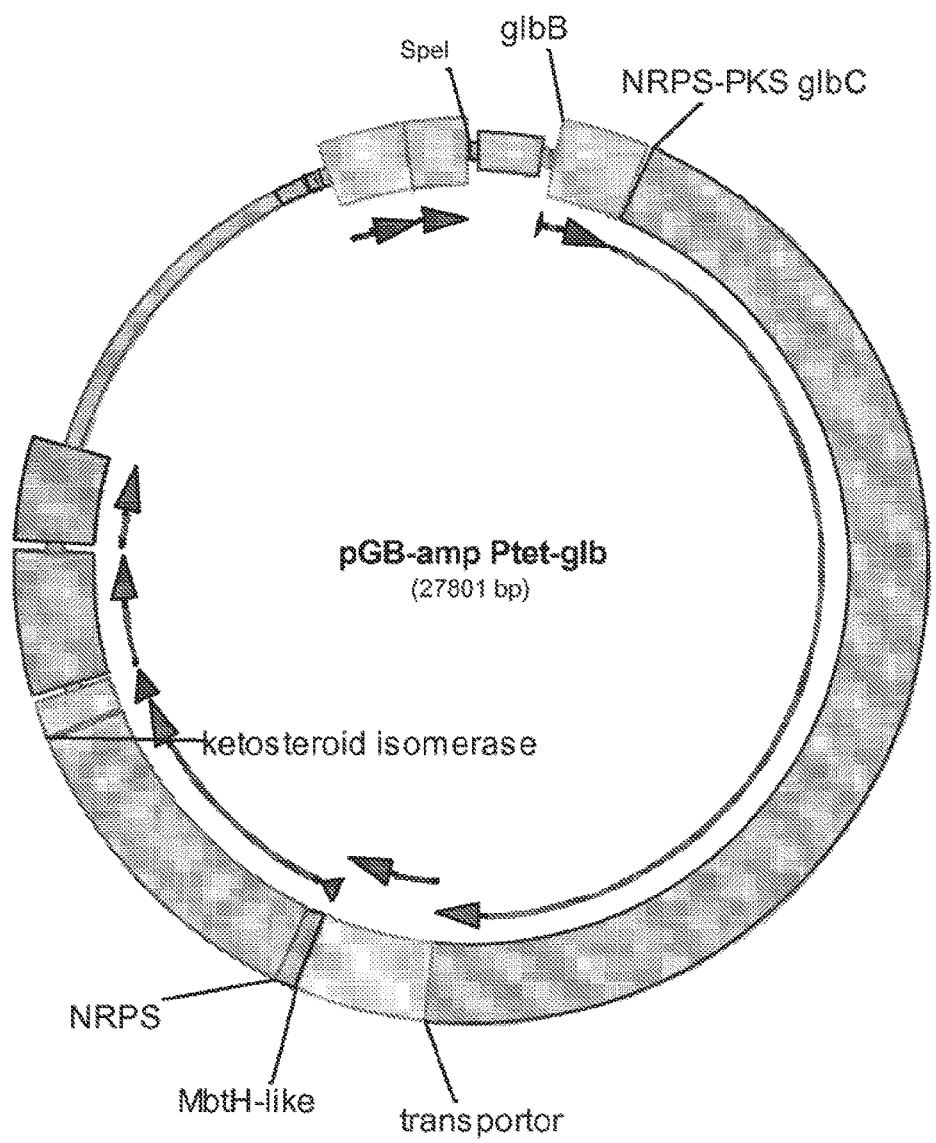
FIG. 3. The final pGB-amp Ptet-glb plasmid for the expression of Glidobactin A.

To clone the glb gene cluster, genomic DNA from DSM7.029 was prepared and digested with Sfi I. YZ2005, comprising RecE and RecT, was then transformed with this genomic preparation and a linear vector to utilise RecET to subclone the gene cluster into a plasmid (FIG. 3).

Figure 4:
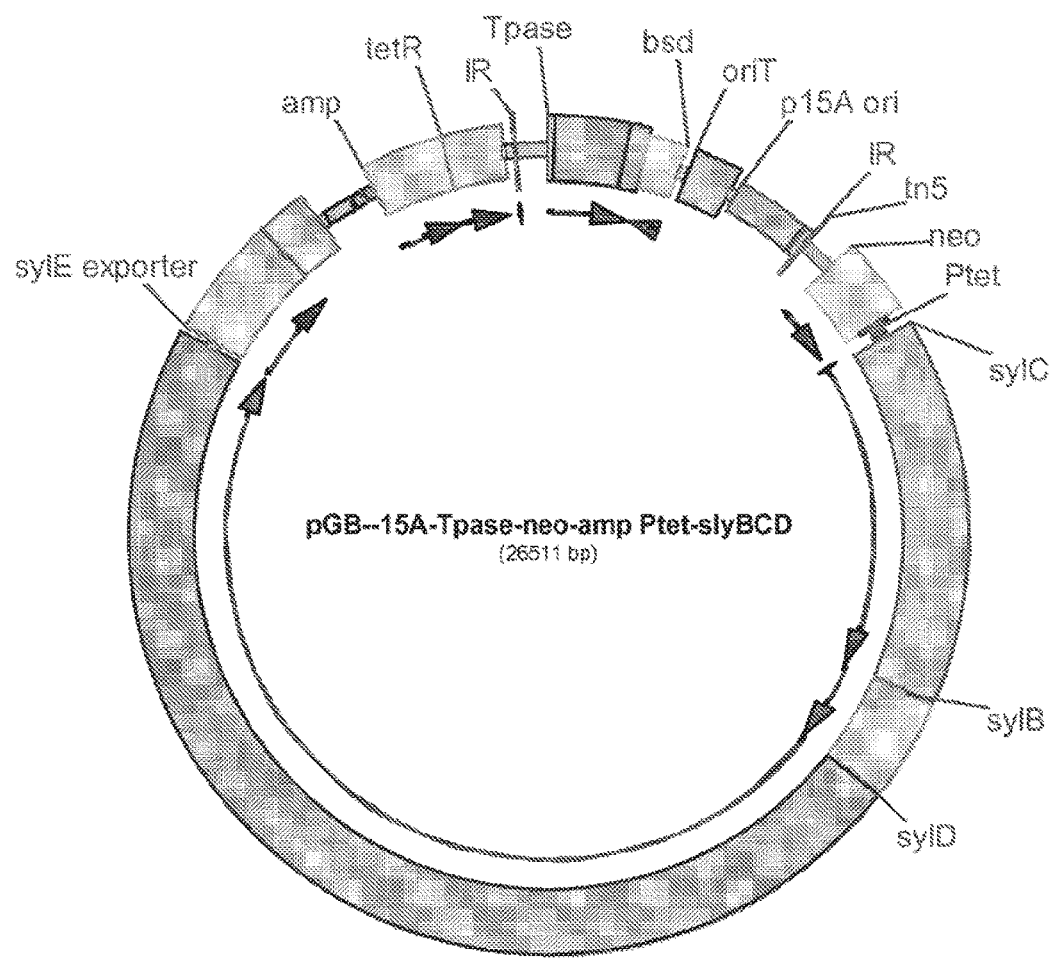
FIG. 4. The pGB-15A-Tpase-neo-amp Ptet-syl plasmid comprising p15A origin and transposase cassette.
Figure 5:
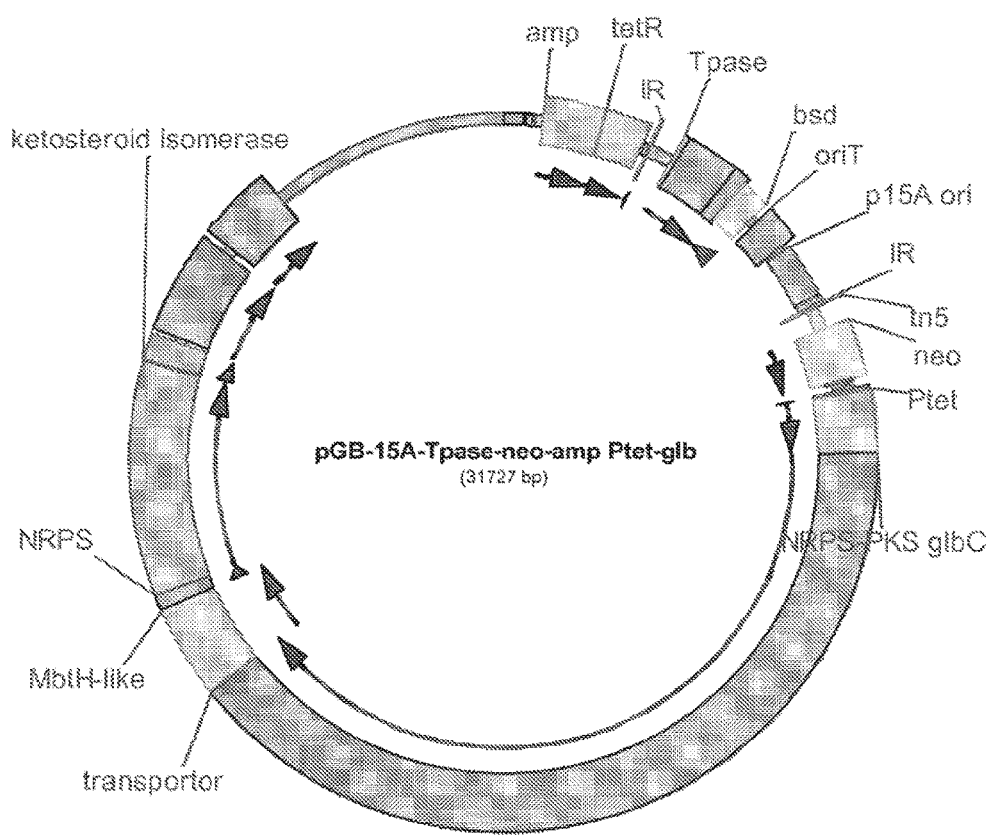
FIG. 5. The pGB-15A-Tpase-neo-amp Ptet-glb plasmid for integration into the chromosome of DSM7029 comprising p15A origin and transposase cassette.

The construct was further modified to allow the expression of the metabolites in DSM7029 *Burkholderia*. ColE1 plasmids cannot replicate in DSM7029 so the construct was integrated into the chromosome of DSM7029. The p15A origin of replication and a transposase cassette (Tpase-bsd-oriT) from p15A-Tn5-neo-epo-Tpase-BSD-oriT was used to replace the colE1 origin (FIGS. 4 and 5).

Glidobaction A, B and C were produced from the endogenous glb gene cluster It is therefore demonstrated that such gene clusters can be successfully transferred to heterologous hosts for the heterologous expression of secondary metabolites.

The glb expression cluster is, therefore, suitable for transferral to a heterologous host for expression of glidobactin A and related molecules. Suitable heterologous hosts include *Photorhabdus luminescens*, *Escherichia coli* Nissle 1917, *Agrobacterium tumefaciens* and DSM7029 *Burkholderia*. *Escherichia coli* Nissle 1917 and *Photorhabdus luminescens* are particularly suitable heterologous hosts. Furthermore, there are great possibilities in generating novel compounds with useful properties such as anticancer compounds by swapping modules and domains between gene clusters.

Example 2

Heterologous Expression of Epotholines in DSM7029

The epothilone gene cluster was engineered to carry the transposase (Tps) and invert sequences (IR) as described above. Using RecE, a 57-59 kb DNA fragment comprising the epothilone gene cluster under the Tn5 constitutive promoter was cloned and integrated into the chromosome of DSM 7029.

Transformation was performed according to the following protocol using ice-cold $dH_2O$, and Eppendorfs and electroporation cuvettes cooled to 2° C.

1. A hole was made in the lid of a 1.5 ml Eppendorf tube and a single colony was inoculated in 1.0 ml of CY medium. The cells were cultured overnight at 37° C. with shaking at 900 rpm.
2. A hole was made in the lid of a 2.0 ml Eppendorf tube and 1.9 ml of CY medium was inoculated with 50 μl of the overnight culture.
3. The 2.0 ml tube was incubated at 37° C. with shaking at 1100 rpm for 5 hours.
4. The cells were centrifuged at 9000 rpm for 20 seconds at 2° C. The supernatant was discarded and placed on ice.
5. The cells were re-suspended in 1.6 ml of ice-cold dH$_2$O.
6. The cells were centrifuged at 9000 rpm for 3 seconds.
7. The cells were re-suspended in 1.6 ml of ice-cold dH$_2$O.
8. The cells were centrifuged at 9000 rpm for 3 seconds.
9. The supernatant was discarded using a 1 ml pipette and leaving around 20-30 μl of solution (alternatively the supernatant can be discarded through swinging).
10. 1 μg of plasmid DNA was added and the mixture was transferred to an ice-cold electroporation cuvette with a 1 mm gap.
11. The cells were electroporated at 1250V.
12. 1.5 ml of CY medium was added and the cells were transferred to an Eppendorf tube.
13. The cells were incubated at 37° C. for 2.5 hours with shaking at 1100 rpm.
14. 150 μl of transformed cells was plated on LB agar plates containing a suitable antibiotic.
15. The plates were incubated at 37° C. for 48 hours to allow colonies to be visualised.

A small transpositional plasmid pTpase-lacZ (15.6 kb) and a large transpositional plasmid p15A-Tn5-neo-epo-Tpase-BSD-oriT (61 kb) (Fu J et al., 2008) were transferred into DSM7029 by performing the electroporation procedure as described above. The stably integrated recombinants were kanamycin resistant. Colonies on kanamycin (50 m/ml) plates were counted and the total number per transformation is shown below:

| | |
|---|---|
| pTps-lacZ | 4870 |
| p15A-Tn5-neo-epo-Tpase-BSD-oriT | 420 |

Compared to the conventional conjugation methods, this electroporation transformation method is efficient, simple and fast and is not dependent on helper DNA. Two positive clones were selected and were analysed for epothilone production. Cells and XAD were harvested via centrifugation at 10000 rpm for 10 minutes and extracted with 10 ml acetone and 30 ml methanol. The filtered extract was dried by vacuum electroporation, resuspended with 1 ml methanol and analysed by HPLC/MS and HPLC/MS/MS (HPLC: Agilent 1100 Series, CC 125/2 Nucleodur C18 Gravity, 3 μm; MS: Bruker HCT Plus; 0 min-22 min 5%-95% acetonitrile with 0.1% formic acid) (FIGS. 7-10).

The data shows that Epothilone C and Epothilone D were successfully produced by DSM7029 comprising the epothilone gene cluster under Tn5 inducible promoter.

Figure 6:
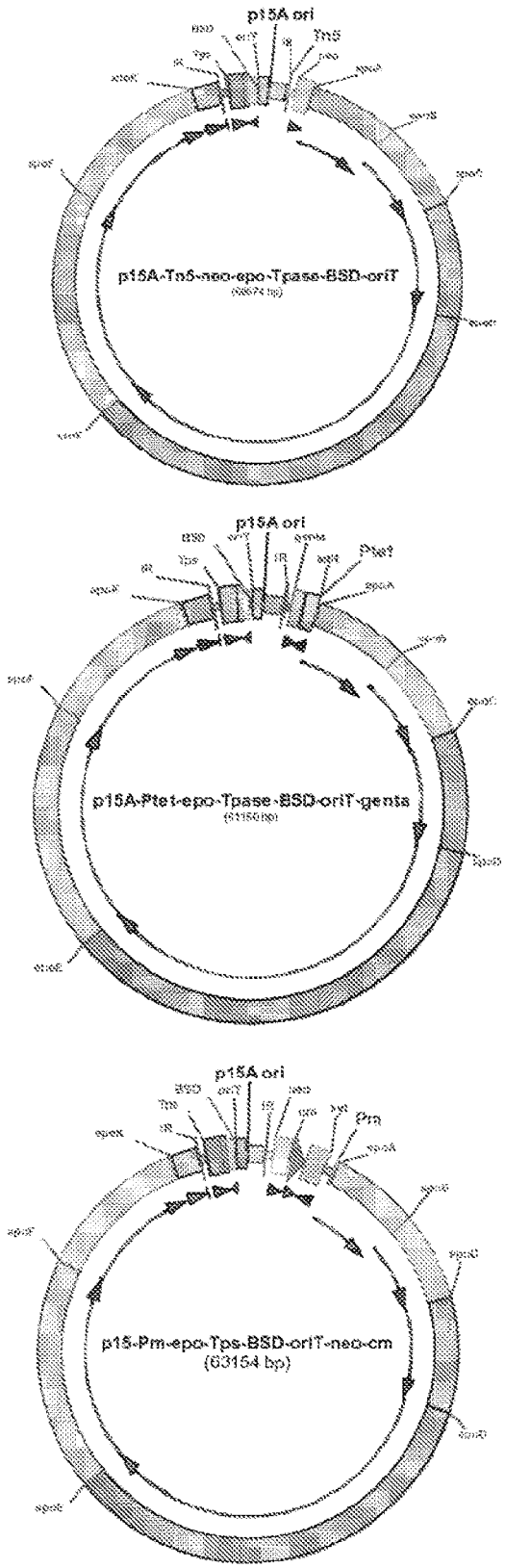
FIG. 6. Expression constructs for the expression of epothilone. The complete epothilone gene cluster was cloned between IRs for transposition. The transposase gene and oriT were cloned into the vector backbone. The top plasmid has the constitutive Tn5 promoter. The middle plasmid has the tetracycline inducible promoter Ptet. The lower plasmid has the toluic acid inducible promoter.
Figure 7:
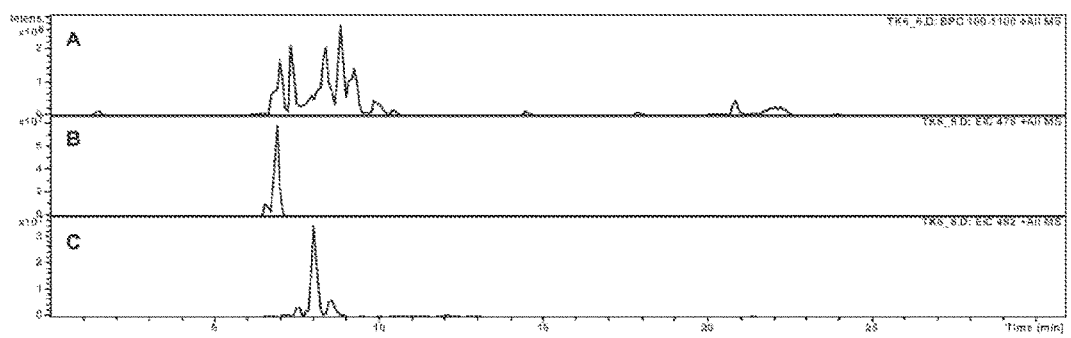
FIG. 7. HPLC/MS analysis of epothilone production by DSM7029 wildtype. Base peak chromatogram (m/z 100-1100); A) positive mode. B) Extracted-Ion-Chromatogram m/z 478 from Epothilone C. C) Extracted-Ion-Chromatogram m/z 492 from Epothilone D.
Figure 8:
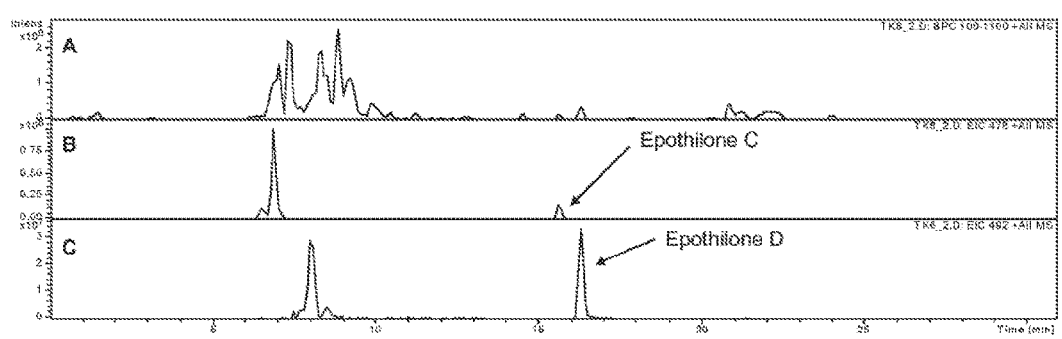
FIG. 8. HPLC/MS analysis of epothilone production by DSM7029 kan1, with epothilone gene cluster. Base peak chromatogram (m/z 100-1100); A) positive mode. B) Extracted-Ion-Chromatogram m/z 478 from Epothilone C. C) Extracted-Ion-Chromatogram m/z 492 from Epothilone D.
Figure 9:
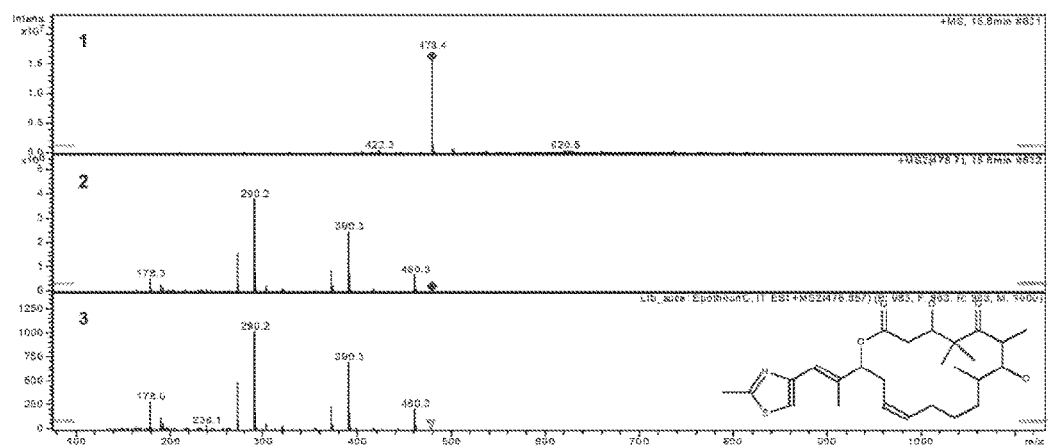
FIG. 9. 1) HPLC/MS analysis of epothilone production by DSM7029 kan1, with epothilone gene cluster. 2) MS/MS analysis from epothilone C fragmentation pattern for comparison to 3) epothilone C from internal compound library.
Figure 10:
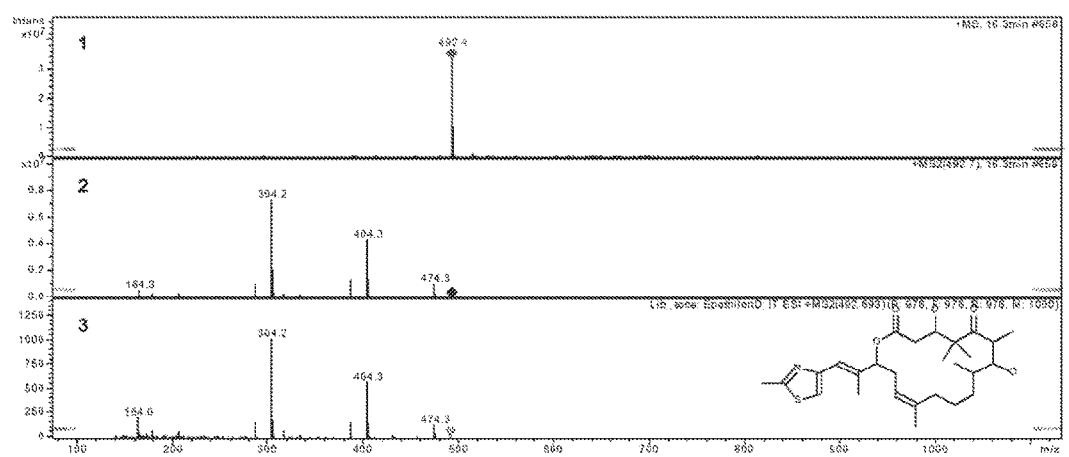
FIG. 10. 1) HPLC/MS analysis of epothilone production by DSM7029 kan1, with epothilone gene cluster. 2) MS/MS analysis from epothilone D fragmentation pattern for comparison to 3) epothilone D from internal compound library.

Furthermore, additional constructs have been made using RecE to generate expression plasmids with the epothilone gene cluster under the control of alternative promoters such as Ptet and Pm (FIG. 6).

TABLE 1

Epothilone production by 4 individual DSM7029 clones with the epothilone gene cluster. Quantification of Epothilones C and D in *Polyangium (Burkholderia)* DSM7029

| | Epothilon C [μg/l culture] | Epothilon D [μg/l culture] |
|---|---|---|
| *Polyangium* Kan 1 | 14.2 | 4.8 |
| *Polyangium* Kan 3 | 8 | 3.1 |
| *Polyangium* Kan 5 | 10.7 | 5.9 |
| *Polyangium* Kan 7 | 10.1 | 4.4 |

Example 3

Reclassification of DSM7029

DSM7029 was previously classified as a myxobacterium. However, myxobacteria are characterised by a long doubling time and slow growth. In contrast, DSM7029 grows fast and its doubling time was estimated as 1 hour. Therefore, it was investigated whether DSM7029 is, in fact, a myxobacterium. 16S rRNA coding sequences from DSM7029 strains (wild-type and kan1) were amplified and sequenced.

```
Partial sequence of 16S rRNA gene of DSM7029 wildtype
                                              (SEQ ID NO: 1)
CCCTTATGACTACTTGTTACGACTTCACCCCAGTCACGAACCCTGCCGTGGTGATCGCCCT

CCTTGCGGTTAGGCTAACCACTTCTGGCAGAACCCGCTCCCATGGTGTGACGGGCGGTGT

GTACAAGACCCGGGAACGTATTCACCGCGGCATGCTGATCCGCGATTACTAGCGATTCCGA

CTTCACGCAGTCGAGTTGCAGACTGCGATCCGGACTACGACCGGTTTTCTGGGATTAGCTC

CCCCTCGCGGGTTGGCAGCCCTCTGTACCGGCCATTGTATGACGTGTGTAGCCCTACCCAT

AAGGGCCATGATGACCTGACGTCATCCCCACCTTCCTCCGGTTTGTCACCGGCAGTCTCAT

TAGAGTGCCCTTTCGTAGCAACTAATGACAAGGGTTGCGCTCGTTGCGGGACTTAACCCAA

CATCTCACGACACGAGCTGACGACGGCCATGCAGCACCTGTGTCCAGGTTCTCTTTCGAGC

ACTCCCACATCTCTGCAGGATTCCTGGCATGTCAAGGGTAGGTAAGGTTTTTCGCGTTGCA
```

```
-continued
TCGAATTAAACCACATCATCCACCGCTTGTGCGGGTCCCCGTCAATTCCTTTGAGTTTCAAC

CTTGCGGCCGTACTCCCCAGGCGGTCAACTTCACGCGTTAGCTTCGTTACTGAACAGCAAG

CCGTCCAACAACTAGTTGACATCGTTTAGGGCGTGGACTACCAGGGTATCTAATCCTGTTTG

CTCCCCACGCTTTCGTGCATGAGCGTCAGTGCAGGCCCAGGAGATTGCCTTCGCCATCGG

TGTTCCTCCGCATATCTACGCATTTCACTGCTACACGCGGAATTCCATCTCCCTCTGCCGCA

CTCTAGCCGTGCAGTCACAAATGCAGTTCCCAGGTTGAGCCCGGGGATTTCACATCTGTCT

TGCACAACCGCCTGCGCACGCTTTACGCCCAGTAATTCCGATTAACGCTCGCACCCTACGT

ATTACCGCGGCTGCTGGCACGTAGTTAGGCGGGTGCTTATTCTTCAGGTACCGTCATCGGC

TCCGGGGTATAGCCCAGAACTTTTCTTCCCTGACAAAAGCGGTTTACACCCGGACGTCTTC

TTCCCGCACGCGGCATGGCTGGATCAGGCTGCGCCATGGTCAAAACTCCCCACTGCTGCC

TCCGTAGGAGTCTGGCGTGTCCTCAGTCCCAGGTGTGGCTTGTCGTCCTCTCAGACAGCTA

CGATCGTCGCATGTAGCTACCCACACACTAGCTAATCTGACTCGGGCGATCAAATAGGCGC

GAGCCTTGGCAATTCTGT

Partial sequence of 16S rRNA gene of Dsm7029 Kan1
                                                (SEQ ID NO: 2)
TCGTAATTGCTCATTGTTACGACTTCACCCCAGTCACGAACCCTGCCGTGGTGATCGCCCT

CCTTGCGGTTAGGCTAACCACTTCTGGCAGAACCCGCTCCCATGGTGTGACGGGCGGTGT

GTACAAGACCCGGGAACGTATTCACCGCGGCATGCTGATCCGCGATTACTAGCGATTCCGA

CTTCACGCAGTCGAGTTGCAGACTGCGATCCGGACTACGACCGGTTTTCTGGGATTAGCTC

CCCCTCGCGGGTTGGCAGCCCTCTGTACCGGCCATTGTATGACGTGTGTAGCCCTACCCAT

AAGGGCCATGATGACCTGACGTCATCCCCACCTTCCTCCGGTTTGTCACCGGCAGTCTCAT

TAGAGTGCCCTTTCGTAGCAACTAATGACAAGGGTTGCGCTCGTTGCGGGACTTAACCCAA

CATCTCACGACACGAGCTGACGACGGCCATGCAGCACCTGTGTCCAGGTTCTCTTTCGAGC

ACTCCCACATCTCTGCAGGATTCCTGGCATGTCAAGGGTAGGTAAGGTTTTTCGCGTTGCA

TCGAATTAAACCACATCATCCACCGCTTGTGCGGGTCCCCGTCAATTCCTTTGAGTTTCAAC

CTTGCGGCCGTACTCCCCAGGCGGTCAACTTCACGCGTTAGCTTCGTTACTGAACAGCAAG

CCGTCCAACAACTAGTTGACATCGTTTAGGGCGTGGACTACCAGGGTATCTAATCCTGTTTG

CTCCCCACGCTTTCGTGCATGAGCGTCAGTGCAGGCCCAGGAGATTGCCTTCGCCATCGG

TGTTCCTCCGCATATCTACGCATTTCACTGCTACACGCGGAATTCCATCTCTCTGCCGCA

CTCTAGCCGTGCAGTCACAAATGCAGTTCCCAGGTTGAGCCCGGGGATTTCACATCTGTCT

TGCACAACCGCCTGCGCACGCTTTACGCCCAGTATTTCCGATTAACGCTCGCACCCTACGT

ATTACCGCGGCTGCTGGCACGTAGTTAGCCGGTGCTTATTCTTCAGGTACCGTCATCGCTC

CGGGGGTATTAGCCCAGATCTTTTCTTCCCTGACAAAGCGGTTTACACCCGGACGTCTTCTT

CCGGCACGGCGGCATGGCTGGATCAGGCTTGCGCCGATGATCCAAACTCCCCACTGCTGC

CTCAGTAGGAGTCTGGGGCCGTGTCTCAGTCCCAGGGTGGCTGTCGTCCTCTCGACTAGC

TACGAATCGCTCGCTTGTAGCATACCACCAACTAGCTAATCTGACATCGACGTTCATTAGGC

GGGAGGCTGTGGCAAATC
```

These sequences were analysed with Blast and except for one hit which was *Polyangium brachysporum* (itself), all other similar sequences that were identified were *Burkholderia* strains. To investigate further the 16S rRNA sequences, the sequences from DSM7029 were compared to those from various different strains of myxobacterium and *Burkholderia*. It was found that there was a high sequence similarity between DSM7029 16S rRNA sequences and those from *Burkholderia* strains. In contrast, there was low sequence similarity between DSM7029 16S rRNA sequences and those from myxobacteria strains, despite low variance between different myxobacteria strains.

Therefore, this evidence strongly suggests that DSM7029 is, in fact, a *Burkholderia* and not a myxobacteria.

TABLE 2

Partial comparison of 16S rRNA genes from DSM7029 and myxobacterium
(SEQ ID NOS 5-13, respectively, in order of appearance)

```
GTCGAGTTGCAGACTG-----CGATCCG-GACTACGACCGGTTTT-CTGGGATTAG--C----TCC---
CCCTCGCGGG---------TTGGCAGCCCTCTGTACCGG--------CCATTGTA----TGACGTGTGT

ACCAAGGCAACGACGGGTAGCTGGTCTGAGAGGACGATCAGCCACACTGGAACTGAGACACGGTCCAGA
CTCCTACGGGAGGCAGCAGTGGGGAATCTTGCGCAATGGGCGAAAGCCTGACGCAGCAACGCCGCGTGT

ACCAAGGCGACGACGGGTAGCTGGTCTGAGAGGACGATCAGCCACACTGGAACTGAGACACGGTCCAGA
CTCCTACGGGAGGCAGCAGTGGGGAATTTTGCGCAATGGGCGAAAGCCTGACGCAGCAACGCCGCGTGT

ACCAAGGCAACGACGGGTAGCTGGTCTGAGAGGACGATCAGCCACACTGGAACTGAGACACGGTCCAGA
CTC-TACGGGAGGCAGCAGTGGGGAATCTTGCGCAATGGGCGAAAGCCTGACGCAGCAACGCCGCGTGT

ACCAAGGCTACGACGGGTAGCTGGTCTGAGAGGATGATCAGCCACACTGGAACTGAGACACGGTCCAGA
CTCCTACGGGAGGCAGCAGTGGGGAATATTGCGCAATGGGCGAAAGCCTGACGCAGCAACGCCGCGTGT

ACCAAGGCTACGACGGGTAGCTGGTCTGAGAGGATGATCAGCCACACTGGAACTGAGACACGGTCCAGA
CTCCTACGGGAGGCAGCAGTGGGGAATATTGCGCAATGGGCGAAAGCCTGACGCAGCAACGCCGCGTGT

ACCAAGGCGACGACGGGTAGCTGGTCTGAGAGGATGATCAGCCACACTGGAACTGAGACACGGTCCAGA
CTCCTACGGGAGGCAGCAGTGGGGAATCTTGCGCAATGGGCGAAAGCCTGACGCAGCAACGCCGCGTGT

ACCAAGGCGACGACGGGTAGCTGGTCTGAGAGGATGATCAGCCACACTGGAACTGAGACACGGTCCAGA
CTCCTACGGGAGGCAGCAGTGGGGAATCTTGCGCAATGGGCGAAAGCCTGACGCAGCAACGCCGCGTGT

ACCAAGGCGACGACGGGTAGCTGGTCTGAGAGGATGATCAGCCACACTGGAACTGAGACACGGTCCAGA
CTCCTACGGGAGGCAGCAGTGGGGAATCTTGCGCAATGGGCGAAAGCCTGACGCAGCAACGCCGCGTGT
```

From top to the bottom: DSM7029; *Anaeromyxobacter dehalogenans* strain 2CP-1; *Corallococcus coralloides* strain Cc9736; Myxobacterium KC; Myxobacterium SHI-1; Myxobacterium SMH-27-4; *Polyangium cellulosum* So ce56; *Polyangium cellulosum* So ce90; *Polyangium cellulosum* So0089-1.

TABLE 3

Partial comparison of 16S rRNA genes from DSM7029 and *Burkholderia* strains
(SEQ ID NOS 14-26, respectively, in order of appearance)

```
gcgttgcatcgaattaatccacatcatccaccgcttgtgcgggtccccgtcaattcctttgagttttaatcttgc
gaccgtactccccaggcggtcaacttcacgcgttagctacgtta gcgttgcatcgaattaatccacatcatccaccgcttgtgcgggtccccgtcaattcctttgagttttaatcttgc
gaccgtactccccaggcggtcaacttcacgcgttagctacgtta gcgttgcatcgaattaatccacatcatccaccgcttgtgcgggtccccgtcaattcctttgagttttaatcttgc
gaccgtactccccaggcggtcaacttcacgcgttagccacgtta gcgttgcatcgaattaatccacatcatccaccgcttgtgcgggtccccgtcaattcctttgagttttaatcttgc
gaccgtactccccaggcggtcaacttcacgcgttagctacgtta GCGTTGCATCGAATTAAACCACATCATCCACCGCTTGTGCGGGTCCCCGTCAATTCCTTTGAGTTTCAACCTTGC
GGCCGTACTCCCCAGGCGGTCAACTTCACGCGTTAGCTTCGTTA gcgttgcatcgaattaatccacatcatccaccgcttgtgcgggtccccgtcaattcctttgagttttaatcttgc
gaccgtactccccaggcggtcaacttcacgcgttagctacgtta gcgttgcatcgaattaatccacatcatccaccgcttgtgcgggtccccgtcaattcctttgagttttaatcttgc
gaccgtactccccaggcggtcaacttcacgcgttagctacgtta gcgttgcatcgaattaatccacatcatccaccgcttgtgcgggtccccgtcaattcctttgagttttaatcttgc
gaccgtactccccaggcggtcaacttcacgcgttagctacgtta gcgttgcatcgaattaatccacatcatccaccgcttgtgcgggtccccgtcaattcctttgagttttaatcttgc
gaccgtactccccaggcggtcaacttcacgcgttagctacgtta gcgttgcatcgaattaatccacatcatccaccgcttgtgcgggtccccgtcaattcctttgagttttaatcttgc
gaccgtactccccaggcggtcaacttcacgcgttagctacgtta gcgttgcatcgaattaatccacatcatccaccgcttgtgcgggtccccgtcaattcctttgagttttaatcttgc
gaccgtactccccaggcggtcaacttcacgcgttagctacgtta gcgttgcatcgaattaatccacatcatccaccgcttgtgcgggtccccgtcaattcctttgagttttaatcttgc
gaccgtactccccaggcggtcaacttcacgcgttagctacgtta
```

TABLE 3 -continued

Partial comparison of 16S rRNA genes from DSM7029 and *Burkholderia* strains
(SEQ ID NOS 14-26, respectively, in order of appearance)

gcgttgcatcgaattaatccacatcatccaccgcttgtgcgggtccccgtcaattcctttgagttttaatcttgc
gaccgtactccccaggcggtcaacttcacgcgttagctacgtta From top to bottom: *Burkholderia mallei* strain NCTC 10260; *Burkholderia pseudomallei* BCC215; *Burkholderia gladioli* strain R1879; *Burkholderia gladioli* strain R406; DSM7029; *Burkholderia mallei* strain ATCC 23344; *Burkholderia mallei* strain NCTC 10260; *Burkholderia mallei* strain 2000031063; *Burkholderia cepacia* strain 2Pe38; *Burkholderia cepacia* strain 1-3b; *Burkholderia cepacia* strain ESR87; *Burkholderia cepacia* strain NE9; *Burkholderia mallei* strain AE9.

Example 4

The Expression of Myxochromide Heterologously in *Agrobacterium tumefaciens*

Figure 11:
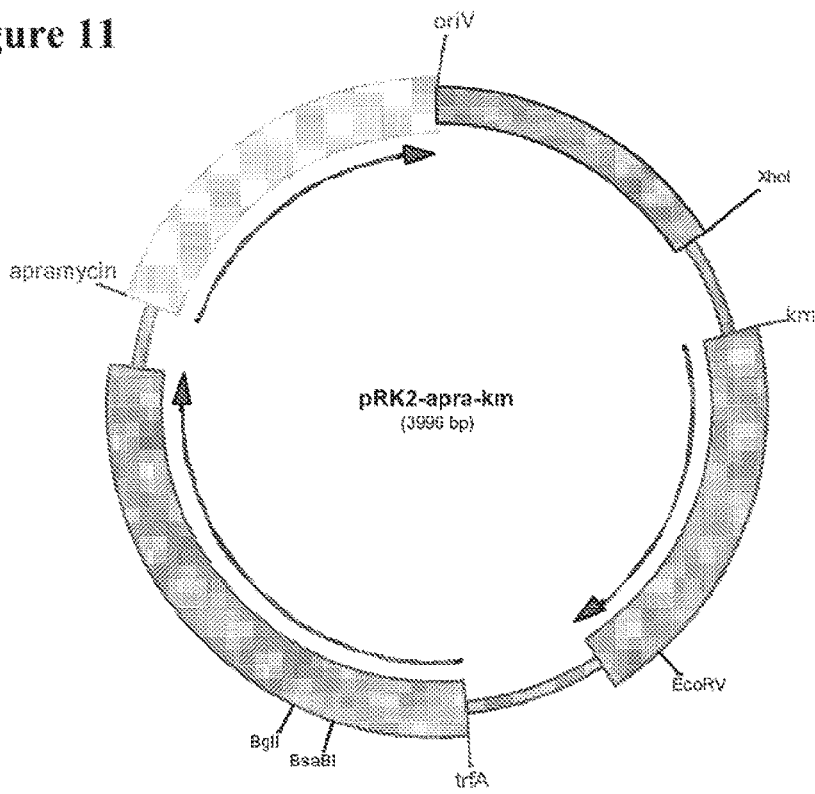
FIG. 11. pRK2-apra-km and pRK2-genta-km constructs comprising oriV, apramycin or gentamycin resistance and replicon (TrfA).
Figure 11:
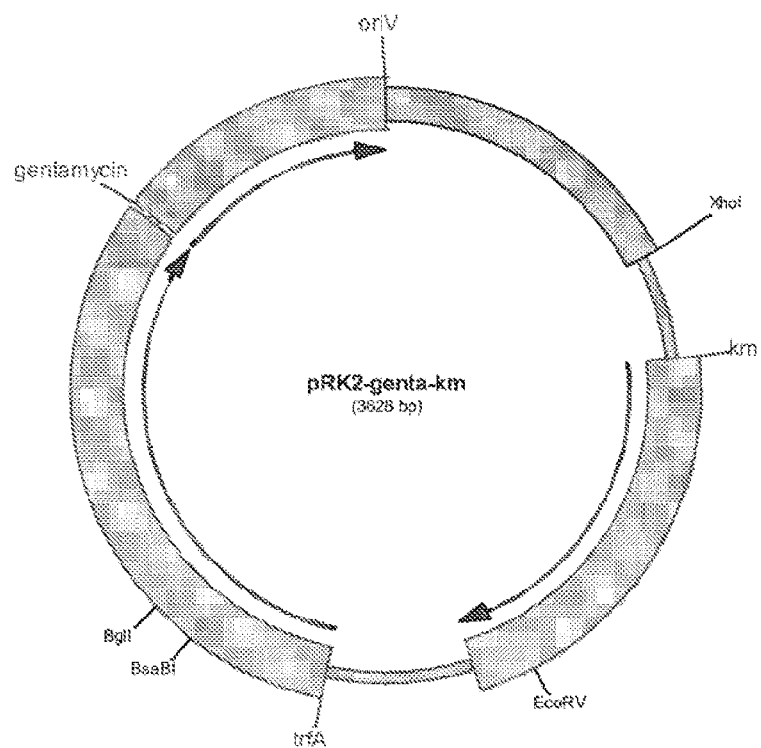

The mchS gene cluster with the Pm promoter has the necessary components for *Pseudomonas* expression but cannot be expressed in *A. tumefaciens* C58. The plasmid was modified to make it possible to express it in *A. tumefaciens* C58. Two constructs were made based on a shuttle vector pBC301 with kanamycin resistance and either apramycin resistance or gentamycin resistance. Vitally, they were made with oriV cassettes to allow them to replicate in *A. tumefaciens* C58 (FIG. 11).

Figure 12:
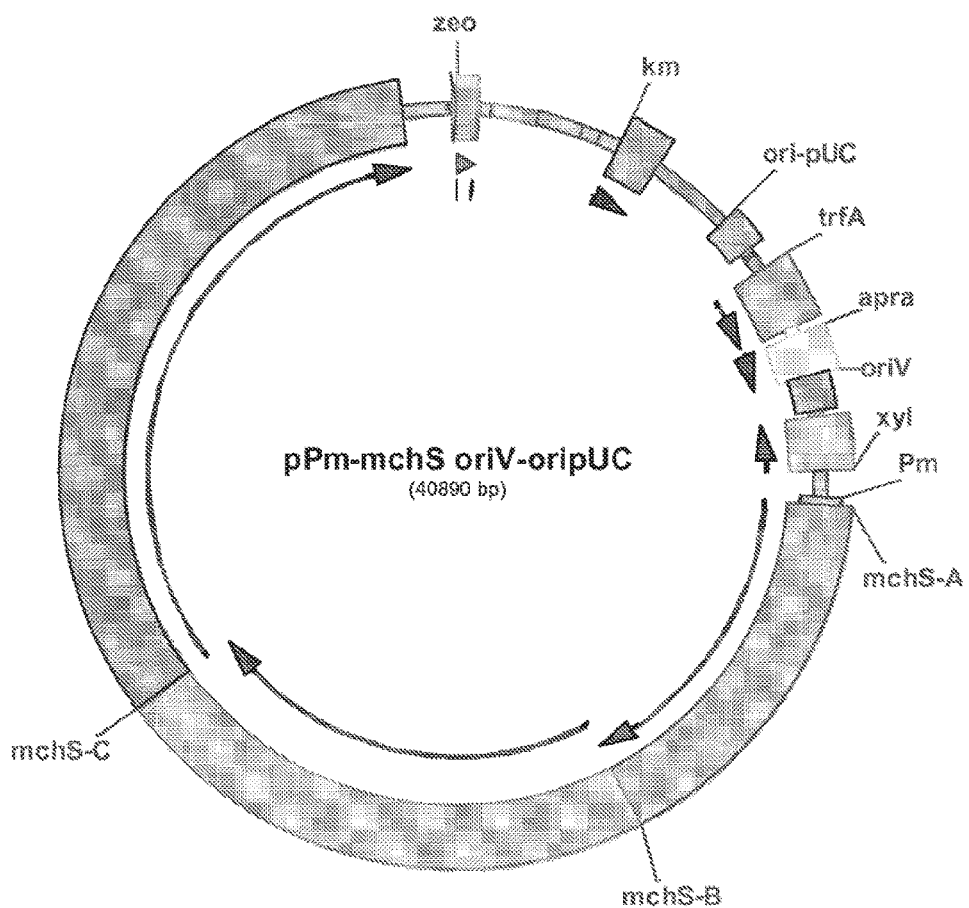
FIG. 12. pPm-mchS oriV-oripUS plasmid comprising mchS gene cluster and toluic acid inducible promoter.

The cassette trfA-apra-oriV was generated by PCR with two homology arms at its ends by using the template generated above (FIG. 3) and inserted into the vector backbone used for *Pseudomonas* expression to form pPm-mchS oriV-oripUC (FIG. 12). Myxochromide gene cluster (mchS) is under Pm inducible promoter in this construct.

Figure 13:
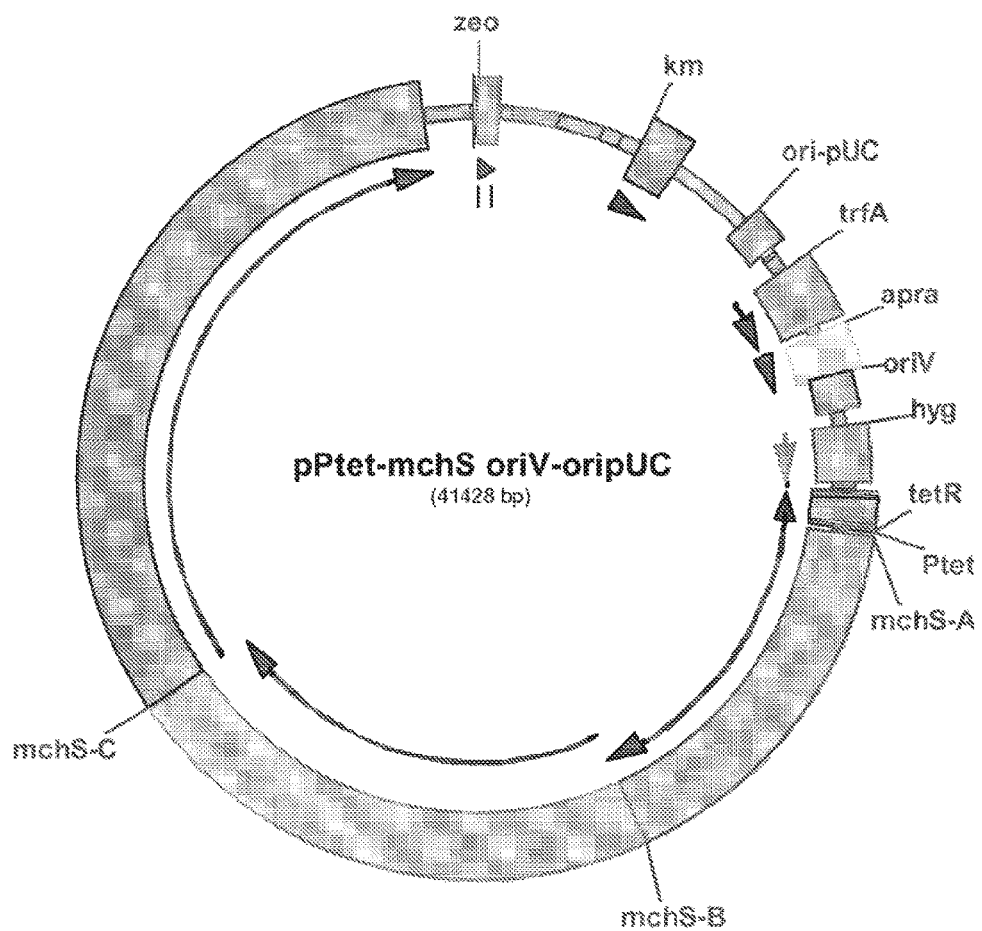
FIG. 13. pPtet-mchS oriV-oripUC plasmid comprising mchS gene cluster and tetracycline inducible promoter.

The ability of different promoters to drive mxyochromide was investigated. Constructs were generated carrying the toluic acid inducible promoter (Pm) and the tetracycline inducible promoter (Ptet) with the mchS gene cluster. To test the Ptet inducible promoter, one cassette carrying the hygromycin resistance gene, the regulator gene tetR and the tetracycline inducible promoter (Ptet) was inserted in front of mchS gene cluster to form pPtet-mchS oriV-oripUC (FIG. 13). Constructs with the Pm and Ptet inducible promoters were transformed then into *A. tumefaciens* C58 by electroporation. Plasmid DNA prepared from the transformants was verified by restriction analysis. The plasmids are able to stably propagate under selection pressure.

Figure 14:
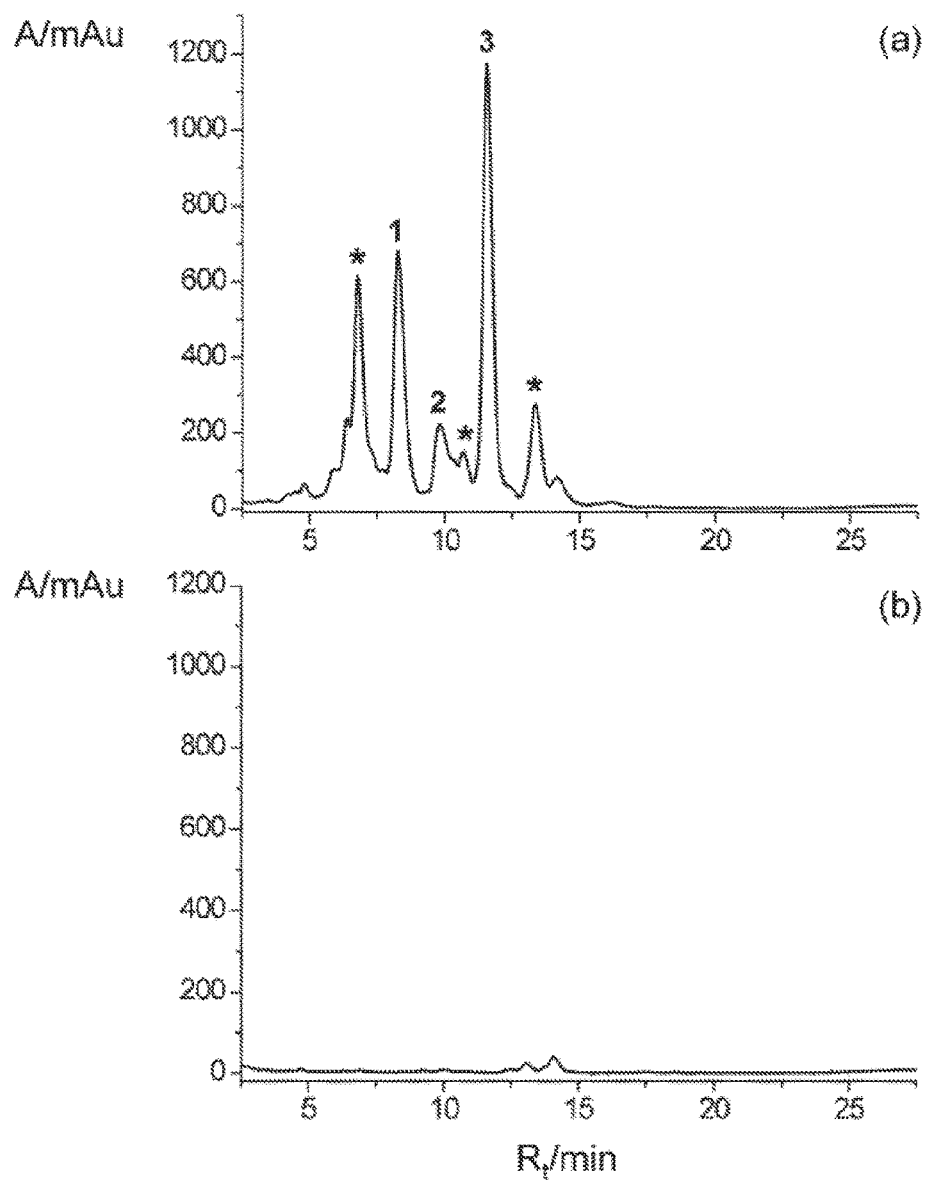
FIG. 14. HPLC profiles from extracts of a) the *A. tumefaciens* C58::pPtet-mchS oriV-oripUS mutant strain and b) *A. tumefaciens* C58 wild-type. Diode array detection at 400 nm. Peaks are numbered as follows; 1—Myxochromide $S_1$, 2—Myxochromide $S_2$, 3—Myxochromide $S_3$. Peaks marked with an asterix are assumed to be Myxochromide S derivatives as well.

*A. tumefaciens* C58 carrying the constructs was cultured in LB medium. Myxochromide compounds were then extracted and detected. As shown in the HPLC profiles from the extract, the pPtet promoter was able to drive expression and successful synthesis of Myxochromide $S_1$, Myxochromide $S_2$, and Myxochromide $S_3$ (FIG. 14). The Pm promoter was similarly able to drive successfully synthesis (data not shown).

Example 5

Expression of Epothilone Gene Cluster in *Agrobacterium tumefaciens*

Figure 15:
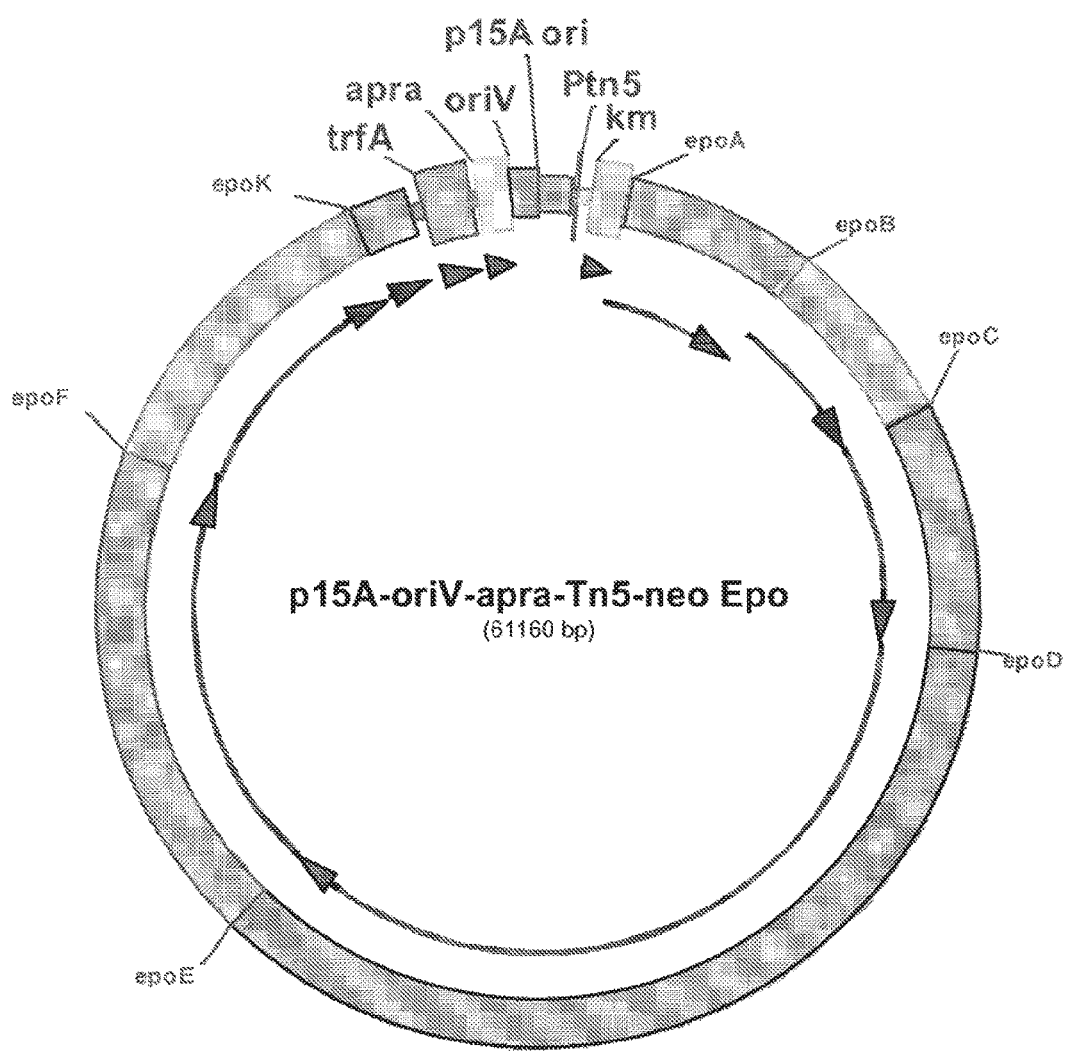
FIG. 15. p15A-oriV-apra-Tn5-neo Epo epothilone expression plasmid with Tn5 promoter.

The trfA-apra-oriV cassette was inserted in the epothilone cluster construct used for *Myxococcus xanthus* expression by Fu et al. 2008 to form p15A-oriV-apra-Tn5-neo-epo (FIG. 15). The epothilone cluster was driven by Tn5 promoter in this construct.

Following transformation, kanamycin resistant clones were identified and it was verified by restriction analysis that they were carrying the epothilone gene cluster.

To make this construct capable of successfully expressing epothilone, the methlymalonyl-coA mutase pathway must be integrated. This will then allow the synthesis of this useful compound from *A. tumefaciens*.

Example 6

Expression of Colibactin-Anticancer Compounds in *E. coli* Nissle 1917

Figure 16:
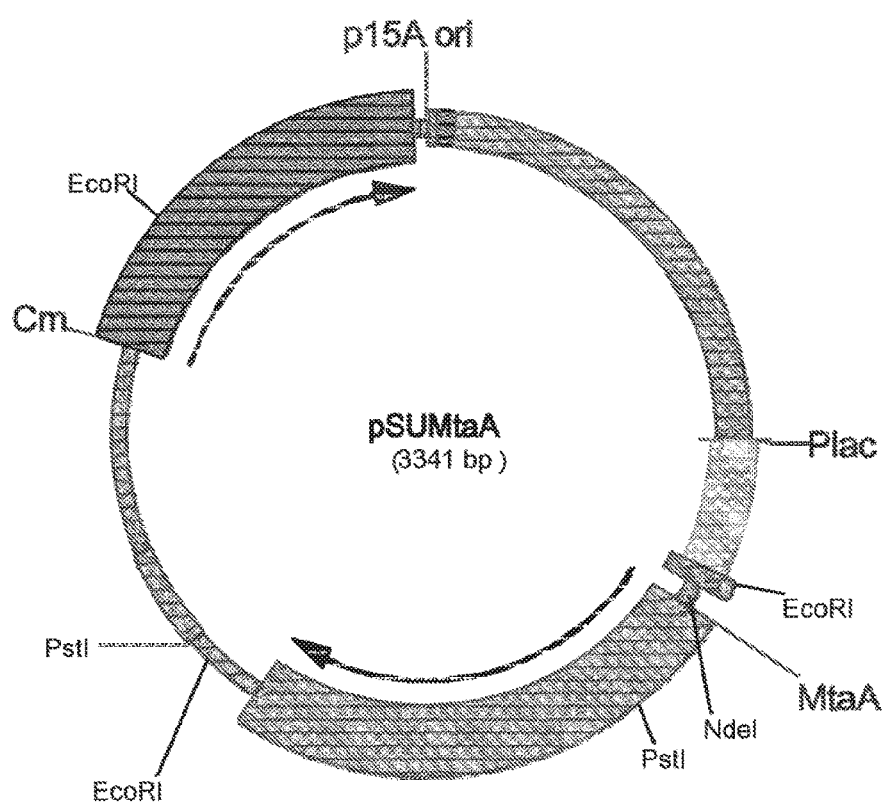
FIG. 16. Map of MtaA expression construct. The MtaA gene was cloned from Myxothiazol gene cluster in *Stigmatella aurantiaca* DW4/3-1 strain (Silakowski et al., 1999; Gaitatzis et al., 2001). It activates both PKS and NRPS enzymes. The sequence of the gene and encoded protein are given as SEQ ID NO: 3 and SEQ ID NO: 4 respectively.
Figure 17:
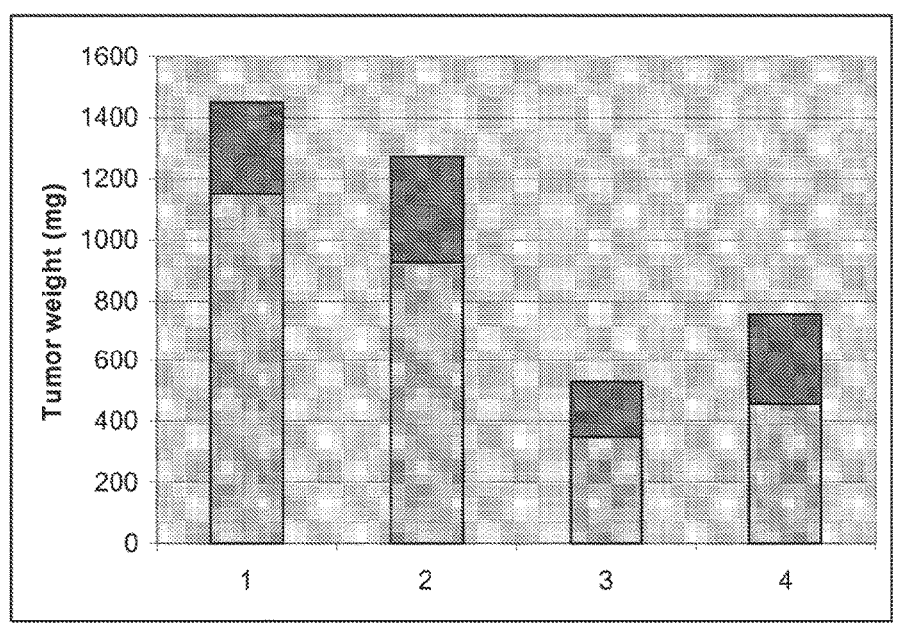
FIG. 17. In vivo activity of *E. coli* Nissle 1917 clones with or without over expression of MtaA. 10 nude mice bearing human neck and head tumors (UT-SCC-5) for each group were injected in tumor (i.t.) with $1\times10^7$ bacterial cells in PBS in 5 µl volume. PBS alone was used as negative control. Tumors were harvested after 3 weeks and tumor weight was measured. The colonization of bacterial cells in tissues (tumor, liver and kidney) was measured by plating the extract from homogenized tissues. Colonization data (not shown) is similar to the previously published data (Stritzker et al., 2007).
Figure 18:
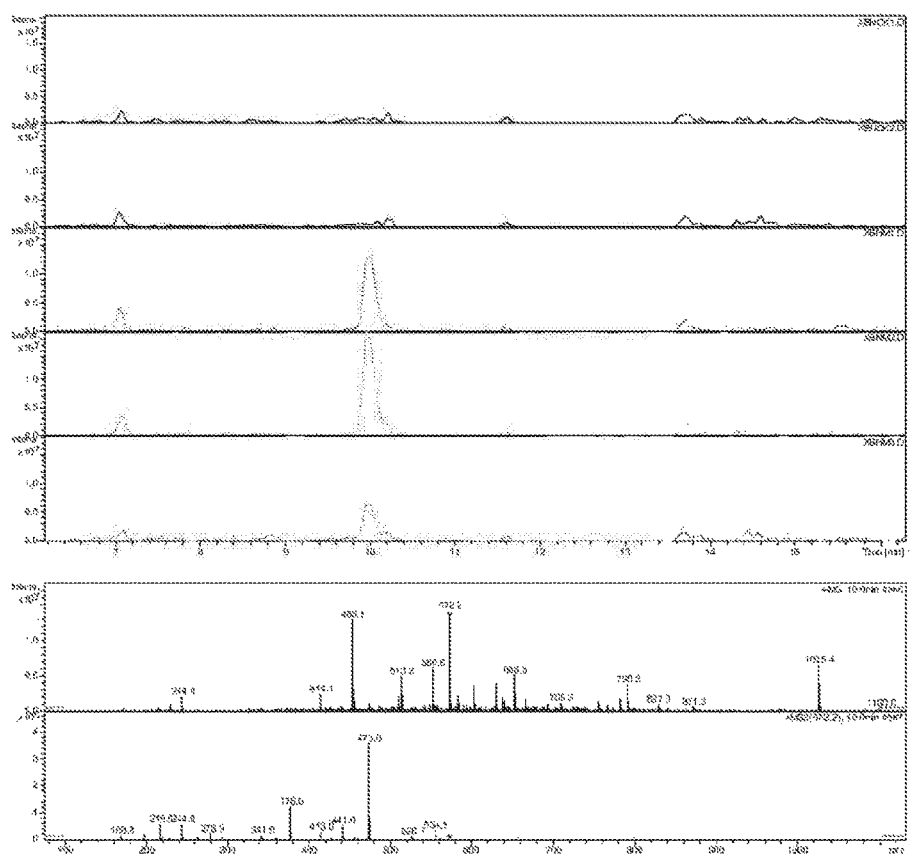
FIG. 18. New compounds produced in *E. coli* Nissle 1917 after over expression of MtaA gene. Three main compounds with MW 572.2, 678.3 and 671.3 are present only in clones overexpressing MtaA. There are other new compounds produced in a relative smaller quantity (data not shown).
Figure 18:
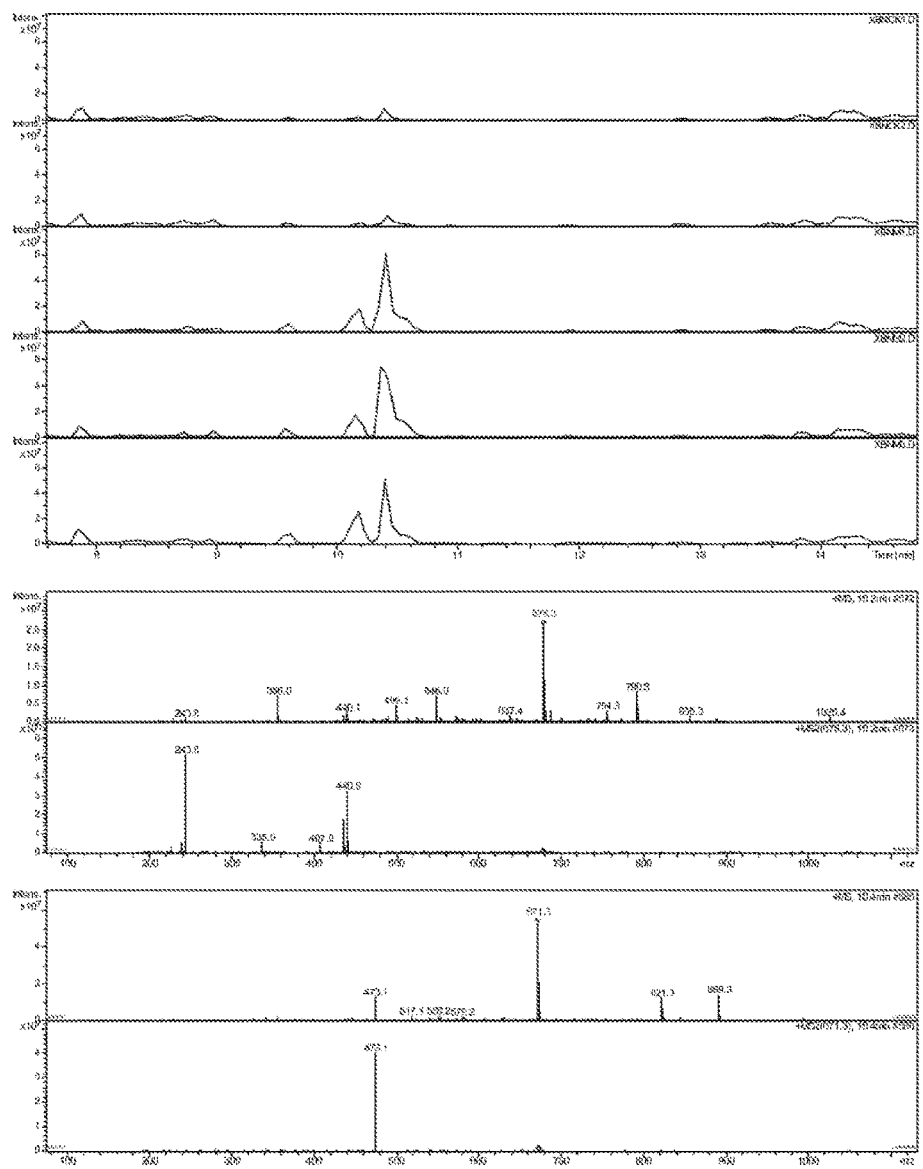

4' phosphopantetheinyl (pPant) transferase is a component required to activate the PKS/NRPS enzymes. An overexpression plasmid of a known universal pPant transferase gene called MtaA (pSUMtaA) (Gaitatzis et al., 2001) (FIG. 16) was transformed into *E. coli* Nissle 1917. This pPant transferase has advantage of activating both PKS and NRPS enzymes which are presented in most of the gene clusters including colibactin, glidobactin and epothilone. When the transformants expressing exogenous pPant transferase were tested in vivo, they showed activity to against cancer (FIG. 17). As shown by previous publication (Stritzker et al., 2007), the original *E. coli* Nissle 1917 has no effect on the tumor growth in vivo. LC-MS data shows several new compounds are produced after overexpression of MtaA gene in *E. coli* Nissle 1917 (FIGS. 18A and B). To be able to control the expression of colibactin gene cluster, MtaA gene was cloned under a tetracycline inducible promoter and it has been transformed into *E. coli* Nissle 1917.

Figure 19A:
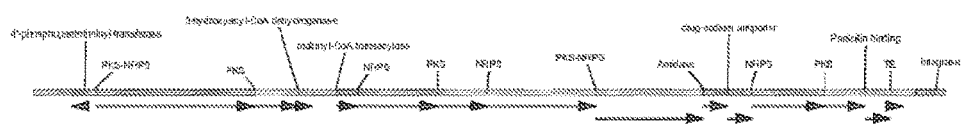
FIG. 19. *E. coli* Nissle 1917 colibactin gene cluster and its engineering. A) The original gene cluster includes 16 genes that are a mixture of PKS and NRPS. B) To activate the pPant transferase gene, a constitutive promoter plus chloramphenicol resistance gene (cm) was inserted in front of the gene using homologous recombination. C) A tetracycline inducible promoter was added in front of the PKS gene cluster.
Figure 19B:
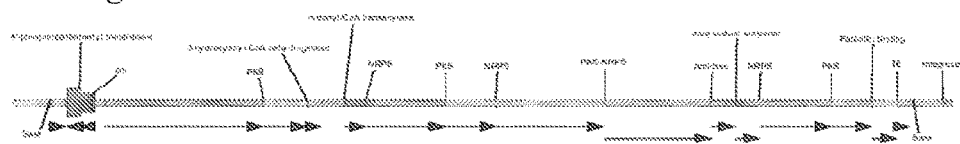
Figure 19C:
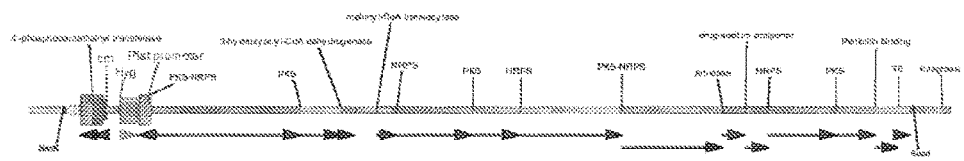
Figure 20:
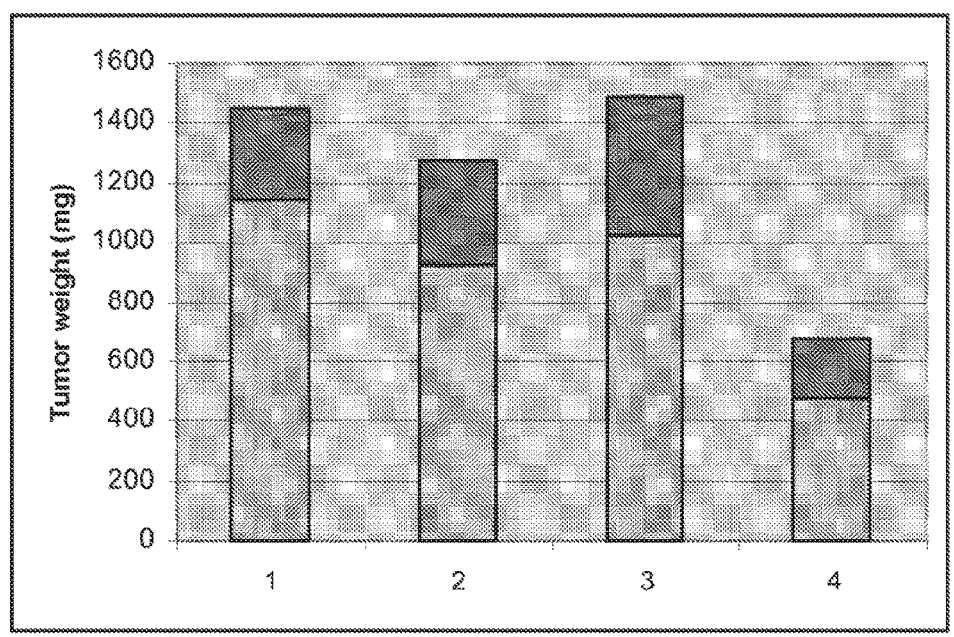
FIG. 20. In vivo activity of *E. coli* Nissle 1917 with activation of endogenous pPant transferase. The experiment was done as described in FIG. 17.

Upstream of the colibactin PKS/NRPS gene cluster is a predicted endogenous pPant transferase gene (FIG. 19 A). To test whether this component is functional, a chloroamphenicol (Cm) resistance gene and a ribosomal binding site were inserted in front of the pPant transferase gene (FIG. 19 B). Endogenous pPant transferase gene is under the control of a Cm promoter and is expressed constitutively. The transformed strain showed activity against cancer in vivo (FIG. 20). A cassette containing hyg-tetR-Ptet was then inserted in front of the PKS/NRPS gene cluster (FIG. 19 C) to regulate colibactin expression. The pPant transferase gene is predicted to be activated constitutively and the colibactin PKS/NRPS gene cluster is activated by the addition of tetracycline.

Following tetracycline induction, secondary metabolites were extracted and detected. The new compounds produced after activation of endogenous pPant transferase are the same as additional exogenous pPant transferase (FIGS. 18A and B).

Data from both experiments indicate that over expression of a pPant transferase gene in *E. coli* Nissle 1917 can activate anticancer compounds and also improve the heterologous production of polyketides and non-ribosomal peptides.

Example 7

In Vitro Test of Expression of Colibactin in *E. coli* Nissle 1917

Figure 21:
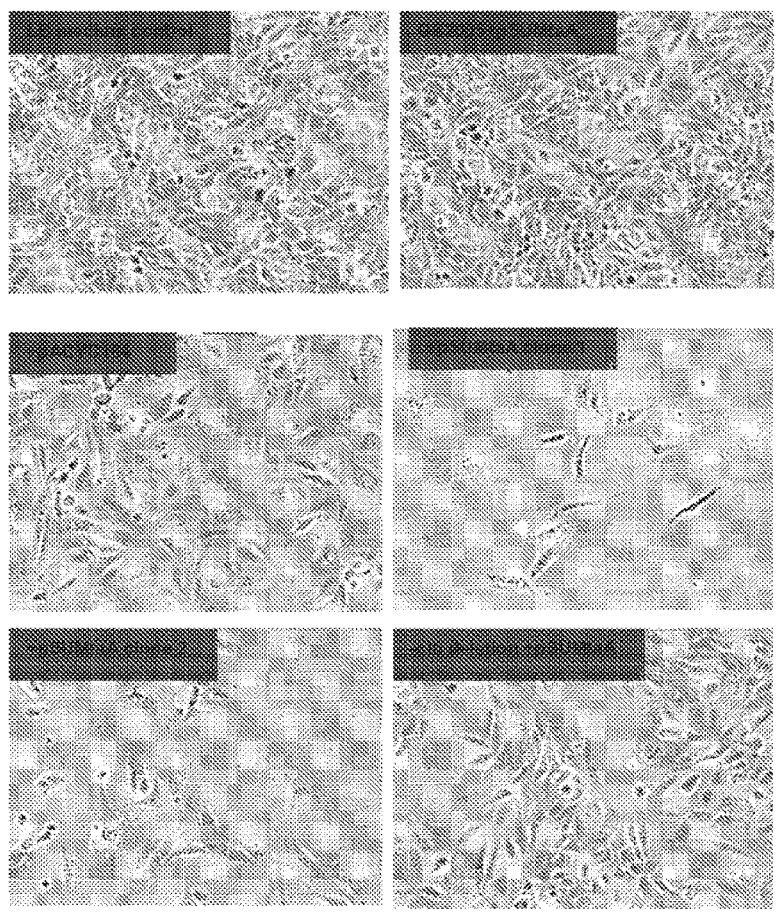
FIG. 21. In vitro test of *E. coli* Nissle 1917 with additional exogenous pPant transferase MtaA. The co-incubation protocol for tumor cells and bacterial cells was followed with method described by Putze et al., 2009 but human U-2 OS osteosarcoma cells were used. A) Giemsa staining of tumor cells incubated with different bacterial strains and without bacterial cells. B) MTT assay of the tumor cells to show the growth inhibition.
Figure 21:
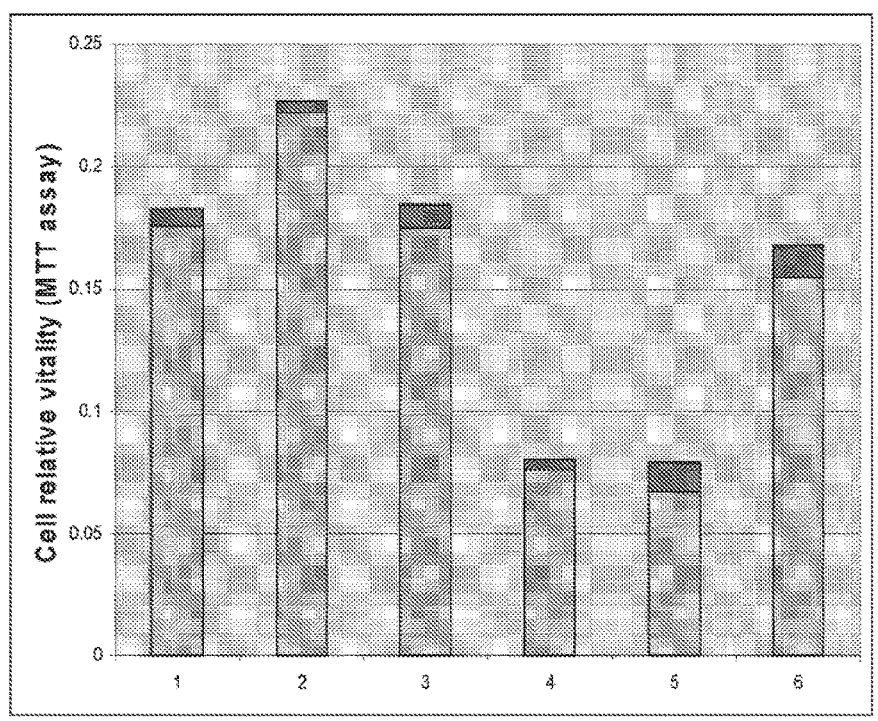

Colibactin has cytopathic activity to against malignant mammalian cells (Nougayrède et al., 2006; Homburg et al., 2007). *E. coli* Nissle 1917 has been shown to have cytopathic activity in vitro but has no effect on tumor growth in vivo (Putze et al., 2009; Stritzker et al., 2007). To investigate the in vitro activity of endogenous colibactin PKS/NRPS gene cluster activated by exogenous pPant transferase (pSUMtaA), human U-2 OS osteosarcoma cells were co-incubated with bacterial cells for 4 hours. Giemsa staining and MTT (thiazolyl blue tetrazolium bromide) assay were performed on the tumor cells after additional 3 days culturing without bacterial cells. Giemsa staining shows that LB medium negative control and *E. coli* K12 strain GB2005 have no cytopathic activity on tumor cells, but all of *E. coli* Nissle 1917 strains have cytopathic activity. *E. coli* Nissle 1917 transformed by control plasmid pACYC184 shows much weaker activity than *E. coli* Nissle 1917 transformed by pSUMtaA (FIG. 21A). It is interesting that MTT assay data shows *E. coli* Nissle 1917+pACYC184 has no effect on tumor cell growth but *E. coli* Nissle 1917+pSUMtaA has strong inhibitory effect on tumor cell growth (FIG. 21B). This data fits with the in vivo data described above in FIG. 17 in Experiment 6. We have shown here that additional exogenous pPant transferase can increase the inhibitory effect of *E. coli* Nissle 1917 on tumor growth in vitro and in vivo.

Example 8

Heterologous Expression of Glidobactin PKS/NRPS Gene Cluster in *E. coli* Nissle 1917

Figure 22:
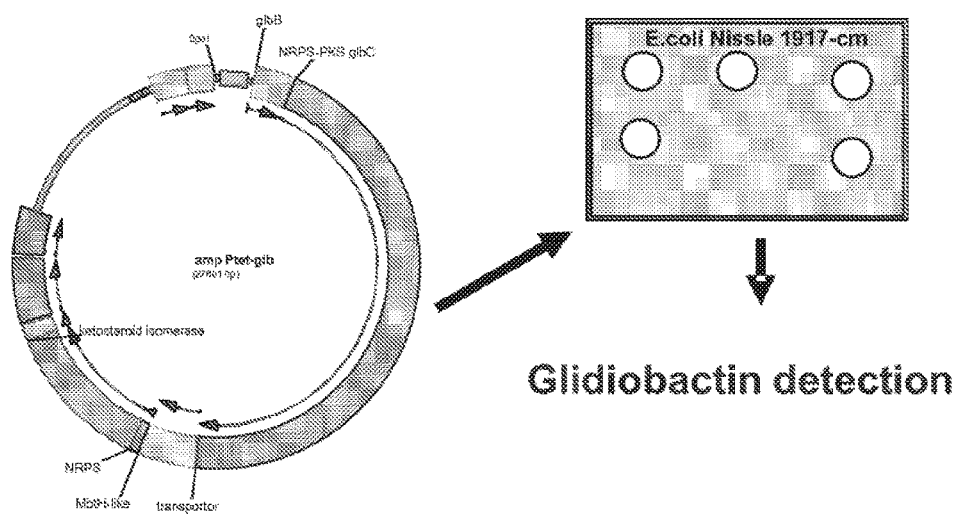
FIG. 22. Glb gene cluster plasmid for expression *E. coli*. Nissle 1917-cm. The complete glb gene cluster was cloned under tetracycline inducible promoter using RecET homologous recombination. This plasmid can replicate in *E. coli* Nissle 1917 and the genes can be expressed following induction by tetracycline.

The plasmid pGB-Ptet-glb was transformed into *E. coli* Nissle 1917-cm (FIG. 19B), which the cm gene in front of endogenous pPant transferase gene to drive its expression constitutively (FIG. 22). This plasmid carries the glidobactin gene cluster under tetracycline inducible promoter (FIG. 22). Following tetracycline induction, compounds were extracted and detected to monitor glidobactin production. Table 4 shows that glidobactin compounds were successfully synthesized.

TABLE 4

Compounds produced by *E. coli* Nissle 1917-cm wild-type and *E. coli* Nissle 1917-cm carrying the glidobactin gene cluster.

| Strain | Compound |
| --- | --- |
| *E. coli* Nissle 1917-cm wild-type | — |
| *E. coli* Nissle 1917-cm + pGB-Ptet-glb | glidobactin A,B,C |

Example 9

Development of *E. coli* Nissle 1917 and K12 as Heterologous Hosts for Epothilone, Tubulysin and Disorazol Production within Tumours In addition to expressing the glidobactin gene cluster in *E. coli* Nissle 1917, it will be useful to express other compounds such as epothilone, tubulysin, disorazol and related compounds in *E. coli* Nissle 1917 and other cells. It will be especially useful to develop systems for expressing secondary metabolites in vivo, for example by bacteria targeted to tumors.

Current methods for the expression of epothilone in *E. coli* are not suitable for in vivo expression because they require propionate feeding in the culturing medium, IPTG induction or arabinose induction. New *E. coli* strains for epothilone, tubulysin or disorazole expression under anaerobic (or in vivo) conditions, at 37° C. and without feeding of propionate need to be generated for in vivo experimentation and use. The protocol below allows the expression of epothilone, tubulysin and disorazol and related compounds in *E. coli* Nissle 1917 and K12.

4'-phosphopantetheinyl transferase (pPant transferase) for posttranslational modification of the PKS proteins and substrates for starter units and extending units are required for PKS gene cluster expression in *E. coli*. Substrates like methylmalonyl-CoA (MM-CoA) are not synthesized in *E. coli*. Therefore, an *E. coli* strain was engineered to synthesize methylmalonyl-CoA. (2S)-methylmalonyl-CoA is a common extender substrate for the biosynthesis of complex polyketides by modular polyketide synthases like epothilone and salinomycin synthases. There are 3 ways in which (2S)-methylmalonyl-CoA can be produced in *E. coli*.

(1) methylmalonyl-CoA mutase/epimerase pathway—B12 or hydroxocobalamin (B12 precursor) must be fed. This will work without B12 due to endogenous production but at low rate.

(2) propionyl-CoA carboxylase (PCC) pathway—requires that propionate is fed.

(3) malonyl/methylmalonyl-CoA ligase (matB) pathway—methylmalonate must be fed and produce most of the (2S,2R)-methylmalonyl-CoA (47% of CoA pool), but produce trace amount 6dEB (6-Deoxyerythronolide) from DEBS (erythromycin gene cluster). This pathway will not be discussed here.

Figure 23:
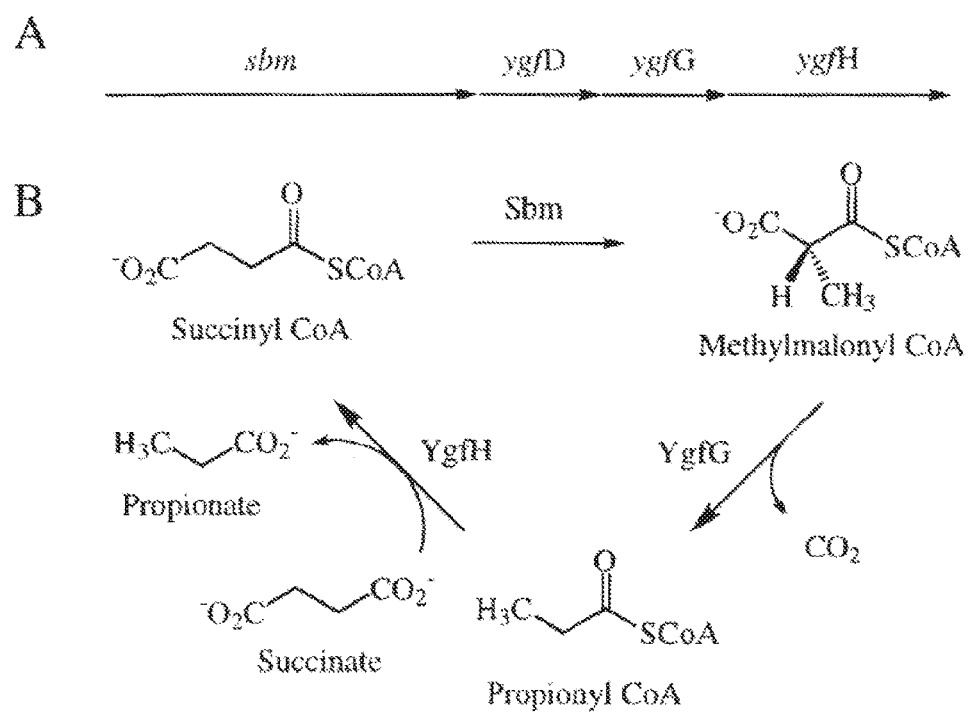
FIG. 23. Methylmalonyl-CoA catabolic pathway present in *E. coli*.

The Methylmalonyl-CoA mutase/epimerase pathway is a pathway that produces methylmalonyl-CoA and propionyl-CoA in *E. coli* (FIG. 23). Although *E. coli* possesses a gene (sbm) that encodes a putative methylmalonyl-CoA mutase, neither mutase activity nor methylmalonyl-CoA is detectable in cell extracts. This gene is tightly controlled. Even if the gene sbm is expressed, the product (methylmalonyl-CoA mutase from *E. coli*) only catalyzes the isomerization of the (R)-diastereomer of methylmalonyl CoA (L-methylmalonyl-CoA or (2R)-methylmalonyl-CoA) and succinyl CoA. *E. coli* K12 has no methylmalonyl-CoA epimerase which converts (2R)-methylmalonyl-CoA to (2S)-methylmalonyl-CoA, the active substrate for PKS. Therefore, methylmalonyl-CoA epimerase was introduced into *E. coli* for (2S)-methylmalonyl-CoA synthesis. For accumulation of methylmalonyl-CoA, the ygfG gene was removed. YgfG is methylmalonyl-CoA decarboxylase and it can convert (2S)- and (2R)-methylmalonyl-CoA into propionyl-CoA. To accumulate propionyl-CoA, ygfH was removed. YgfH is propionyl CoA:succinate CoA transferase which catalyzes the conversion of propionyl-CoA to propionate.

Additionally, *E. coli* does not contain coenzyme B12. Methylmalonyl-CoA mutase apo-enzymes require reconstitution with coenzyme B12 to form the active holo-enzyme.

Methylmalonyl-CoA mutase/epimerase genes from other species have been expressed in *E. coli*. *Propionibacteria shennanii* methylmalonyl-CoA mutaseAB/epimerase encoding genes have been integrated into the yfgG locus in *E. coli*. The Mutase/epimerase genes are under T7 promoter (T7prom-mutAB-T7prom-epi-T7). They were also introduced in *E. coli* in an expression plasmid. In the absence of hydroxocobalamin (a precursor of B12), mutase activity was undetectable unless extracts were supplemented with coenzyme B12, indicating exclusive expression of the apoenzyme. 10% of total CoA, corresponding to ~40 μM, is methylmalonyl-CoA from expression of *Propionibacteria shermanii* methylmalonyl-CoA mutaseAB or *E. coli* methylmalonyl-CoA mutase. There is no propionyl-CoA.

To allow this pathway to function, B12 or its precursor was fed for active mutase expression and ygfG gene was removed to accumulate MM-CoA.

Figure 24:
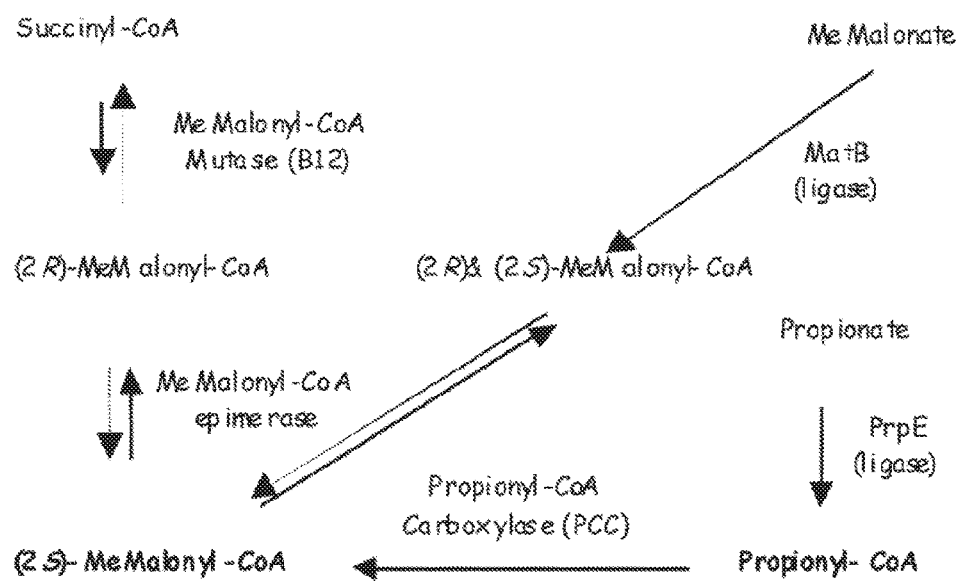
FIG. 24. Pathways for (2S)-methylmalonyl-CoA and Propionyl-CoA synthesis.

There are no propionyl-CoA carboxylase (PCC) genes for the Propionyl-CoA carboxylase pathway in *E. coli*. Propionyl CoA is carboxylated by propionyl CoA carboxylase to form the (2S)-methylmalonyl-CoA (FIG. 24). In mammalian cells and many bacterial cells, propionyl-CoA can be metabolized into (2S)-methylmalonyl-CoA directly by propionyl-CoA carboxylase (PCC) which has two subunits; A and B. Two genes, pccA and pccB, encode PCC. Biotin is a cofactor essential for PCC activity. Human pccA and B, *Streptomyces coelicolor* pccA and B, or *Streptomyces coelicolor* accA (acetyl-CoA carboxylase) and pccB gene pairs have been expressed in *E. coli*. The activity of the biotinylated subunit (pccA) can be enhanced upon coexpression of the *E. coli* birA biotin ligase gene. There is no or very little propionyl-CoA synthesis in *E. coli*. To produce and accumulate propionyl-CoA in *E. coli*, 3 steps have been accomplished. 1, propionate was fed for *E. coli* culture. 2, the prp operon, which is putatively responsible for propionate catabolism in *E. coli*, was deleted. 3, PrpE is CoA transferase and it is thought to convert propionate into propionyl-CoA.

The important innovations that allow the function of this pathway are: 1, propionate feeding; 2, co-expression of birA gene; 3, propionyl-CoA pathway is better than methylmalonyl-CoA mutase/epimerase for 6-dEB production from DEBS gene cluster expression; 4, Production rate of polyktides in *E. coli* at lower than 30° C. (22° C. for 6dEB and 15° C. for Epothilones).

Further to the pathways discussed above, there is an additional silent pathway that produces propionyl-CoA. Studies have shown that propionyl-CoA carboxylase (PCC) pathway is better than MM-CoA mutase/epimerase pathway for 6-dEB production. There are two reasons to be considered: 1, PCC pathway coverts propionyl-CoA to (2S)-methylmalonyl-CoA only which can be directly used by PKS; 2, MM-CoA mutase catalyzes (2R)-methylmalonyl-CoA to succinyl-CoA and its reverse activity is converting succinyl-CoA to (2R)-methylmalonyl-CoA. (2R)-MM-CoA cannot be used by PKS and it must be epimerized to (2S)-form by epimerase for PKS. Epimerase activity is bi-directional. From these points, the synthesis of (2S)-MM-CoA by mutase/epimerase is not more efficient than PCC pathway.

Figure 25:
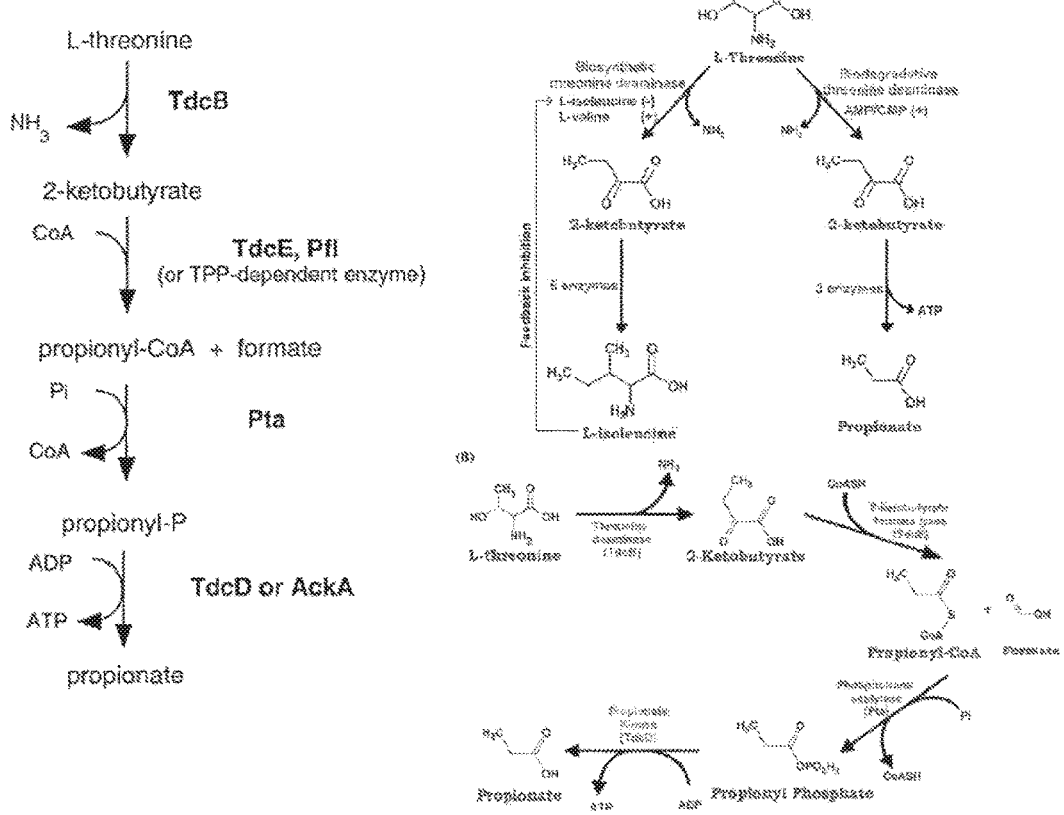
FIG. 25. L-theronine metabolic pathway to generate propionyl-CoA in *E. coli*.

The involvement of 2-ketobutyrate as a precursor in L-isoleucine biosynthesis has been well studied, however, the route of anaerobic 2-ketobutyrate catabolism in *E. coli* is less well understood. Working with *Salmonella typhimurium*, (Van Dyk and LaRossa 1987) demonstrated that phosphotransacetylase (Pta) and acetate kinase are involved in the aerobic degradation of 2-ketobutyrate, indicating that propionyl-CoA is an intermediate. (Hesslinger et al., 1998) proposed an anaerobic pathway in *E. coli* that degrades L-threonine to propionate (FIG. 25). FIG. 25 shows that propionyl-CoA can be generated via L-threonine metabolism.

Figure 26:
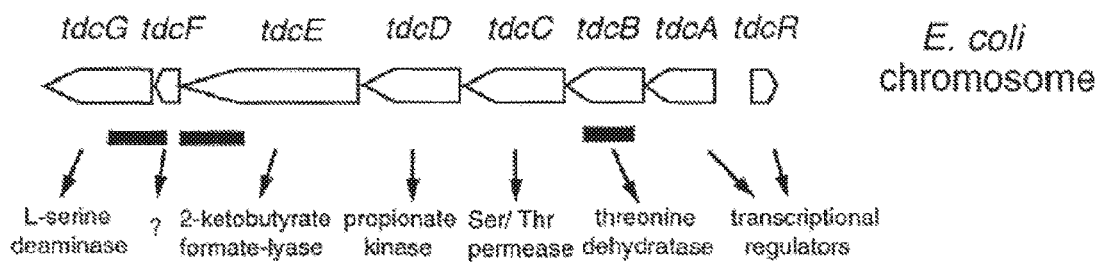
FIG. 26. tcd operon in *E. coli* for L-theronine metabolism.

As discussed above, there is no propionyl-CoA produced in *E. coli* under normal culture conditions. This pathway must be silent in aerobic conditions. The tdc operon is shown in FIG. 26. Expression of the tdc operon is controlled directly by a number of positive transcriptional regulators, including CRP (cyclic-AMP-catabolite gene activator protein complex), IHF (integration host factor), TdcA and TdcR (encoded in the tcd operon), and is controlled indirectly by FNR. FNR is a dimeric, class II transcription factor, which activates gene expression when *E. coli* grows anaerobically.

FIG. 26 shows a detail of the L-threonine metabolism pathway. To produce propionyl-CoA in *E. coli* without the feeding of propionate as in current methods, tcdB (threonine deaminase or dehydratase) and tcdE (2-ketobutyrate formate-lyase) were expressed. To accumulate propionyl-CoA, Pta (phosphotransacetylase) was removed.

The significant innovations that allow this pathway to be activated are: 1, activation of tcdB and tcdE genes to synthesize propionyl-CoA; 2, deletion of Pta or Pta plus tcdD to accumulate propionyl-CoA.

Finally, to generate *E. coli* strains suitable for heterologous expression of epothilone, tubulysin and disorazol gene clusters, the following developments were made. Pta and ygfG genes in Nissle and K12 were removed Pta gene and ygfG gene using loxP* strategy. Super plasmids to express necessary components in Nissle and K12 were generated. First of all, pPant transferase genes from *Agrobacterium* and *Myxococcus xanthus* were integrated into the plasmid although there is a pPant transferase gene presented in front of PKS gene cluster in *E. coli* Nissle 1917. This is because it is not known whether the pPant transferase gene *E. coli* Nissle 1917 is functional, but it is known that the production of PKS gene cluster is functional in *Agrobacterium* and *Myxococcus xanthus*. Their pPant transferase genes are under a constitutive promoter (FIGS. 27-30).

Figure 29:
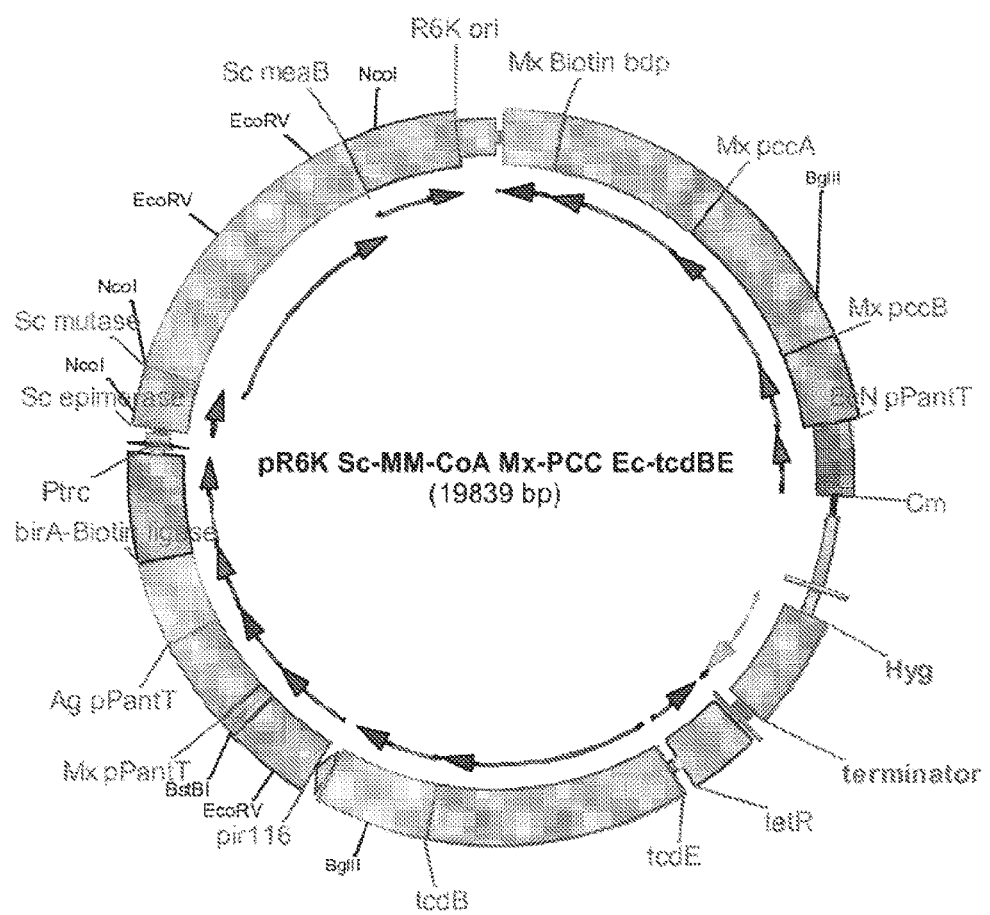
FIG. 29. pR6K-Sc MM-CoA Mx-PCC Ec-tcdBE expression plasmid for MM-CoA mutase/epimerase and PCC pathway.
Figure 30:
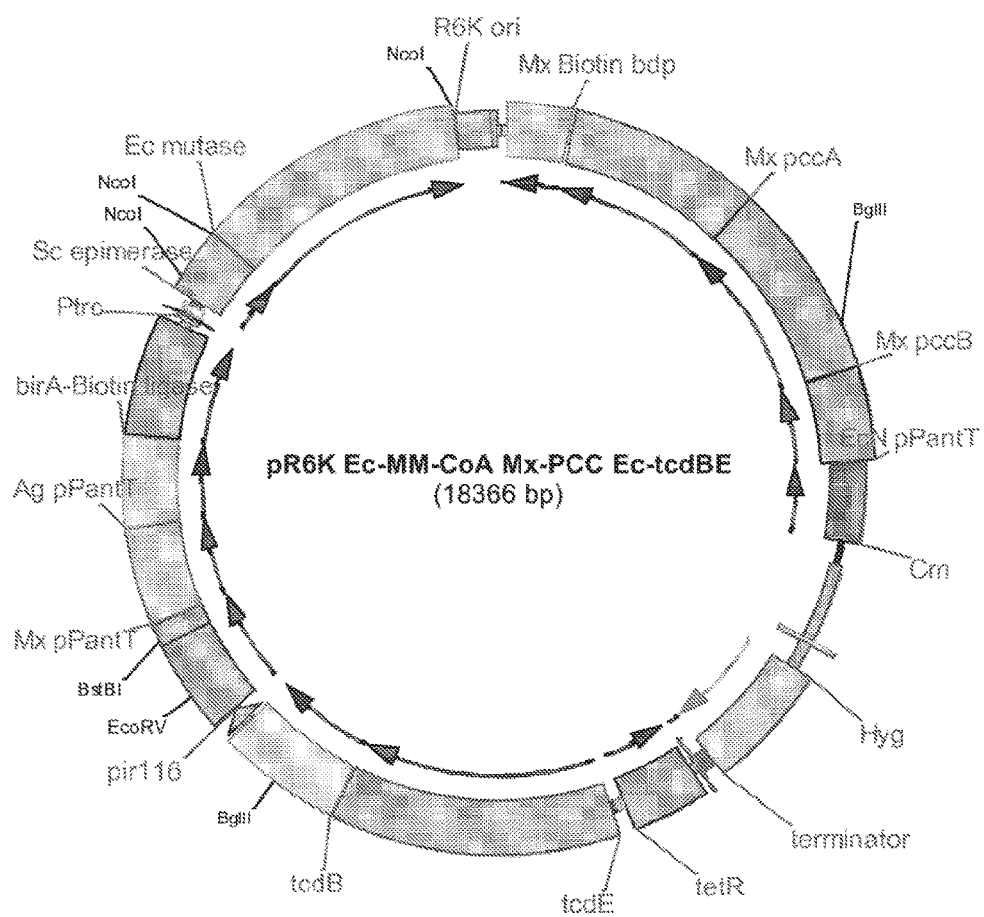
FIG. 30. pR6K-Ec MM-CoA Mx-PCC Ec-tcdBE expression plasmid for MM-CoA mutase/epimerase and PCC pathway.

To produce propionyl-CoA in *E. coli* as substrate for propionyl-CoA carboxylase to synthesize (2S)-methylmalonyl-CoA without the feeding of propionate, tcdB and tcdE were expressed under a tetracycline promoter in case they are not functional in *E. coli* (FIGS. 29 and 30).

Figure 27:
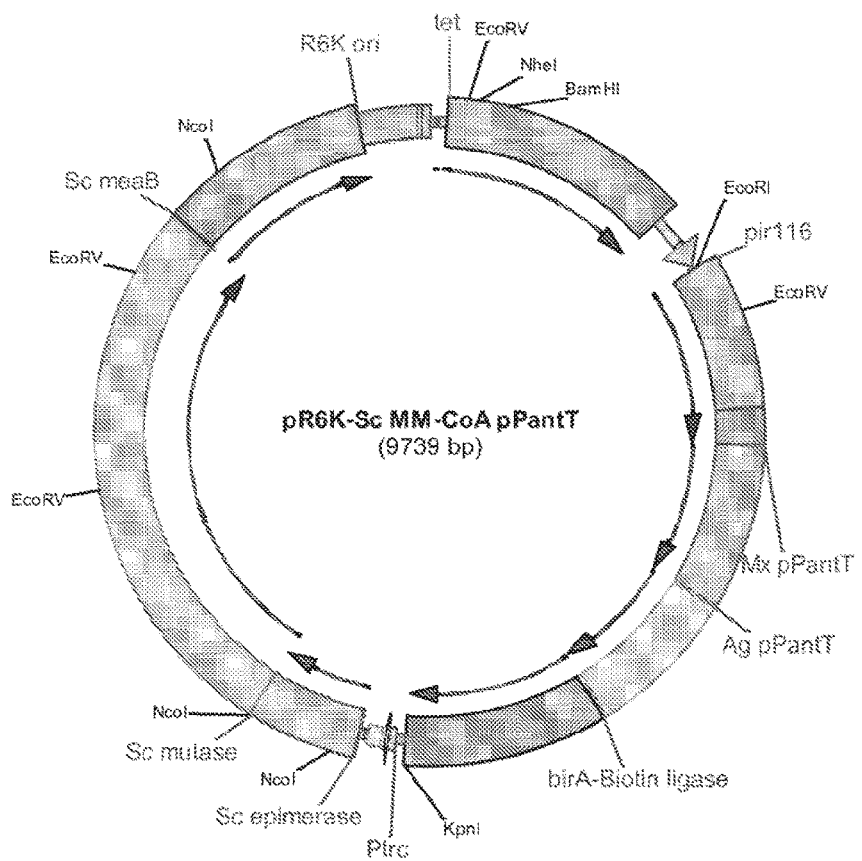
FIG. 27. pR6K-Sc MM-CoA pPantT expression plasmid for MM-CoA mutase/epimerase pathway.
Figure 28:
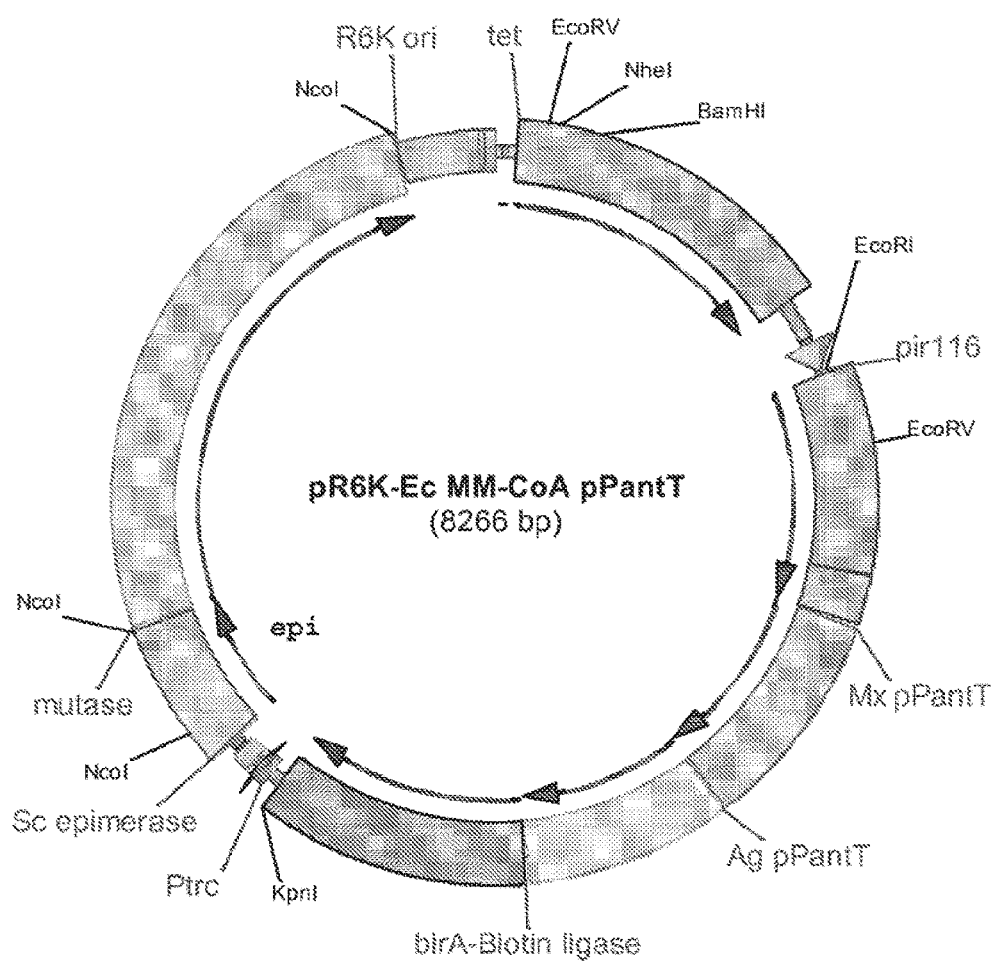
FIG. 28. pR6K-Ec MM-CoA pPantT expression plasmid for MM-CoA mutase/epimerase pathway.

MM-CoA mutase/epimerase pathway and PCC pathway are under a constitutive promoter. BirA gene is under a constitutive promoter as well (FIGS. 27 and 28).

Super plasmids were generated to contain tcdB, tcdE, birA, MM-coA mutase genes from *E. coli*, MM-CoA epimerase from *M. xanthus* and pcc (propionyl-CoA carboxylase) operon from *M. xanthus*, or MM-CoA mutase/epimerase genes from So. ce56 (FIGS. 29 and 30). Lipid A modified (msbB⁻), auxotrophic (purI⁻), yersiniabactin gene cluster (ybt) and lacIZ were also deleted to reduce the bacterial toxicity. This plasmid is, therefore suitable for the expression of epothilone, tubulysin and disorazol gene clusters in *E. coli* Nissle 1917 and K12.

It will be understood that the invention has been described above by way of example only and that modifications in detail may be made within the scope of the invention.

REFERENCES

Konishi, et al. (Sep. 8, 1987) U.S. Pat. No. 4,692,510.
Oka, et al. (May 3, 1988) U.S. Pat. No. 4,742,047.
Oka, et al. (Oct. 11, 1988) U.S. Pat. No. 4,777,160.
Oka, et al. (Dec. 6, 1988) U.S. Pat. No. 4,789,731.
Knoishi, et al. (May 23, 1989) U.S. Pat. No. 4,833,076.
Abril M A, Michan C, Timmis K N, Ramos J L. (1989) Regulator and enzyme specificities of the TOL plasmid-encoded upper pathway for degradation of aromatic hydrocarbons and expansion of the substrate range of the pathway. *J Bacteriol*. December; 171(12):6782-90.

Agrawal N, Bettegowda C, Cheong I, Geschwind J F, Drake C G, Hipkiss E L, Tatsumi M, Dang L H, Diaz L A Jr, Pomper M, Abusedera M, Wahl R L, Kinzler K W, Zhou S, Huso D L, Vogelstein B. (2004) Bacteriolytic therapy can generate a potent immune response against experimental tumors. *Proc Natl Acad Sci USA.* 101(42):15172-7

Altenhoefer A, Oswald S, Sonnenborn U, Enders C, Schulze J, Hacker J, Oelschlaeger T A. (2004) The probiotic *Escherichia coli* strain Nissle 1917 interferes with invasion of human intestinal epithelial cells by different enteroinvasive bacterial pathogens. *FEMS* Immunol Med Microbiol. 40(3):223-9.

Amrein, H. et al. (2004) Functional analysis of genes involved in the synthesis of syringolin A by *Pseudomonas syringae* pv. *syringae* B301D-R. *Mol. Plant Microbe Interact* 17: 90-97.

Barbara, S., Laurent, B., and Robert, D. (2007) Identification of genes involved in the biosynthesis of the cytotoxic compound glidobactin from a soil bacterium. *Environmental Microbiology* 9: 1640-1.

Binns, A. N. and Thomashow M. F. (1988) Cell biology of *Agrobacterium* infection and transformation of plants. Annual Review of *Microbiology* 42: 575-606.

Brown, J. M., Giaccia, A. J. (1998) The unique physiology of solid tumors: opportunities (and problems) for cancer therapy. *Cancer Res* 58: 1408-16.

Bryan, J., and Sanjay, S. (2002) Heterologous expression of epothilone biosynthetic genes in *Myxococcus xanthus*. *Antimicrob. Agents. Chemother* 46: 2772-2778.

Carroll C L, Johnston J V, Kekec A, Brown J D, Parry E, Cajica J, Medina I, Cook K M, Corral R, Pan P S, McAlpine S R. (2005) Synthesis and cytotoxicity of novel sansalvamide A derivatives. *Org Lett.* 7(16):3481-4.

Christopher, N. B., Kinya, H., Martha, L. T., R. Edward, W., and Chaitan, K. (2004) Precursor-Directed Biosynthesis of Epothilone in *Escherichia coli. J. AM. CHEM. SOC* 1 2 6: 7 4 3 6-7437.

Clark, A. J. et al. (1984) Genes of the RecE and RecF pathways of conjugational recombination in *Escherichia coli. Cold Spring Harb. Symp. Quant. Biol* 49: 453-462.

Coleman, C. S. et al. Syringolin A, (2006) a new plant elicitor from the phytopathogenic bacterium *Pseudomonas syringae* pv. *syringae*, inhibits the proliferation of neuroblastoma and ovarian cancer cells and induces apoptosis. *Cell Prolif.* 39: 599-609.

Ditta, G., Stanfield, S., Corbin, D., Helinski, D. R. (1980) Broad host range DNA cloning system for gram-negative bacteria: construction of a gene bank of *Rhizobium meliloti. Proc Natl Acad Sci* 77: 7347-51.

Fisher B, Brown A, Wolmark N, Fisher E R, Redmond C, Wickerham D L, Margolese R, Dimitrov N, Pilch Y, Glass A, et al. (1990) Evaluation of the worth of *corynebacterium parvum* in conjunction with chemotherapy as adjuvant treatment for primary breast cancer. Eight-year results from the National Surgical Adjuvant Breast and Bowel Project B-10. *Cancer.* 15; 66(2):220-7.

Frary, A., Hamilton, C. M. (2001) Efficiency and stability of high molecular weight DNA transformation: an analysis in tomato. *Transgenic Res* 10: 121-132.

Fu, J., Wenzel, S. C., Perlova, O., Wang, J., Gross, F., Tang, Z., Yin, Y., Stewart, A. F., Müller, R. & Zhang, Y. (2008). Efficient transfer of two large secondary metabolite pathway gene clusters into heterologous hosts by transposition. *Nucleic Acids Res.* 36:e113.

Gaitatzis N, Hans A, Müller R, and Beyer S. (2001) The mtaA gene of the myxothiazol biosynthetic gene cluster from *Stigmatella aurantiaca* DW4/3-1 encodes a phosphopantetheinyl transferase that activates polyketide synthases and polypeptide synthetases. *J. Biochem.* 129(1): 119-24

Gerth K, Bedorf N, Höfle G, Irschik H, Reichenbach H. (1996) Epothilons A and B: antifungal and cytotoxic compounds from *Sorangium cellulosum* (Myxobacteria). Production, physico-chemical and biological properties. *J Antibiot (Tokyo).* 49(6):560-3.

Gilbert N. Belofsky, Paul R. Jensen, and William Fenical. Sansalvamide. (1999) A New Cytotoxic Cyclic Depsipeptide Produced by a Marine Fungus of the Genus *Fusarium. Tetrahedron Letters* 40:2913-2916.

Gross, F., Ring, M. W., Perlova, O., Fu, J., Schneider, S., Gerth, K., Kuhlmann, S., Stewart, A. F., Zhang, Y. and Müller, R. (2006) Metabolic engineering of *Pseudomonas putida* for methylmalonyl-CoA biosynthesis to enable complex heterologous secondary metabolite formation. *Chem. Biol* 13: 1-13.

Gust et al., (2003) PCR-targeted *Streptomyces* gene replacement identifies a protein domain needed for biosynthesis of the sesquiterpene soil odor geosmin.' PNAS USA (2003) 100:1541-1546)

Hamilton, C. M. (1997) A binary-BAC system for plant transformation with high-molecular-weight DNA. *Gene* 200:107-116.

Hamilton, C. M., Frary, A., Lewis, C., Tanksley, S. D., (1996) Stable transfer of intact high molecular weight DNA into plant chromosome. *Proc. Natl. Acad. Sci* 93: 9975-9979.

Hesslinger C, Fairhurst S A, Sawers G. (1998) Novel keto acid formate-lyase and propionate kinase enzymes are components of an anaerobic pathway in *Escherichia coli* that degrades L-threonine to propionate. *Mol Microbiol.* 27(2):477-92.

Homburg S, Oswald E, Hacker J, Dobrindt U. (2007) Expression analysis of the colibactin gene cluster coding for a novel polyketide in *Escherichia coli. FEMS Microbiol Lett.* 275(2):255-62.

Jean-Philippe, N., Stefan, H. Fre'de'ric, T., Michele, Boury, Elzbieta, B., Gerhard, G., Carmen, B., Jorg, H., Ulrich, D., Eric, Oswald. (2006) *Escherichia coli* Induces DNA Double-Strand Breaks in Eukaryotic Cells. *Science* 313: 848-851.

Jia L J, Xu H M, Ma D Y, Hu Q G, Huang X F, Jiang W H, Li S F, Jia K Z, Huang Q L, Hua Z C. (2005) Enhanced therapeutic effect by combination of tumor-targeting *Salmonella* and endostatin in murine melanoma model. *Cancer Biol Ther.* 4(8):840-5.

Jochen, S., Stephanie, W. C., Philip, J. H., Tobias, A. O., Werner, G., Aladar, A. S. (2007) Tumor-specific colonization, tissue distribution, and gene induction by probiotic *Escherichia coli* Nissle 1917 in live mice. J *Medical Microbiology* 297: 151-162.

Kang, Y., Son, M. S., Hoang, T. T. (2007) One step engineering of T7-expression strains for protein production: increasing the host-range of the T7-expression system. *Protein Expr Purif* 55:325-33.

Kealey et al., (1998) 'Production of a polyketide natural product in nonpolyketide-producing prokaryotic and eukaryotic hosts', *PNAS USA,* 95:505-509

Kohwi, Y., Imai, K., Tamura, Z., Hashimoto, Y. (1978) Antitumor effect of *Bifidobacterium infantis* in mice. *Gann* 69: 613-8.

Lee C H, Wu C L, Shiau A L. (2004) Endostatin gene therapy delivered by *Salmonella choleraesuis* in murine tumor models. *J Gene Med.* 6(12):1382-93.

Lee C H, Wu C L, Shiau A L. (2005a) Systemic administration of attenuated *Salmonella choleraesuis* carrying thrombospondin-1 gene leads to tumor-specific transgene expression, delayed tumor growth and prolonged survival in the murine melanoma model. *Cancer Gene Ther.* (2):175-84.

Lee C H, Wu C L, Shiau A L. (2005b) Systemic administration of attenuated *Salmonella choleraesuis* carrying thrombospondin-1 gene leads to tumor-specific transgene expression, delayed tumor growth and prolonged survival in the murine melanoma model. *Cancer Gene Ther.* 12(2):175-84.

LiJun, J., HanMei, X., DingYuan, M., QinGang, H., XiaoFeng, H., WenHui, J., ShuFeng, L., KunZhi, Jia., QiLai, H., ZiChun, H. (2005) Enhanced Therapeutic Effect by Combination of Tumor-Targeting *Salmonella* and Endostatin in Murine Melanoma Model. *Cancer Biology & Therapy* 4: 840-845.

Lodinová-Zádniková R, Sonnenborn U. (1997) Effect of preventive administration of a nonpathogenic *Escherichia coli* strain on the colonization of the intestine with microbial pathogens in newborn infants. *Biol Neonate.* 71(4): 224-32.

Loeffler M, Le'Negrate G, Krajewska M, Reed J C. (2007) Attenuated *Salmonella* engineered to produce human cytokine LIGHT inhibit tumor growth. *Proc Natl Acad Sci USA.* 104(31):12879-83

Long, H. D., Chetan, B., David, L. H., Kenneth, W. K., and Bert, V. (2001) Combination bacteriolytic therapy for the treatment of experimental tumors. *PNAS* 98: 15155-15160.

Low, K. B., Ittensohn, M., Le, T., et al. (1999) Lipid A mutant *Salmonella* with suppressed virulence and TNFa induction retain tumor-targeting in vivo. *Nat Biotechnol* 17: 37-41.

Malmgren R A, Flanigan C C. (1955) Localization of the vegetative form of *Clostridium tetani* in mouse tumors following intravenous spore administration. *Cancer Res.* 15(7):473-8.

Mark, M., Gregory, J. P., and Anath D. (1990) Efficient transformation of *Agrobacterium tumefaciens* by electroporation. *Gene* 90: 149-151.

Markus, L., Gaelle, L., Maryla, K., and John, C. R. (2007) Attenuated *Salmonella* engineered to produce human cytokine LIGHT inhibit tumor growth. *PNAS* 104: 12879-12883.

Matthysse, A. G. (1986) Initial interactions of *Agrobacterium tumefaciens* with plant host cells. Critical Reviews in *Microbiology* 13: 281-307.

Michel, K., Abderhalden, O., Bruggmann, R., and Dudler, R. (2006) Transcriptional changes in powdery mildew infected wheat and *Arabidopsis* leaves undergoing syringolin triggered hypersensitive cell death at infection sites. *Plant Mol Biol* 62: 561-578.

Moese, J. R., Moese, G. (1964) Oncolysis by *clostridia*. I. Activity of *Clostridium butyricum* (m-55) and other non-pathogenic *clostridia* against the ehrlich carcinoma. *Cancer Res* 24: 212-6.

Mutka, S. C., Carney, J. R., Liu, Y., and Kennedy, J. (2006) Heterologous production of epothilone C and D in *Escherichia coli. Biochemistry* 45: 1321-30.

Muyrers et al., 1999 (Rapid modification of bacterial artificial chromosomes by ET-recombination, Nucleic Acid Res., 27, 1555-1557)

Muyrers, J. P. P. et al., 2000a ET-Cloning: Think Recombination First. *Genetic Eng.*, vol. 22, 77-98.

Muyrers J. P et al., 2000b Point mutation of bacterial artificial chromosomes by ET recombination, *EMBO Reports*, 1, 239-243

Muyrers J. P et al., 2000c RecE/RecT and Redα/Redβa initiate double-stranded break repair by specifically interacting with their respective partners, *Genes Dev.*, 14 1971-1982

Muyrers, J. P. P et al., 2001 Techniques: Recombinogenic engineering-new options for cloning and manipulating DNA, *Trends in Biochem. Sci.*, 26, 325-31

Narayanan K. et al., (1999) Efficient and precise engineering of a 200 kb β-globin human/bacterial artificial chromosome in *E. coli* DH10B using an inducible homologous recombination system, *Gene Therapy*, 6, 442-447

Nester, E. W., Gordon, M. P., Amasino, R. M. and Yanofsky, M. F. (1984) Crown gall: a molecular and physiological analysis. Annual Review of *Plant Physiology* 35: 387-413.

Newman, J. R., Fuqua, C. (1999) Broad-host-range expression vectors that carry the L-arabinose-inducible *Escherichia coli* araBAD promoter and the araC regulator. *Gene* 227:197-203.

Nougayrède J P, Homburg S, Taieb F, Boury M, Brzuszkiewicz E, Gottschalk G, Buchrieser C, Hacker J, Dobrindt U, and Oswald E. (2006) *Escherichia coli* induces DNA double-strand breaks in eukaryotic cells. *Science.* 313 (5788):848-51.

Oka, M., Nishiyama, Y., Ohta, S., Kamei, H., Konishi, M., Miyaki, T., et al. (1988a) Glidobactins A, B and C, new antitumor antibiotics. I. Production, isolation, chemical properties and biological activity. *J Antibiot* 41: 1331-1337.

Oka, M., Yaginuma, K., Numata, K., Konishi, M., Oki, T., and Kawaguchi, H. (1988b) Glidobactins A, B and C, new antitumor antibiotics. II. Structure elucidation. *J Antibiot* 41: 1338-1350.

Oka, M., Ohkuma, H., Kamei, H., Konishi, M., Oki, T., and Kawaguchi, H. (1988c) Glidobactins D, E, F, G and H; minor components of the antitumor antibiotic glidobactin. *J Antibiot* 41: 1906-1909.

Parker R C, Plummer H C, et al. (1947) Effect of histolyticus infection and toxin on transplantable mouse tumors. *Proc Soc Exp Biol Med.* 66(2):461-7.

Pawelek J M, Low K B, Bermudes D. (1997) Tumor-targeted *Salmonella* as a novel anticancer vector. *Cancer Res.* 57(20):4537-44.

Pawelek J M, Sodi S, Chakraborty A K, Platt J T, Miller S, Holden D W, Hensel M, Low K B. (2002) *Salmonella* pathogenicity island-2 and anticancer activity in mice. *Cancer Gene Ther.* 9(10):813-8.

Pawelek J M, Low K B, Bermudes D. (2003) Bacteria as tumour-targeting vectors. *Lancet Oncol.;* 4(9):548-56.

Pawelek J M. (2005) Tumour-cell fusion as a source of myeloid traits in cancer. *Lancet Oncol.* 6(12):988-93.

Perlova, O., Fu, J., Kuhlmann, S., Krug, D., Stewart, A. F., Zhang, Y., and Muller, R. (2006) Reconstitution of the myxothiazol biosynthetic gene cluster by Red/ET recombination and heterologous expression in *Myxococcus xanthus. Appl Environ Microbiol*, 72: 7485-7494.

Pfeifer et al., (2001) Biosynthesis of complex polyketides in a metabolically engineered strain of *E. coli. Science* 291: 1790-1792

Putze J, Hennequin C, Nougayrède J P, Zhang W, Homburg S, Karch H, Bringer M A, Fayolle C, Carniel E, Rabsch W, Oelschlaeger T A, Oswald E, Forestier C, Hacker J, Dobrindt U. (2009) Genetic structure and distribution of the colibactin genomic island among members of the family Enterobacteriaceae. *Infect Immun.* 77(11):4696-703. Epub 2009 Aug. 31.

Rembacken B J, Snelling A M, Hawkey P M, Chalmers D M, Axon A T. (1999) Non-pathogenic *Escherichia coli* versus mesalazine for the treatment of ulcerative colitis: a randomised trial. *Lancet.* August 21; 354(9179):635-9.

Rondon M R, Ballering K S, Thomas M G. (2004) Identification and analysis of a siderophore biosynthetic gene cluster from *Agrobacterium tumefaciens* C58. *Microbiol* 150(Pt 11):3857-66

Schellenberg, B., Bigler, L., and Dudler, R. (2007) Identification of genes involved in the biosynthesis of the cytotoxic compound glidobactin from a soil bacterium. *Environ. Microbiol* 9: 1640-1650.

Schneiker S., et at. (2007) Complete genome sequence of the myxobacterium *Sorangium cellulosum. Nat Biotechnol* 25: 1281-9.

Smith, E. F. and Towsend, C. O. (1907) A plant tumour of bacterial origin. *Science* 25: 671-673.

Shoji, J., Hinoo, H., Kato, T., Hattori, T., Hirooka, K., Tawara, K., et al. (1990) Isolation of cepafungins I, II and III from *Pseudomonas* species. *J Antibiot* 43: 783-787.

Shuanglin, X., Johannes, F., and Chiang, J. Li. (2006) Short hairpin RNA-expressing bacteria elicit RNA interference in mammals. *Nature biotechnology* 24: 6.

Silakowski B, Schairer H U, Ehret H, Kunze B, Weinig S, Nordsiek G, Brandt P, Blöcker H, Höfle G, Beyer S, and Müller R. (1999) New lessons for combinatorial biosynthesis from myxobacteria. The myxothiazol biosynthetic gene cluster of *Stigmatella aurantiaca* DW4/3-1. *J Biol Chem.* 274(52):37391-9.

Stefan, H., Eric, O.2, Jorg, H. and Ulrich, D. (2007) Expression analysis of the colibactin gene cluster coding for a novel polyketide in *Escherichia coli. FEMS Microbiol Lett:* 1-8.

Stritzker J, Weibel S, Hill P J, Oelschlaeger T A, Goebel W, Szalay A A. (2007) Tumor-specific colonization, tissue distribution, and gene induction by probiotic *Escherichia coli* Nissle 1917 in live mice. *Int J Med Microbiol.* 297(3):151-62. Epub 2007 Apr. 19.

Sznol, M., Lin, S. L., Bermudes, D., Zheng, L. M., King, I. (2000) Use of preferentially replicating bacteria for the treatment of cancer. *J Clin Invest* 105: 1027-30.

Tang, L., Sanjay, S., Loleta, C., John, C., Leonard, K., Chaitan, K., and Bryan, J. (2000) Cloning and heterologous expression of the epothilone gene cluster. *Science* 287: 640-642.

Van Dyk T K, LaRossa R A. (1987) Involvement of ack-pta operon products in alpha-ketobutyrate metabolism by *Salmonella typhimurium. Mol Gen Genet.* 207(2-3):435-40.

Vlasák, J., Ondre, j M. (1992) Construction and use of *Agrobacterium tumefaciens* binary vectors with *A. tumefaciens* C58 T-DNA genes. *Folia Microbiol* (Praha) 37:227-30.

Wäspi, U., Blanc, D., Winkler, T., Ruedi, P., and Dudler, R. (1998) Syringolin, a novel peptide elicitor from *Pseudomonas syringae* pv. *syringae* that induces resistance to *Pyricularia oryzae* in rice. *Mol Plant Microbe Interact* 11: 727-733.

Wäspi, U., Hassa, P., Staempfli, A., Molleyres, L.-P., Winkler, T., and Dudler, R. (1999) Identification and structure of a family of syringolin variants: unusual cyclic peptides from *Pseudomonas syringae* pv. *syringae* that elicit defense responses in rice. *Microbiol Res* 154: 1-5.

Wäspi, U., Schweizer, P., and Dudler, R. (2001) Syringolin reprograms wheat to undergo hypersensitive cell death in a compatible interaction with powdery mildew. *Plant Cell* 13:153-161.

Wenzel, S., Gross, F., Zhang, Y., Fu, J., Stewart, F. and Müller, R. (2005) Heterologous expression of a myxobacterial natural products assembly line in *Pseudomonads* via Red/ET recombineering. *Chem. Biol.,* 12: 349-356.

Yi C, Huang Y, Guo Z Y, Wang S R. (2005) Antitumor effect of cytosine deaminase/5-fluorocytosine suicide gene therapy system mediated by *Bifidobacterium infantis* on melanoma. Acta Pharmacol Sin. 26(5):629-34.

Yu Q, Stamenkovic I. (2004) Transforming growth factor-beta facilitates breast carcinoma metastasis by promoting tumor cell survival. *Clin Exp Metastasis.* 21(3):235-42.

Zhang Y. et al., (1998) A new logic for DNA engineering using recombination in *Escherichia coli, Nat. Genet.,* 20, 123-128

Zhang, Y., Muyrers, J. P., Testa, G., and Stewart, A. F. (2000) DNA cloning by homologous recombination in *Escherichia coli. Nature Biotechnology* 18: 1314-1317.

Zhang, Y. et al., 2003 (BMC Mol Biol. 2003 Jan. 16; 4 (1):1))

Zhao M, Yang M, Li X M, Jiang P, Baranov E, Li S, Xu M, Penman S, Hoffman R M. (2005) Tumor-targeting bacterial therapy with amino acid auxotrophs of GFP-expressing *Salmonella typhimurium. Proc Natl Acad Sci USA.* 102(3):755-60.

Zhao M, Yang M, Ma H, Li X, Tan X, Li S, Yang Z, Hoffman R M. (2006) Targeted therapy with a *Salmonella typhimurium* leucine-arginine auxotroph cures orthotopic human breast tumors in nude mice. *Cancer Res.* 66(15): 7647-52.

The invention claimed is:

1. A *Burkholderia* host cell comprising a genetic engineering which provides heterologous expression of all members of a gene cluster which is capable of polyketide synthesis (PKS), non-ribosomal peptide synthesis (NRPS), or hybrid polyketide-NRP synthesis, wherein the *Burkholderia* host cell is a heterologous species with respect to a species of cell which the gene capable of polyketide or non-ribosomal peptide synthesis is derived from, wherein the polyketide, NRP or hybrid polyketide-NRP is not naturally produced in the *Burkholderia* host cell, and wherein the *Burkholderia* host cell used in the genetic engineering is DSM7029.

2. The *Burkholderia* host cell according to claim 1, which is transformed with a gene cluster from one or more organisms selected from the group consisting of myxobacteria, *Agrobacterium tumefaciens, E. coli* Nissle 1917 and *S. aurantiaca*.

3. The *Burkholderia* host cell according to claim 2, wherein the myxobacteria is selected from *Polyangium* and *Sorangium cellulosum*.

4. The *Burkholderia* host cell according to claim 1, wherein the PKS/NRPS gene cluster is the epothilone gene cluster, the tubulysin gene cluster, the disorazol(e) gene cluster, the salinomycin gene cluster, the myxochromide S gene cluster, or the myxothiazol gene cluster.

5. The *Burkholderia* host cell according to claim wherein the host expresses epothilone, myxochromide, colibactin, tubulysin, or disorazol(e) or a functional derivative of such a compound.

6. The *Burkholderia* host cell according to claim 1, wherein the members are found in nature in the gene cluster.

7. The *Burkholderia* host cell according to claim 1, wherein the gene cluster has been engineered.

8. The *Burkholderia* host cell according to claim 7, wherein the gene cluster has been engineered by swapping the genes in the gene clusters.

9. A method for the generation of the *Burkholderia* host cell according to claim 1 which comprises transforming *Burkholderia* DSM7029 with all members of a heterologous gene cluster which is capable of polyketide, non-ribosomal peptide (NRP), or hybrid polyketide-NRP synthesis to generate the *Burkholderia* host cell according to claim 1.

10. The method according to claim 9, wherein the heterologous gene cluster is from one or more organisms selected from the group consisting of myxobacteria, *Agrobacterium tumefaciens, E. coli* Nissle 1917 and *S. aurantiaca*.

11. The method according to claim 10, wherein the myxobacteria is selected from *Polyangium* and *Sorangium cellulosum*.

12. The method according to claim 9, wherein the transforming step incorporates a step of electroporation.

13. The method according to claim 12 further comprising culturing the *Burkholderia* DSM7029 prior to electroporation for over 2 hours.

14. The method according to claim 12, wherein following electroporation, the host cell is cultured for over 30 minutes to recover.

15. A method of treating cancer comprising the step of administering the *Burkholderia* host cell according to claim 1 to a tumor.

* * * * *